(12) United States Patent
Murata et al.

(10) Patent No.: US 8,383,647 B2
(45) Date of Patent: Feb. 26, 2013

(54) QUINOLINE DERIVATIVE

(75) Inventors: Toshiki Murata, Osaka (JP); Masahiro Kamaura, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/138,300

(22) PCT Filed: Jan. 29, 2010

(86) PCT No.: PCT/JP2010/051277
§ 371 (c)(1),
(2), (4) Date: Jul. 29, 2011

(87) PCT Pub. No.: WO2010/087454
PCT Pub. Date: Aug. 5, 2010

(65) Prior Publication Data
US 2012/0035213 A1    Feb. 9, 2012

(30) Foreign Application Priority Data

Jan. 30, 2009   (JP) ................................ 2009-020575

(51) Int. Cl.
*A61K 31/4709*  (2006.01)
*A61P 3/04*     (2006.01)
*C07D 215/38*   (2006.01)

(52) U.S. Cl. ........................ 514/314; 546/171
(58) Field of Classification Search .................. None
See application file for complete search history.

(56) References Cited

U.S. PATENT DOCUMENTS

| | | | |
|---|---|---|---|
| 6,930,185 B2 | 8/2005 | Ishihara et al. |
| 7,183,415 B2 | 2/2007 | Ishihara et al. |
| 7,229,986 B2 | 6/2007 | Ishihara et al. |
| 7,601,868 B2 | 10/2009 | Ishihara et al. |
| 2005/0209213 A1 | 9/2005 | Ishihara et al. |
| 2010/0069362 A1 | 3/2010 | Murata |
| 2011/0015225 A1 | 1/2011 | Murata et al. |

FOREIGN PATENT DOCUMENTS

| | | |
|---|---|---|
| JP | 2004-059567 A | 2/2004 |
| JP | 2008-088120 A | 4/2008 |
| WO | WO 01/21577 A2 | 3/2001 |
| WO | WO 01/82925 A1 | 11/2001 |
| WO | WO 01/87834 A1 | 11/2001 |
| WO | WO 03/035624 A1 | 5/2003 |
| WO | WO 2004/072018 A1 | 8/2004 |
| WO | WO 2006/118320 A1 | 11/2006 |
| WO | WO 2009/021740 A2 | 2/2009 |
| WO | WO 2009/123194 A1 | 10/2009 |

OTHER PUBLICATIONS

International Search Report mailed Mar. 2, 2010, in PCT/JP2010/051277, 4 pages.

*Primary Examiner* — Nizal Chandrakumar
*Assistant Examiner* — Timothy R. Rozof
(74) *Attorney, Agent, or Firm* — Foley & Lardner LLP

(57) ABSTRACT

The present invention provides a compound having a melanin-concentrating hormone receptor antagonistic action and low toxicity, which is useful as an agent for the prophylaxis or treatment of obesity and the like.

The present invention relates to a compound represented by the formula (I):

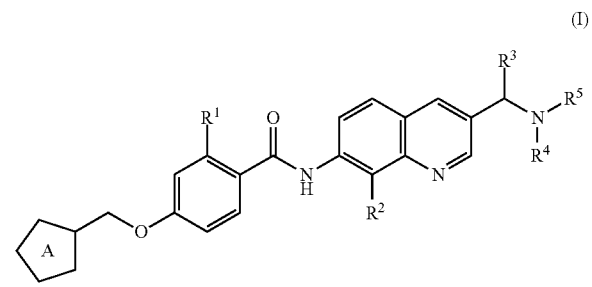

wherein each symbol is as defined in the specification, or a salt thereof.

18 Claims, No Drawings

QUINOLINE DERIVATIVE

TECHNICAL FIELD

The present invention relates to a quinoline derivative having melanin-concentrating hormone (hereinafter sometimes abbreviated as MCH) receptor antagonistic action, and useful as an agent for the prophylaxis or treatment of obesity and the like.

BACKGROUND OF THE INVENTION

MCH is a hypothalamus-derived hormone known to have an appetite increasing action. Furthermore, it has been reported that MCH knockout mouse behaves normally but shows a significantly decreased food ingestion amount and a lighter body weight as compared to normal mouse (Nature, vol. 396, page 670, 1998). Therefrom MCH receptor antagonists are expected to be superior appetite suppressants or anti-obesity agents.

As compounds having a MCH receptor antagonistic action, the following compounds are known.

1) WO01/21577 (patent document 1) discloses a melanin-concentrating hormone antagonist comprising a compound represented by the formula:

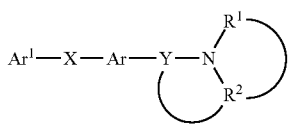

wherein
$Ar^1$ is a cyclic group optionally having substituent(s);
X is a spacer with a main chain having an atom number of 1 to 6;
Y is a bond or a spacer with a main chain having an atom number of 1 to 6;
Ar is a monocyclic aromatic ring optionally condensed with a 4- to 8-membered nonaromatic ring and further optionally having substituent(s);
$R^1$ and $R^2$ are the same or different and each is a hydrogen atom or a hydrocarbon group optionally having substituent(s), $R^1$ and $R^2$ may form, together with the adjacent nitrogen atom, nitrogen-containing heterocycle optionally having substituent(s), $R^2$ forms a Spiro ring together with Ar, or $R^2$ may form, together with the adjacent nitrogen atom and Y, a nitrogen-containing heterocycle optionally having substituent(s),
or a salt thereof.

2) WO01/82925 (patent document 2) discloses a melanin-concentrating hormone antagonist comprising a compound represented by the formula:

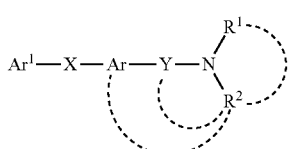

wherein
$Ar^1$ is a cyclic group optionally having substituent(s);
X and Y are the same or different and each is a spacer with a main chain having an atom number of 1 to 6;
Ar is a condensed polycyclic aromatic ring optionally having substituent(s);
$R^1$ and $R^2$ are the same or different and each is a hydrogen atom or a hydrocarbon group optionally having substituent(s), $R^1$ and $R^2$ may form, together with the adjacent nitrogen atom, nitrogen-containing heterocycle optionally having substituent(s), $R^2$ may form, together with the adjacent nitrogen atom and Y, nitrogen-containing heterocycle optionally having substituent(s), or $R^2$ may form, together with the adjacent nitrogen atom, Y and Ar, a nitrogen-containing fused ring optionally having substituent(s),
or a salt thereof.

3) WO01/87834 (patent document 3) discloses a melanin-concentrating hormone antagonist comprising a compound represented by the formula:

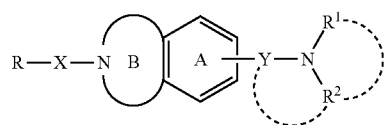

wherein
R is a hydrogen atom, a halogen atom or a cyclic group optionally having substituent(s);
X is a bond or a spacer with a main chain having an atom number of 1 to 10;
Y is a spacer with a main chain having an atom number of 1 to 6;
ring A is a benzene ring further optionally having substituent(s);
ring B is 5- to 9-membered nitrogen-containing nonaromatic heterocycle further optionally having substituent(s);
$R^1$ and $R^2$ are the same or different and each is a hydrogen atom, a hydrocarbon group optionally having substituent(s) or a heterocyclic group optionally having substituent(s), $R^1$ and $R^2$ may form, together with the adjacent nitrogen atom, nitrogen-containing heterocycle optionally having substituent(s), or $R^2$ may form, together with the adjacent nitrogen atom and Y, nitrogen-containing heterocycle optionally having substituent(s),
or a salt thereof.

4) WO03/035624 (patent document 4) discloses a compound represented by the formula:

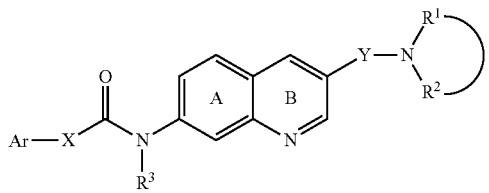

wherein
Ar is a cyclic group optionally having substituent(s);
X is a bond or a spacer with a main chain having an atom number of 1 to 6;
$R^1$ and $R^2$ are the same or different and each is a hydrogen atom or a hydrocarbon group optionally having substituent(s),
$R^1$ and $R^2$ may form, together with the adjacent nitrogen atom, nitrogen-containing heterocycle optionally having substituent(s);

Y is a divalent hydrocarbon group optionally having substituent(s) (excluding CO);
R³ is a hydrogen atom or a hydrocarbon group optionally having substituent(s); and
ring A and ring B may further have substituent(s), and when ring B further has substituent(s), the substituent(s) may be bonded to R¹ to form a ring,
or a salt thereof or a prodrug thereof.
5) WO2004/072018 (patent document 5) discloses a compound represented by the formula:

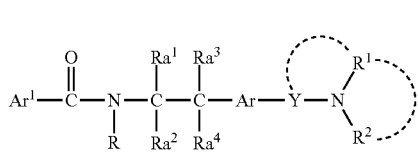

wherein
Ar¹ is a cyclic group optionally having substituent(s); R is a hydrogen atom, optionally halogenated $C_{1-6}$ alkyl, phenyl optionally having substituent(s) or pyridyl optionally having substituent(s);
Ra¹, Ra², Ra³ and Ra⁴ are the same or different and each is a hydrogen atom, optionally halogenated $C_{1-6}$ alkyl, phenyl optionally having substituent(s), a halogen atom, pyridyl optionally having substituent(s), cyano, optionally halogenated $C_{1-6}$ alkoxy, optionally halogenated $C_{1-6}$ alkylthio, amino, mono- or di-$C_{1-6}$ alkylamino, formyl, optionally halogenated $C_{1-6}$ alkyl-carbonyl or optionally halogenated $C_{1-6}$ alkylsulfonyl;
Ar is a monocyclic aromatic ring optionally having substituent(s);
Y is an optionally halogenated alkylene group;
(1) R¹ and R² are the same or different and each is a hydrogen atom or $C_{1-6}$ alkyl, (2) R¹ and R² form, together with the adjacent nitrogen atom, nitrogen-containing heterocycle optionally having substituent(s), (3) R¹ and Y form, together with the adjacent nitrogen atom, nitrogen-containing heterocycle optionally having substituent(s), and R² is a hydrogen atom or $C_{1-6}$ alkyl, provided that when the nitrogen-containing heterocycle formed by R¹ and R² together with the adjacent nitrogen atom is piperazine or when R is $C_{1-4}$ alkyl, then Ar¹ is a cyclic group having substituent(s), or a salt thereof.
6) WO2006/118320 (patent document 6) discloses a compound represented by the formula:

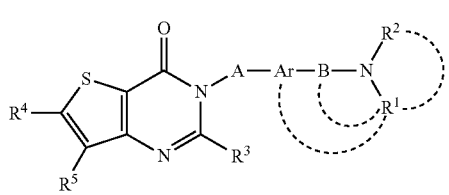

wherein
Ar is an optionally substituted ring;
A is a spacer with a main chain having an atom number of 1 to 4;
B is a bond, a $C_{1-10}$ alkylene group or an oxygen atom;
R³ and R⁵ are each independently a hydrogen atom or a substituent;
R⁴ is an optionally substituted cyclic group or an optionally substituted $C_{1-10}$ alkyl group;
R¹ and R² are each independently a hydrogen atom or a substituent, R¹ is bonded to R² or B to form optionally substituted nitrogen-containing heterocycle, or R¹ is bonded to Ar to form optionally substituted nitrogen-containing fused heterocycle,
or a salt thereof.
7) JP-A-2008-88120 (patent document 7) discloses a compound represented by the formula:

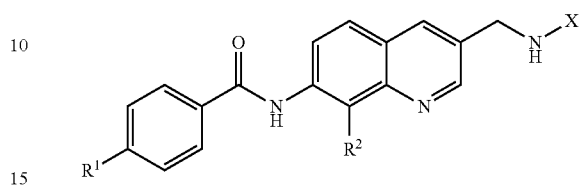

wherein
R¹ is an optionally substituted $C_{1-6}$ alkoxy group;
R² is a hydrogen atom, a methyl group or a halogen atom;
X is a $C_{4-7}$ hydrocarbon group substituted by a hydroxy group or an oxo group,
or a salt thereof.
8) WO2009/123194 (patent document 8) discloses a compound represented by the formula:

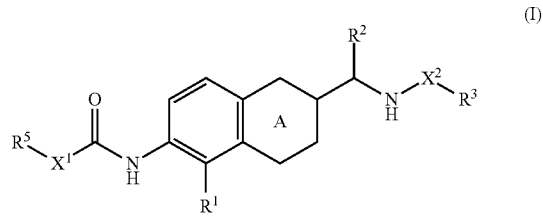

(I)

wherein
ring A is a 6-membered ring further optionally substituted;
R¹ is a hydrogen atom, a halogen atom or a $C_{1-6}$ alkyl group;
R² is a hydrogen atom or a $C_{1-6}$ alkyl group;
R³ is a group represented by the formula: —Y—S(O)$_{m1}$—R$^{4a}$
wherein
Y is a bond or NH; m1 is an integer of 1 or 2; R$^{4a}$ is a $C_{1-6}$ alkyl group optionally substituted by 1 to 3 halogen atoms, or a cyclic group represented by the formula:

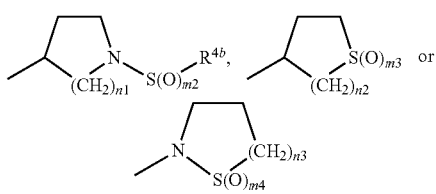

wherein m2, m3, m4, n1, n2 and n3 are independently an integer of 1 or 2; R$^{4b}$ is a $C_{1-6}$ alkyl group optionally substituted by 1 to 3 halogen atoms (the ring moiety of the cyclic group is optionally further substituted);
R⁵ is a 5- or 6-membered cyclic group optionally further substituted;
X¹ is a bond or a $C_{1-6}$ alkylene group; and
X² is a bond or a $C_{1-6}$ alkylene group,
or a salt thereof.

PRIOR ART DOCUMENTS

Patent Documents patent document 1: WO01/21577
patent document 2: WO01/82925
patent document 3: WO01/87834
patent document 4: WO03/035624
patent document 5: WO2004/072018
patent document 6: WO2006/118320
patent document 7: JP-A-2008-88120
patent document 8: WO2009/123194

SUMMARY OF THE INVENTION

Problems to be Solved by the Invention

There is a strong demand for the development of a compound having an MCH receptor antagonistic action and low toxicity, which is useful as an agent for the prophylaxis or treatment obesity and the like.

Means of Solving the Problems

The present inventors have conducted intensive studies of a compound having an MCH receptor antagonistic action and low toxicity (particularly, cardiotoxicity (e.g., human ether-a-go-go related gene (hERG) inhibitory activity), phospholipidosis (PLsis) inducing potential etc. often causing problems in drug discovery), and found that compound (I) to be explained below has a superior MCH receptor antagonistic action, as well as low toxicity such as cardiotoxicity (e.g., hERG inhibitory activity), PLsis-inducing potential and the like, as compared to conventional MCH receptor antagonists, which resulted in the completion of the present invention.

Accordingly, the present invention relates to [1] a compound represented by the formula (I):

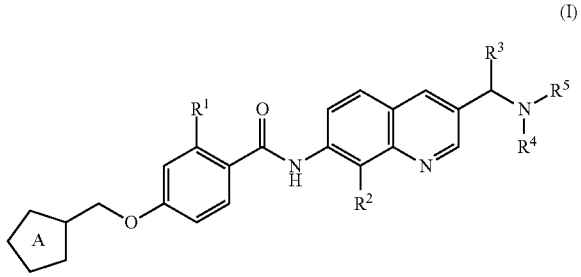

(I)

wherein
ring A is a tetrahydrofuran ring optionally further substituted;
$R^1$ is a hydrogen atom or a halogen atom;
$R^2$ is a hydrogen atom, a halogen atom or a $C_{1-6}$ alkyl group;
$R^3$ is a hydrogen atom or a $C_{1-6}$ alkyl group; and
$R^4$ and $R^5$
(1) are each independently a hydrogen atom, an optionally substituted $C_{1-6}$ alkyl group, an optionally substituted $C_{3-10}$ cycloalkyl group, or an optionally substituted 5- or 6-membered heterocyclic group, or
(2) may form, together with the adjacent nitrogen atom, substituted 4- to 6-membered nitrogen-containing heterocycle, provided that
when one of $R^4$ and $R^5$ is a hydrogen atom, then the other is not a group represented by the formula: —$X^1$—$R^{A1}$
wherein $X^1$ is a bond or a $C_{1-6}$ alkylene group; and
$R^{A1}$ is a group represented by the formula: —Y—S(O)$_{m1}$—$R^{B1}$ wherein Y is a bond or NH; m1 is an integer of 1 or 2; and $R^{B1}$ is a $C_{1-6}$ alkyl group optionally substituted by 1 to 3 halogen atoms, or a cyclic group represented by the formula:

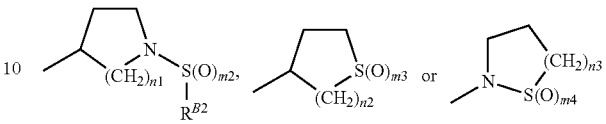

wherein m2, m3, m4, n1, n2 and n3 are each independently an integer of 1 or 2; and $R^{B2}$ is a $C_{1-6}$ alkyl group optionally substituted by 1 to 3 halogen atoms,
(the ring moiety of the cyclic group is optionally further substituted),
or a salt thereof (to be sometimes abbreviated as "compound (I)" in the present specification);
[2] the compound of the above-mentioned [1], wherein $R^1$ is a hydrogen atom or a fluorine atom;
[3] the compound of the above-mentioned [1], wherein $R^2$ is a fluorine atom or a methyl group;
[4] the compound of the above-mentioned [1], wherein $R^3$ is a hydrogen atom or a methyl group;
[5] the compound of the above-mentioned [1], wherein $R^4$ is
(a) a $C_{1-6}$ alkyl group optionally substituted by 1 to 3 substituents selected from a hydroxy group, a $C_{1-6}$ alkoxy group, and a 5- or 6-membered oxygen-containing heterocyclic group, or
(b) a $C_{3-10}$ cycloalkyl group optionally substituted by 1 to 3 substituents selected from a hydroxy group and a $C_{1-6}$ alkyl group; and
$R^5$ is a hydrogen atom;
[6] the compound of the above-mentioned [1], wherein $R^4$ and $R^5$ form, together with the adjacent nitrogen atom, 4- to 6-membered nitrogen-containing heterocycle substituted by hydroxyl group(s), and the nitrogen-containing heterocycle is optionally substituted by $C_{1-6}$ alkyl group(s);
[7] the compound of the above-mentioned [1], wherein ring A is a tetrahydrofuran ring;
$R^1$ is a hydrogen atom or a fluorine atom;
$R^2$ is a fluorine atom or a methyl group;
$R^3$ is a hydrogen atom or a methyl group;
$R^4$ is
(a) a $C_{1-6}$ alkyl group optionally substituted by 1 to 3 substituents selected from a hydroxy group, a $C_{1-6}$ alkoxy group, and a 5- or 6-membered oxygen-containing heterocyclic group, or
(b) a $C_{3-10}$ cycloalkyl group optionally substituted by 1 to 3 substituents selected from a hydroxy group and a $C_{1-6}$ alkyl group; and
$R^5$ is a hydrogen atom;
[8] the compound of the above-mentioned [1], wherein ring A is a tetrahydrofuran ring;
$R^1$ is a hydrogen atom or a fluorine atom;
$R^2$ is a fluorine atom or a methyl group;
$R^3$ is a hydrogen atom or a methyl group; and
$R^4$ and $R^5$ form, together with the adjacent nitrogen atom, 5- or 6-membered nitrogen-containing heterocycle substituted by hydroxyl group(s), and the nitrogen-containing heterocycle is optionally substituted by $C_{1-6}$ alkyl group(s);
[9] N-[8-methyl-3-({[(2S)-tetrahydrofuran-2-ylmethyl]amino}methyl)quinolin-7-yl]-4-[(2S)-tetrahydrofuran-2-ylmethoxy]benzamide or a salt thereof;

[10] N-{8-methyl-3-[(tetrahydro-2H-pyran-4-ylamino)methyl]quinolin-7-yl}-4-[(2S)-tetrahydrofuran-2-ylmethoxy]benzamide or a salt thereof;

[11] N-(8-methyl-3-{[(2-methylpropyl)amino]methyl}quinolin-7-yl)-4-[(2S)-tetrahydrofuran-2-ylmethoxy]benzamide or a salt thereof;

[12] N-(3-{[(trans-4-hydroxy-4-methylcyclohexyl)amino]methyl}-8-methylquinolin-7-yl)-4-[(2S)-tetrahydrofuran-2-ylmethoxy]benzamide or a salt thereof;

[13] N-{3-[(4-hydroxy-4-methylpiperidin-1-yl)methyl]-8-methylquinolin-7-yl}-4-[(2S)-tetrahydrofuran-2-ylmethoxy]benzamide or a salt thereof;

[14] a prodrug of the compound of the above-mentioned [1];

[15] a medicament comprising the compound of the above-mentioned [1] or a prodrug thereof;

[16] the medicament of the above-mentioned [15], which is a melanin-concentrating hormone receptor antagonist;

[17] the medicament of the above-mentioned [15], which is an anorexigenic agent;

[18] the medicament of the above-mentioned [15], which is a prophylactic or therapeutic agent for obesity;

[19] a method of preventing or treating obesity in a mammal, which comprises administering an effective amount of the compound of the above-mentioned [1] or a prodrug thereof to said mammal;

[20] use of the compound of the above-mentioned [1] or a prodrug thereof for the production of a prophylactic or therapeutic agent for obesity; and the like.

Effect of the Invention

Compound (I) has a high MCH receptor antagonistic action, and low toxicity such as cardiotoxicity (e.g., hERG inhibitory activity), PLsis inducing potential and the like, as compared to conventional MCH receptor antagonists. Therefore, compound (I) is highly useful as a safe agent for the prophylaxis or treatment of obesity and the like.

DETAILED DESCRIPTION OF THE INVENTION

The definition of each symbol in the formula (I) is explained in detail in the following.

The "halogen atom" in the present specification means, unless otherwise specified, a fluorine atom, a chlorine atom, a bromine atom or an iodine atom.

The "$C_{1-6}$ alkyl group" in the present specification means, unless otherwise specified, methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 1,2,2-trimethylpropyl, 3,3-dimethylbutyl, 2-ethylbutyl and the like.

In the present specification, the "$C_{3-10}$ cycloalkyl group" means, unless otherwise specified, cyclopropyl, cyclobutyl, cyclopentyl, cyclohexyl, cycloheptyl, cyclooctyl, adamantyl and the like.

The "$C_{1-6}$ alkoxy group" in the present specification means, unless otherwise specified, methoxy, ethoxy, propoxy, isopropoxy, butoxy, isobutoxy, sec-butoxy, tert-butoxy and the like. Of these, methoxy and isopropoxy are preferable.

Ring A is a tetrahydrofuran ring optionally further substituted.

The "tetrahydrofuran ring" of the "tetrahydrofuran ring optionally further substituted" for ring A may have, in addition to group —CH$_2$—O—, 1 to 4 substituents at substitutable positions. When the number of substituents is not less than 2, the respective substituents may be the same or different. Examples of such substituent include (1) a $C_{3-10}$ cycloalkyl group (e.g., cyclopropyl, cyclohexyl);

(2) a $C_{6-14}$ aryl group (e.g., phenyl, naphthyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;

(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;

(4) a nonaromatic heterocyclic group (e.g., tetrahydrofuryl, morpholinyl, thiomorpholinyl, piperidinyl, pyrrolidinyl, piperazinyl) optionally substituted by 1 to 3 substituents selected from
  (a) a $C_{1-6}$ alkyl group optionally substituted by 1 to 3 halogen atoms,
  (b) a hydroxy group,
  (c) a $C_{1-6}$ alkoxy group optionally substituted by 1 to 3 halogen atoms, and
  (d) a halogen atom;

(5) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 halogen atoms, and
  (c) a $C_{1-6}$ alkoxy-carbonyl group optionally substituted by 1 to 3 halogen atoms;

(6) a $C_{1-6}$ alkyl-carbonyl group optionally substituted by 1 to 3 halogen atoms;

(7) a $C_{1-6}$ alkoxy-carbonyl group optionally substituted by 1 to 3 substituents selected from
  (a) a halogen atom, and
  (b) a $C_{1-6}$ alkoxy group;

(8) a $C_{1-6}$ alkylsulfonyl group (e.g., methylsulfonyl, ethylsulfonyl, isopropylsulfonyl) optionally substituted by 1 to 3 halogen atoms;

(9) a carbamoyl group optionally mono- or di-substituted by $C_{1-6}$ alkyl group(s) optionally substituted by 1 to 3 halogen atoms;

(10) a thiocarbamoyl group optionally mono- or di-substituted by $C_{1-6}$ alkyl group(s) optionally substituted by 1 to 3 halogen atoms;

(11) a sulfamoyl group optionally mono- or di-substituted by $C_{1-6}$ alkyl group(s) optionally substituted by 1 to 3 halogen atoms;

(12) a carboxy group;

(13) a hydroxy group;

(14) a $C_{1-6}$ alkoxy group optionally substituted by 1 to 3 substituents selected from
  (a) a halogen atom,
  (b) a carboxy group,
  (c) a $C_{1-6}$ alkoxy group,
  (d) a $C_{1-6}$ alkoxy-carbonyl group, (e) an amino group optionally mono- or di-substituted by substituent (s) selected from a $C_{1-6}$ alkyl group and a $C_{1-6}$ alkoxy-carbonyl group,
(f) a $C_{6-14}$ aryl group (e.g., phenyl),
(g) a $C_{3-10}$ cycloalkyl group (e.g., cyclopropyl, cyclobutyl), and
(h) an aromatic heterocyclic group (e.g., thienyl, furyl);
(15) a $C_{2-6}$ alkenyloxy group (e.g., ethenyloxy) optionally substituted by 1 to 3 halogen atoms;
(16) a $C_{6-14}$ aryloxy group (e.g., phenyloxy, naphthyloxy);
(17) a $C_{1-6}$ alkyl-carbonyloxy group (e.g., acetyloxy, tert-butylcarbonyloxy);
(18) a $C_{6-14}$ aryl-carbonyl group (e.g., benzoyl) optionally substituted by 1 to 3 substituents selected from
    (a) a halogen atom, and
    (b) a $C_{1-6}$ alkyl group optionally substituted by 1 to 3 halogen atoms;
(19) a nonaromatic heterocyclylcarbonyl group (e.g., pyrrolidinylcarbonyl, morpholinylcarbonyl, 1,1-dioxide-thiomorpholinylcarbonyl) optionally substituted by 1 to 3 $C_{1-6}$ alkyl groups optionally substituted by 1 to 3 halogen atoms;
(20) a mercapto group;
(21) a $C_{1-6}$ alkylthio group (e.g., methylthio, ethylthio) optionally substituted by 1 to 3 halogen atoms;
(22) a $C_{7-13}$ aralkylthio group (e.g., benzylthio);
(23) a $C_{6-14}$ arylthio group (e.g., phenylthio, naphthylthio);
(24) a cyano group;
(25) a nitro group;
(26) a halogen atom;
(27) a $C_{1-3}$ alkylenedioxy group;
(28) an aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 $C_{1-6}$ alkyl groups optionally substituted by 1 to 3 halogen atoms;
(29) a hydroxyimino group optionally substituted by $C_{1-6}$ alkyl group(s) optionally substituted by 1 to 3 $C_{6-14}$ aryl groups (e.g., phenyl);
(30) a $C_{1-6}$ alkyl group optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group,
    (f) an amino group optionally mono- or di-substituted by $C_{1-6}$ alkyl group(s), and
    (g) a $C_{3-10}$ cycloalkyloxy group (preferably, cyclopropyloxy);
(31) a $C_{2-6}$ alkenyl group (e.g., ethenyl) optionally substituted by 1 to 3 substituents selected from
    (a) a halogen atom,
    (b) a carboxy group,
    (c) a hydroxy group,
    (d) a $C_{1-6}$ alkoxy-carbonyl group,
    (e) a $C_{1-6}$ alkoxy group,
    (f) an amino group optionally mono- or di-substituted by $C_{1-6}$ alkyl group(s), and
    (g) a $C_{3-10}$ cycloalkyl group (e.g., cyclopropyl);
(32) a $C_{2-6}$ alkynyl group (e.g., ethynyl) optionally substituted by 1 to 3 $C_{3-10}$ cycloalkyl groups (e.g., cyclopropyl, cyclobutyl);
(33) a $C_{7-13}$ aralkyl group (e.g., benzyl) optionally substituted by 1 to 3 substituents selected from
    (a) a $C_{1-6}$ alkyl group optionally substituted by 1 to 3 halogen atoms,
    (b) a hydroxy group,
    (c) a $C_{1-6}$ alkoxy group, and
    (d) a halogen atom;
(34) an oxo group;
and the like.

Ring A is preferably a tetrahydrofuran ring optionally further substituted by 1 to 3 substituents selected from
(1) a $C_{1-6}$ alkyl group;
(2) a $C_{1-6}$ alkoxy group;
(3) an oxo group;
and the like.

Ring A is more preferably a tetrahydrofuran ring.

$R^1$ is a hydrogen atom or a halogen atom (e.g., a fluorine atom).

$R^1$ is preferably a hydrogen atom or a fluorine atom.

$R^2$ is a hydrogen atom, a halogen atom (e.g., a fluorine atom) or a $C_{1-6}$ alkyl group (e.g., methyl group).

$R^2$ is preferably a fluorine atom or a methyl group.

$R^3$ is a hydrogen atom or a $C_{1-6}$ alkyl group (e.g., a methyl group).

$R^3$ is preferably a hydrogen atom or a methyl group.

$R^4$ and $R^5$
(1) are each independently a hydrogen atom, an optionally substituted $C_{1-6}$ alkyl group, an optionally substituted $C_{3-10}$ cycloalkyl group, or an optionally substituted 5- or 6-membered heterocyclic group, or
(2) may form, together with the adjacent nitrogen atom, substituted 4- to 6-membered nitrogen-containing heterocycle, provided that
when one of $R^4$ and $R^5$ is a hydrogen atom, then the other is not a group represented by the formula: $-X^1-R^{41}$
wherein
$X^1$ is a bond or a $C_{1-6}$ alkylene group; and
$R^{41}$ is a group represented by the formula: $-Y-S(O)_{m1}-R^{B1}$
wherein Y is a bond or NH; m1 is an integer of 1 or 2; and $R^{B1}$ is a $C_{1-6}$ alkyl group optionally substituted by 1 to 3 halogen atoms, or a cyclic group represented by the formula:

$$\underset{R^{B2}}{\overset{(CH_2)_{n1}}{\diagup}}\!\!\!\!\!N\!\!-\!\!S(O)_{m2}, \quad \underset{(CH_2)_{n2}}{\diagup}\!\!\!N\!\!-\!\!S(O)_{m3} \quad \text{or} \quad \underset{N}{\diagup}\!\!\!\overset{(CH_2)_{n3}}{\diagdown}\!\!\!S(O)_{m4}$$

wherein m2, m3, m4, n1, n2 and n3 are each independently an integer of 1 or 2; and $R^{B2}$ is a $C_{1-6}$ alkyl group optionally substituted by 1 to 3 halogen atoms, (the ring moiety of the cyclic group is optionally further substituted).

The "$C_{1-6}$ alkyl group" of the "optionally substituted $C_{1-6}$ alkyl group" for $R^4$ or $R^5$ is preferably methyl, ethyl, propyl, isopropyl, isobutyl, sec-butyl, neopentyl, 1-ethylpropyl, 1,2,2-trimethylpropyl and the like. More preferably, it is methyl, isobutyl or the like.

The "$C_{1-6}$ alkyl group" of the "optionally substituted $C_{1-6}$ alkyl group" for $R^4$ or $R^5$ optionally has 1 to 5 (preferably, 1 to 3) substituent(s) at substitutable position(s). Examples of such substituent include those similar to (1)-(29) exemplified as the substituents optionally possessed by the "tetrahydrofuran ring" of the "optionally further substituted tetrahydrofuran ring" for ring A. When the number of the substituents is two or more, the respective substituents may be the same or different.

The substituent of the "optionally substituted $C_{1-6}$ alkyl group" for $R^4$ or $R^5$ is preferably a halogen atom, a hydroxy group, a $C_{1-6}$ alkoxy group, a $C_{3-10}$ cycloalkyl group, an aromatic heterocyclic group, a nonaromatic heterocyclic group and the like. More preferably, it is a hydroxy group, a $C_{1-6}$ alkoxy group (e.g., methoxy, isopropoxy) or a 5- or 6-membered oxygen-containing heterocyclic group (e.g., tetrahydrofuryl, tetrahydropyranyl).

Examples of the "5- or 6-membered oxygen-containing heterocyclic group" as a substituent of the "optionally substituted $C_{1-6}$ alkyl group" for $R^4$ or $R^5$ include a 5- or 6-membered oxygen-containing heterocyclic group containing at least one oxygen atom as a ring-constituting atom besides carbon atom and optionally further containing 1 to 3 hetero atoms selected from oxygen atom, sulfur atom and nitrogen atom.

Specific examples of the "5- or 6-membered oxygen-containing heterocyclic group" include furyl (e.g., 2-furyl, 3-furyl), oxazolyl (e.g., 2-oxazolyl, 4-oxazolyl, 5-oxazolyl), isoxazolyl, oxadiazolyl (e.g., 1,2,4-oxadiazol-5-yl, 1,3,4-oxadiazol-2-yl), tetrahydrofuryl (e.g., 2-tetrahydrofuryl, 3-tetrahydrofuryl), pyranyl (e.g., 2H-pyranyl), tetrahydropyranyl (e.g., 4-tetrahydropyranyl), morpholinyl (e.g., morpholino), oxazolinyl (e.g., 2,5-dihydrooxazol-3-yl, 3,4-dihydrooxazol-3-yl), oxazolidinyl (e.g., oxazolidin-3-yl), dihydrooxadiazolyl (e.g., 4,5-dihydro-1,2,4-oxadiazol-3-yl) and the like. More preferred are tetrahydrofuryl, tetrahydropyranyl and the like.

The "optionally substituted $C_{1-6}$ alkyl group" for $R^4$ or $R^5$ is preferably a $C_{1-6}$ alkyl group (e.g., methyl, ethyl, propyl, isopropyl, butyl, isobutyl, sec-butyl, tert-butyl, pentyl, neopentyl, 1-ethylpropyl, 1,2,2-trimethylpropyl) optionally substituted by 1 to 3 substituents selected from
(1) a halogen atom (e.g., a fluorine atom);
(2) a hydroxy group;
(3) a $C_{1-6}$ alkoxy group (e.g., methoxy, isopropoxy);
(4) a $C_{3-10}$ cycloalkyl group (e.g., cyclopropyl, cyclohexyl) optionally substituted by 1 to 3 substituents selected from a hydroxy group and a $C_{1-6}$ alkyl group;
(5) a 4- to 6-membered oxygen-containing heterocyclic group (e.g., oxetanyl, tetrahydrofuryl, tetrahydropyranyl) optionally substituted by $C_{1-6}$ alkyl group(s) (e.g., methyl);
(6) an amino group optionally mono- or di-substituted by substituent(s) selected from
　(a) a $C_{1-6}$ alkyl group optionally substituted by 1 to 3 halogen atoms,
　(b) a $C_{1-6}$ alkyl-carbonyl group (e.g., methylcarbonyl, ethylcarbonyl) optionally substituted by 1 to 3 halogen atoms,
　(c) a $C_{1-6}$ alkoxy-carbonyl group (e.g., methoxycarbonyl, ethoxycarbonyl) optionally substituted by 1 to 3 halogen atoms,
　(d) a carbamoyl group optionally mono- or di-substituted by $C_{1-6}$ alkyl group(s) (e.g., methylcarbamoyl, ethylcarbamoyl) optionally substituted by 1 to 3 halogen atoms, and
　(e) a formyl group;
(7) a $C_{1-6}$ alkyl-carbonyl group optionally substituted by 1 to 3 halogen atoms; and the like, and the like.

The "optionally substituted $C_{1-6}$ alkyl group" for $R^4$ or $R^5$ is more preferably a $C_{1-6}$ alkyl group (e.g., methyl, ethyl, propyl, isopropyl, butyl, isobutyl, sec-butyl, tert-butyl, pentyl, neopentyl, 1-ethylpropyl, 1,2,2-trimethylpropyl) optionally substituted by 1 to 3 substituents selected from
(1) a halogen atom (e.g., a fluorine atom);
(2) a hydroxy group;
(3) a $C_{1-6}$ alkoxy group (e.g., methoxy, isopropoxy);
(4) a $C_{3-10}$ cycloalkyl group (e.g., cyclopropyl, cyclohexyl) optionally substituted by 1 to 3 substituents selected from a hydroxy group and a $C_{1-6}$ alkyl group;
(5) a 4- to 6-membered oxygen-containing heterocyclic group (e.g., oxetanyl, tetrahydrofuryl, tetrahydropyranyl) optionally substituted by a $C_{1-6}$ alkyl group (e.g., methyl); and the like, and the like.

The "$C_{3-10}$ cycloalkyl group" of the "optionally substituted $C_{3-10}$ cycloalkyl group" for $R^4$ or $R^5$ is preferably cyclopropyl, cyclobutyl, cyclopentyl, cyclohexyl, adamantyl and the like. More preferred are cyclohexyl and the like.

The substituent of the "$C_{3-10}$ cycloalkyl group" of the "optionally substituted $C_{3-10}$ cycloalkyl group" for $R^4$ or $R^5$ includes those similar to the substituents optionally possessed by the "tetrahydrofuran ring" of the "optionally further substituted tetrahydrofuran ring" for ring A. The substituent of the "$C_{3-10}$ cycloalkyl group" is preferably a halogen atom, a hydroxy group, a $C_{1-6}$ alkyl group, a $C_{1-6}$ alkoxy group and the like. More preferred are a hydroxy group, a methyl group and the like.

The "$C_{1-6}$ cycloalkyl group" may have 1 to 5, preferably 1 to 3, more preferably 1 or 2, substituents at substitutable position(s). When the number of the substituents is two or more, the respective substituents may be the same or different.

The "optionally substituted $C_{3-10}$ cycloalkyl group" for $R^4$ or $R^5$ is preferably a $C_{3-10}$ cycloalkyl group (e.g., cyclopropyl, cyclobutyl, cyclopentyl, cyclohexyl, adamantyl) optionally substituted by 1 to 3 substituents selected from
(1) a halogen atom (e.g., a fluorine atom);
(2) a hydroxy group;
(3) a $C_{1-6}$ alkoxy group (e.g., methoxy, isopropoxy);
(4) a $C_{1-6}$ alkyl group (e.g., methyl);
(5) an amino group optionally mono- or di-substituted by substituent(s) selected from
　(a) a $C_{1-6}$ alkyl group optionally substituted by 1 to 3 halogen atoms,
　(b) a $C_{1-6}$ alkyl-carbonyl group (e.g., methylcarbonyl, ethylcarbonyl) optionally substituted by 1 to 3 halogen atoms,
　(c) a $C_{1-6}$ alkoxy-carbonyl group (e.g., methoxycarbonyl, ethoxycarbonyl) optionally substituted by 1 to 3 halogen atoms,
　(d) a carbamoyl group optionally mono- or di-substituted by $C_{1-6}$ alkyl group(s) (e.g., methylcarbamoyl, ethylcarbamoyl) optionally substituted by 1 to 3 halogen atoms, and
　(e) a formyl group;
(6) an oxo group;
and the like, and the like.

The "optionally substituted $C_{3-10}$ cycloalkyl group" for $R^4$ or $R^5$ is more preferably a $C_{3-10}$ cycloalkyl group (e.g., cyclopropyl, cyclobutyl, cyclopentyl, cyclohexyl, adamantyl) optionally substituted by 1 to 3 substituents selected from
(1) a hydroxy group;
(2) a $C_{1-6}$ alkyl group (e.g., methyl);
and the like, and the like.

The "5- or 6-membered heterocyclic group" of the "optionally substituted 5- or 6-membered heterocyclic group" for $R^4$ or $R^5$ is 5- or 6-membered aromatic heterocyclic group, a 5- or 6-membered nonaromatic heterocyclic group and the like.

Examples of the "5- or 6-membered aromatic heterocyclic group" include a 5- or 6-membered aromatic heterocyclic group containing, as a ring-constituting atom besides carbon atom, 1 to 4 hetero atoms selected from oxygen atom, sulfur atom (which may be oxidized) and nitrogen atom, and the like.

Specific examples of the 5- or 6-membered aromatic heterocyclic group include furyl (e.g., 2-furyl, 3-furyl), thienyl (e.g., 2-thienyl, 3-thienyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl, 4-pyridazinyl), pyrazinyl (e.g., 2-pyrazinyl), pyrrolyl (e.g., 1-pyrrolyl, 2-pyrrolyl, 3-pyrrolyl), imidazolyl (e.g., 1-imidazolyl, 2-imidazolyl, 4-imidazolyl, 5-imidazolyl), pyrazolyl (e.g., 1-pyrazolyl, 3-pyrazolyl, 4-pyrazolyl), thiazolyl (e.g., 2-thiazolyl, 4-thiazolyl, 5-thiazolyl), isothiazolyl (e.g., 4-isothiazolyl), oxazolyl (e.g., 2-oxazolyl, 4-oxazolyl, 5-oxazolyl), isoxazolyl, oxadiazolyl (e.g., 1,2,4-oxadiazol-5-yl, 1,3,4-oxadiazol-2-yl), thiadiazolyl (e.g., 1,3,4-thiadiazol-2-yl), triazolyl (e.g., 1,2,4-triazol-1-yl, 1,2,4-triazol-3-yl, 1,2,3-triazol-1-yl, 1,2,3-triazol-2-yl, 1,2,3-triazol-4-yl), tetrazolyl (e.g., tetrazol-1-yl, tetrazol-5-yl), triazinyl (e.g., 1,2,4-triazin-1-yl, 1,2,4-triazin-3-yl, 1,3,5-triazin-1-yl) and the like.

Examples of the "5- or 6-membered nonaromatic heterocyclic group" include 5- or 6-membered nonaromatic heterocyclic group containing, as a ring-constituting atom besides carbon atom, 1 to 4 hetero atoms selected from oxygen atom, sulfur atom (which may be oxidized) and nitrogen atom, and the like.

Specific examples of the 5- or 6-membered nonaromatic heterocyclic group include tetrahydrofuryl (e.g., 2-tetrahydrofuryl), dihydropyrrolyl (e.g., 2,3-dihydro-1H-pyrrol-1-yl), pyrrolidinyl (e.g., 1-pyrrolidinyl), 1,1-dioxide-tetrahydrothienyl (e.g., 1,1-dioxide-tetrahydro-3-thienyl), piperidinyl (e.g., piperidino), morpholinyl (e.g., morpholino), thiomorpholinyl (e.g., thiomorpholino), 1,1-dioxide-thiomorpholinyl (e.g., 1,1-dioxide-thiomorpholino), piperazinyl (e.g., 1-piperazinyl), hexamethyleneiminyl (e.g., hexamethylenimin-1-yl), oxazolinyl (e.g., 2,5-dihydrooxazol-3-yl, 3,4-dihydrooxazol-3-yl), thiazolinyl (e.g., 2,5-dihydrothiazol-3-yl, 3,4-dihydrothiazol-3-yl), imidazolinyl (e.g., 2-imidazolin-3-yl), oxazolidinyl (e.g., oxazolidin-3-yl), thiazolidinyl (e.g., thiazolidin-3-yl), imidazolidinyl (e.g., imidazolidin-3-yl), dioxolyl (e.g., 1,3-dioxol-4-yl), dioxolanyl (e.g., 1,3-dioxolan-4-yl), dihydrooxadiazolyl (e.g., 4,5-dihydro-1,2,4-oxadiazol-3-yl), thioxooxazolidinyl (e.g., 2-thioxo-1,3-oxazolidin-5-yl), tetrahydropyranyl (e.g., 4-tetrahydropyranyl), tetrahydrothiopyranyl (e.g., 4-tetrahydrothiopyranyl), 1,1-dioxide-tetrahydrothiopyranyl (e.g., 1,1-dioxide-tetrahydrothiopyran-4-yl), pyrazolinyl (e.g., pyrazolin-3-yl), pyrazolidinyl (e.g., pyrazolidin-1-yl), oxotetrahydropyridazinyl (e.g., 3-oxo-2,3,4,5-tetrahydropyridazin-4-yl) and the like.

The "5- or 6-membered heterocyclic group" of the "optionally substituted 5- or 6-membered heterocyclic group" for $R^4$ or $R^5$ is preferably tetrahydrofuryl, tetrahydropyranyl or the like.

The substituent of the "5- or 6-membered heterocyclic group" of the "optionally substituted 5- or 6-membered heterocyclic group" for $R^4$ or $R^5$ includes those similar to the substituents optionally possessed by the "tetrahydrofuran ring" of the "optionally further substituted tetrahydrofuran ring" for ring A. The substituent of the "5- or 6-membered heterocyclic group" is preferably a halogen atom, a hydroxy group, a $C_{1-6}$ alkyl group, a $C_{1-6}$ alkoxy group and the like. More preferred are a hydroxy group, a methyl group and the like.

The "5- or 6-membered heterocyclic group" may have 1 to 5 (preferably 1 or 2) substituents at substitutable position(s). When the number of the substituents is two or more, the respective substituents may be the same or different.

The "optionally substituted 5- or 6-membered heterocyclic group" for $R^4$ or $R^5$ is preferably a 5- or 6-membered heterocyclic group (e.g., tetrahydrofuryl, tetrahydropyranyl) optionally substituted by 1 to 3 substituents selected from (1) a halogen atom;
(2) a hydroxy group;
(3) a $C_{1-6}$ alkyl group (e.g., methyl);
(4) a $C_{1-6}$ alkoxy group;
and the like, and the like.

The "optionally substituted 5- or 6-membered heterocyclic group" for $R^4$ or $R^5$ is more preferably a 5- or 6-membered heterocyclic group (e.g., tetrahydrofuryl, tetrahydropyranyl) or the like.

Examples of the "4- to 6-membered nitrogen-containing heterocycle" of the "substituted 4- to 6-membered nitrogen-containing heterocycle" formed by $R^4$ and $R^5$ together with the adjacent nitrogen atom include 4- to 6-membered nitrogen-containing heterocycle containing, as a ring-constituting atom besides carbon atom, at least one nitrogen atom, and optionally further containing 1 to 3 hetero atoms selected from oxygen atom, sulfur atom and nitrogen atom.

Specific examples of the "4- to 6-membered nitrogen-containing heterocycle" include pyrrolidine, imidazoline, imidazolidine, pyrazolidine, pyrazoline, piperidine, piperazine, triazoline, pyrrole, pyrazole, imidazole, triazole, azepine, dihydropyrrole, dihydropyrazole, dihydroimidazole, dihydrothiazole, tetrahydropyridine and the like. Preferred are pyrrolidine, piperidine, piperazine and the like.

Examples of the substituent of the "4- to 6-membered nitrogen-containing heterocycle" of the "substituted 4- to 6-membered nitrogen-containing heterocycle" formed by $R^4$ and $R^5$ together with the adjacent nitrogen atom include those similar to the substituents optionally possessed by the "tetrahydrofuran ring" of the "optionally further substituted tetrahydrofuran ring" for ring A. The substituent of the "4- to 6-membered nitrogen-containing heterocycle" is preferably a halogen atom, a hydroxy group, a $C_{1-6}$ alkyl group, a $C_{1-6}$ alkoxy group and the like. More preferred are a hydroxy group, a methyl group and the like.

The "4- to 6-membered nitrogen-containing heterocycle" may have 1 to 5 (preferably 1 or 2) substituents at substitutable position(s). When the number of the substituents is two or more, the respective substituents may be the same or different.

The "substituted 4- to 6-membered nitrogen-containing heterocycle" formed by $R^4$ and $R^5$ together with the adjacent nitrogen atom is preferably 4- to 6-membered nitrogen-containing heterocycle (e.g., pyrrolidine, piperidine, piperazine) optionally substituted by 1 to 3 substituents selected from
(1) a halogen atom;
(2) a hydroxy group;
(3) a $C_{1-6}$ alkyl group (e.g., methyl);
(4) a $C_{1-6}$ alkoxy group;
(5) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group (e.g., methylcarbonyl, ethylcarbonyl) optionally substituted by 1 to 3 halogen atoms,
  (c) a $C_{1-6}$ alkoxy-carbonyl group (e.g., methoxycarbonyl, ethoxycarbonyl) optionally substituted by 1 to 3 halogen atoms,
  (d) a carbamoyl group optionally mono- or di-substituted by $C_{1-6}$ alkyl group(s) (e.g., methylcarbamoyl, ethylcarbamoyl) optionally substituted by 1 to 3 halogen atoms, and
  (e) a formyl group;
(6) an oxo group;
and the like, and the like.

The "substituted 4- to 6-membered nitrogen-containing heterocycle" formed by $R^4$ and $R^5$ together with the adjacent nitrogen atom is more preferably 4- to 6-membered nitrogen-containing heterocycle substituted by hydroxyl group(s) (preferably, 5- or 6-membered nitrogen-containing heterocycle (e.g., piperidine) substituted by hydroxyl group(s)), which is optionally substituted by $C_{1-6}$ alkyl group(s) (e.g., methyl) or the like.

Preferably,
1) $R^4$ and $R^5$ are each independently
(1) a hydrogen atom,
(2) a $C_{1-6}$ alkyl group (e.g., methyl, ethyl, propyl, isopropyl, butyl, isobutyl, sec-butyl, tert-butyl, pentyl, neopentyl, 1-ethylpropyl, 1,2,2-trimethylpropyl) optionally substituted by 1 to 3 substituents selected from
    (a) a halogen atom (e.g., a fluorine atom),
    (b) a hydroxy group,
    (c) a $C_{1-6}$ alkoxy group (e.g., methoxy, isopropoxy),
    (d) a $C_{3-10}$ cycloalkyl group (e.g., cyclopropyl, cyclohexyl) optionally substituted by 1 to 3 substituents selected from a hydroxy group and a $C_{1-6}$ alkyl group,
    (e) a 4- to 6-membered oxygen-containing heterocyclic group (e.g., oxetanyl, tetrahydrofuryl, tetrahydropyranyl) optionally substituted by $C_{1-6}$ alkyl group(s) (e.g., methyl),
    (f) an amino group optionally mono- or di-substituted by substituent(s) selected from
        (i) a $C_{1-6}$ alkyl group optionally substituted by 1 to 3 halogen atoms,
        (ii) a $C_{1-6}$ alkyl-carbonyl group (e.g., methylcarbonyl, ethylcarbonyl) optionally substituted by 1 to 3 halogen atoms,
        (iii) a $C_{1-6}$ alkoxy-carbonyl group (e.g., methoxycarbonyl, ethoxycarbonyl) optionally substituted by 1 to 3 halogen atoms,
        (iv) a carbamoyl group optionally mono- or di-substituted by $C_{1-6}$ alkyl group(s) (e.g., methylcarbamoyl, ethylcarbamoyl) optionally substituted by 1 to 3 halogen atoms, and
        (v) a formyl group, and
    (g) a $C_{1-6}$ alkyl-carbonyl group optionally substituted by 1 to 3 halogen atoms,
(3) a $C_{3-10}$ cycloalkyl group (e.g., cyclopropyl, cyclobutyl, cyclopentyl, cyclohexyl, adamantyl) optionally substituted by 1 to 3 substituents selected from
    (a) a halogen atom (e.g., a fluorine atom),
    (b) a hydroxy group,
    (c) a $C_{1-6}$ alkoxy group (e.g., methoxy, isopropoxy),
    (d) a $C_{1-6}$ alkyl group (e.g., methyl),
    (e) an amino group optionally mono- or di-substituted by substituent(s) selected from
        (i) a $C_{1-6}$ alkyl group optionally substituted by 1 to 3 halogen atoms,
        (ii) a $C_{1-6}$ alkyl-carbonyl group (e.g., methylcarbonyl, ethylcarbonyl) optionally substituted by 1 to 3 halogen atoms,
        (iii) a $C_{1-6}$ alkoxy-carbonyl group (e.g., methoxycarbonyl, ethoxycarbonyl) optionally substituted by 1 to 3 halogen atoms,
        (iv) a carbamoyl group optionally mono- or di-substituted by $C_{1-6}$ alkyl group(s) (e.g., methylcarbamoyl, ethylcarbamoyl) optionally substituted by 1 to 3 halogen atoms, and
        (v) a formyl group, and
    (f) an oxo group,
(4) a 5- or 6-membered heterocyclic group (e.g., tetrahydrofuryl, tetrahydropyranyl) each optionally substituted by 1 to 3 substituents selected from
    (a) a halogen atom,
    (b) a hydroxy group,
    (c) a $C_{1-6}$ alkyl group (e.g., methyl), and
    (d) a $C_{1-6}$ alkoxy group,
and the like, or
2) $R^4$ and $R^5$ form, together with the adjacent nitrogen atom, 4- to 6-membered nitrogen-containing heterocycle (e.g., pyrrolidine, piperidine, piperazine) optionally substituted by 1 to 3 substituents selected from
(1) a halogen atom,
(2) a hydroxy group,
(3) a $C_{1-6}$ alkyl group (e.g., methyl),
(4) a $C_{1-6}$ alkoxy group,
(5) an amino group optionally mono- or di-substituted by substituent(s) selected from
    (a) a $C_{1-6}$ alkyl group optionally substituted by 1 to 3 halogen atoms,
    (b) a $C_{1-6}$ alkyl-carbonyl group (e.g., methylcarbonyl, ethylcarbonyl) optionally substituted by 1 to 3 halogen atoms,
    (c) a $C_{1-6}$ alkoxy-carbonyl group (e.g., methoxycarbonyl, ethoxycarbonyl) optionally substituted by 1 to 3 halogen atoms,
    (d) a carbamoyl group optionally mono- or di-substituted by $C_{1-6}$ alkyl group(s) (e.g., methylcarbamoyl, ethylcarbamoyl) optionally substituted by 1 to 3 halogen atoms, and
    (e) a formyl group, and
(6) an oxo group
and the like.

More preferably,
1) $R^4$ and $R^5$ are each independently
(1) a hydrogen atom,
(2) a $C_{1-6}$ alkyl group (e.g., methyl, ethyl, propyl, isopropyl, butyl, isobutyl, sec-butyl, tert-butyl, pentyl, neopentyl, 1-ethylpropyl, 1,2,2-trimethylpropyl) optionally substituted by 1 to 3 substituents selected from
    (a) a halogen atom (e.g., a fluorine atom),
    (b) a hydroxy group,
    (c) a $C_{1-6}$ alkoxy group (e.g., methoxy, isopropoxy),
    (d) a $C_{3-10}$ cycloalkyl group (e.g., cyclopropyl, cyclohexyl) optionally substituted by 1 to 3 substituents selected from a hydroxy group and a $C_{1-6}$ alkyl group, and
    (e) a 4- to 6-membered oxygen-containing heterocyclic group (e.g., oxetanyl, tetrahydrofuryl, tetrahydropyranyl) optionally substituted by $C_{1-6}$ alkyl group(s) (e.g., methyl),
(3) a $C_{3-10}$ cycloalkyl group (e.g., cyclopropyl, cyclobutyl, cyclopentyl, cyclohexyl, adamantyl) optionally substituted by 1 to 3 substituents selected from
    (a) a hydroxy group and
    (b) a $C_{1-6}$ alkyl group (e.g., methyl),
(4) a 5- or 6-membered heterocyclic group (e.g., tetrahydrofuryl, tetrahydropyranyl) optionally substituted by 1 to 3 substituents selected from
    (i) a hydroxy group, and
    (ii) a $C_{1-6}$ alkyl group (e.g., methyl)
and the like, or
2) $R^4$ and $R^5$ form, together with the adjacent nitrogen atom, 4- to 6-membered nitrogen-containing heterocycle substituted by hydroxy group(s) (preferably, 5- or 6-membered nitrogen-containing heterocycle (e.g., piperidine) substituted by hydroxy group(s)), which is optionally substituted by $C_{1-6}$ alkyl group(s) (e.g., methyl) and the like.

Further preferably,
$R^4$ is
(1) a $C_{1-6}$ alkyl group (e.g., methyl, ethyl, propyl, isopropyl, butyl, isobutyl, sec-butyl, tert-butyl, pentyl, neopentyl, 1-ethylpropyl, 1,2,2-trimethylpropyl) optionally substituted by 1 to 3 substituents selected from
- (i) a halogen atom (e.g., a fluorine atom),
- (ii) a hydroxy group,
- (iii) a $C_{1-6}$ alkoxy group (e.g., methoxy, isopropoxy),
- (iv) a $C_{3-10}$ cycloalkyl group (e.g., cyclopropyl, cyclohexyl) optionally substituted by 1 to 3 substituents selected from a hydroxy group and a $C_{1-6}$ alkyl group, and
- (v) a 4- to 6-membered oxygen-containing heterocyclic group (e.g., oxetanyl, tetrahydrofuryl, tetrahydropyranyl) optionally substituted by $C_{1-6}$ alkyl group(s) (e.g., methyl), (2) a $C_{3-10}$ cycloalkyl group (e.g., cyclopropyl, cyclobutyl, cyclopentyl, cyclohexyl, adamantyl) optionally substituted by 1 to 3 substituents selected from
- (i) a hydroxy group, and
- (ii) a $C_{1-6}$ alkyl group (e.g., methyl), or (3) a 5- or 6-membered heterocyclic group (e.g., tetrahydrofuryl, tetrahydropyranyl) optionally substituted by 1 to 3 substituents selected from
- (i) a hydroxy group, and
- (ii) a $C_{1-6}$ alkyl group (e.g., methyl); and $R^5$ is a hydrogen atom.

Particularly preferably, $R^4$ is (1) a $C_{1-6}$ alkyl group (e.g., methyl, ethyl, propyl, isopropyl, butyl, isobutyl, sec-butyl, tert-butyl, pentyl, neopentyl, 1-ethylpropyl, 1,2,2-trimethylpropyl) optionally substituted by 1 to 3 substituents selected from
- (a) a hydroxy group,
- (b) a $C_{1-6}$ alkoxy group (e.g., methoxy, isopropoxy), and
- (c) a 5- or 6-membered oxygen-containing heterocyclic group (e.g., tetrahydrofuryl, tetrahydropyranyl), or (2) a $C_{3-10}$ cycloalkyl group (e.g., cyclopropyl, cyclobutyl, cyclopentyl, cyclohexyl, adamantyl) optionally substituted by 1 to 3 substituents selected from
- (a) a hydroxy group, and
- (b) a $C_{1-6}$ alkyl group (e.g., methyl); and $R^5$ is a hydrogen atom.

In addition, in another more preferable embodiment of $R^4$ and $R^5$, $R^4$ and $R^5$ form, together with the adjacent nitrogen atom, 4- to 6-membered nitrogen-containing heterocycle substituted by hydroxy group(s) (preferably, 5- or 6-membered nitrogen-containing heterocycle substituted by hydroxy group(s) (e.g., piperidine)), which is optionally substituted by $C_{1-6}$ alkyl group(s) (e.g., methyl).

As compound (I), the following compounds are preferable.

[Compound A1]

Compound (I) wherein ring A is a tetrahydrofuran ring optionally further substituted by 1 to 3 substituents selected from
(1) a $C_{1-6}$ alkyl group,
(2) a $C_{1-6}$ alkoxy group, and
(3) an oxo group;

$R^1$ is a hydrogen atom or a halogen atom;
$R^2$ is a hydrogen atom, a halogen atom or a $C_{1-6}$ alkyl group;
$R^3$ is a hydrogen atom or a $C_{1-6}$ alkyl group; and
$R^4$ and $R^5$ are
1) each independently
(1) a hydrogen atom,
(2) a $C_{1-6}$ alkyl group (e.g., methyl, ethyl, propyl, isopropyl, butyl, isobutyl, sec-butyl, tert-butyl, pentyl, neopentyl, 1-ethylpropyl, 1,2,2-trimethylpropyl) optionally substituted by 1 to 3 substituents selected from
- (a) a halogen atom (e.g., a fluorine atom),
- (b) a hydroxy group,
- (c) a $C_{1-6}$ alkoxy group (e.g., methoxy, isopropoxy),
- (d) a $C_{3-10}$ cycloalkyl group (e.g., cyclopropyl, cyclohexyl) optionally substituted by 1 to 3 substituents selected from a hydroxy group and a $C_{1-6}$ alkyl group,
- (e) a 4- to 6-membered oxygen-containing heterocyclic group (e.g., oxetanyl, tetrahydrofuryl, tetrahydropyranyl) optionally substituted by $C_{1-6}$ alkyl group(s) (e.g., methyl),
- (f) an amino group optionally mono- or di-substituted by substituent(s) selected from
  - (i) a $C_{1-6}$ alkyl group optionally substituted by 1 to 3 halogen atoms,
  - (ii) a $C_{1-6}$ alkyl-carbonyl group (e.g., methylcarbonyl, ethylcarbonyl) optionally substituted by 1 to 3 halogen atoms,
  - (iii) a $C_{1-6}$ alkoxy-carbonyl group (e.g., methoxycarbonyl, ethoxycarbonyl) optionally substituted by 1 to 3 halogen atoms,
  - (iv) a carbamoyl group optionally mono- or di-substituted by $C_{1-6}$ alkyl group(s) (e.g., methylcarbamoyl, ethylcarbamoyl) optionally substituted by 1 to 3 halogen atoms, and
  - (v) a formyl group, and
- (g) a $C_{1-6}$ alkyl-carbonyl group optionally substituted by 1 to 3 halogen atoms, (3) a $C_{3-10}$ cycloalkyl group (e.g., cyclopropyl, cyclobutyl, cyclopentyl, cyclohexyl, adamantyl) optionally substituted by 1 to 3 substituents selected from
- (a) a halogen atom (e.g., a fluorine atom),
- (b) a hydroxy group,
- (c) a $C_{1-6}$ alkoxy group (e.g., methoxy, isopropoxy),
- (d) a $C_{1-6}$ alkyl group (e.g., methyl),
- (e) an amino group optionally mono- or di-substituted by substituent(s) selected from
  - (i) a $C_{1-6}$ alkyl group optionally substituted by 1 to 3 halogen atoms,
  - (ii) a $C_{1-6}$ alkyl-carbonyl group (e.g., methylcarbonyl, ethylcarbonyl) optionally substituted by 1 to 3 halogen atoms,
  - (iii) a $C_{1-6}$ alkoxy-carbonyl group (e.g., methoxycarbonyl, ethoxycarbonyl) optionally substituted by 1 to 3 halogen atoms,
  - (iv) a carbamoyl group optionally mono- or di-substituted by $C_{1-6}$ alkyl group(s) (e.g., methylcarbamoyl, ethylcarbamoyl) optionally substituted by 1 to 3 halogen atoms, and
  - (v) a formyl group, and
- (f) an oxo group, or (4) a 5- or 6-membered heterocyclic group (e.g., tetrahydrofuryl, tetrahydropyranyl) each optionally substituted by 1 to 3 substituents selected from
- (a) a halogen atom,
- (b) a hydroxy group,
- (c) a $C_{1-6}$ alkyl group (e.g., methyl), and
- (d) a $C_{1-6}$ alkoxy group, or 2) $R^4$ and $R^5$ form, together with the adjacent nitrogen atom, 4- to 6-membered nitrogen-containing heterocycle (e.g., pyrrolidine, piperidine, piperazine) substituted by 1 to 3 substituents selected from
(1) a halogen atom;
(2) a hydroxy group;
(3) a $C_{1-6}$ alkyl group (e.g., methyl);
(4) a $C_{1-6}$ alkoxy group;
(5) an amino group optionally mono- or di-substituted by substituent(s) selected from (a) a $C_{1-6}$ alkyl group optionally substituted by 1 to 3 halogen atoms,
(b) a $C_{1-6}$ alkyl-carbonyl group (e.g., methylcarbonyl, ethylcarbonyl) optionally substituted by 1 to 3 halogen atoms,
(c) a $C_{1-6}$ alkoxy-carbonyl group (e.g., methoxycarbonyl, ethoxycarbonyl) optionally substituted by 1 to 3 halogen atoms,
(d) a carbamoyl group optionally mono- or di-substituted by $C_{1-6}$ alkyl group(s) (e.g., methylcarbamoyl, ethylcarbamoyl) optionally substituted by 1 to 3 halogen atoms, and
(e) a formyl group, and
(6) an oxo group.

[Compound A2]
Compound (I) wherein
ring A is a tetrahydrofuran ring;
$R^1$ is a hydrogen atom or a halogen atom;
$R^2$ is a hydrogen atom, a halogen atom or a $C_{1-6}$ alkyl group;
$R^3$ is a hydrogen atom or a $C_{1-6}$ alkyl group; and
$R^4$ and $R^5$ are
1) each independently
(1) a hydrogen atom,
(2) a $C_{1-6}$ alkyl group (e.g., methyl, ethyl, propyl, isopropyl, butyl, isobutyl, sec-butyl, tert-butyl, pentyl, neopentyl, 1-ethylpropyl, 1,2,2-trimethylpropyl) optionally substituted by 1 to 3 substituents selected from
  (a) a halogen atom (e.g., a fluorine atom),
  (b) a hydroxy group,
  (c) a $C_{1-6}$ alkoxy group (e.g., methoxy, isopropoxy),
  (d) a $C_{3-10}$ cycloalkyl group (e.g., cyclopropyl, cyclohexyl) optionally substituted by 1 to 3 substituents selected from a hydroxy group and a $C_{1-6}$ alkyl group,
  (e) a 4- to 6-membered oxygen-containing heterocyclic group (e.g., oxetanyl, tetrahydrofuryl, tetrahydropyranyl) optionally substituted by $C_{1-6}$ alkyl group(s) (e.g., methyl),
  (f) an amino group optionally mono- or di-substituted by substituent(s) selected from
    (i) a $C_{1-6}$ alkyl group optionally substituted by 1 to 3 halogen atoms,
    (ii) a $C_{1-6}$ alkyl-carbonyl group (e.g., methylcarbonyl, ethylcarbonyl) optionally substituted by 1 to 3 halogen atoms,
    (iii) a $C_{1-6}$ alkoxy-carbonyl group (e.g., methoxycarbonyl, ethoxycarbonyl) optionally substituted by 1 to 3 halogen atoms,
    (iv) a carbamoyl group optionally mono- or di-substituted by $C_{1-6}$ alkyl group(s) (e.g., methylcarbamoyl, ethylcarbamoyl) optionally substituted by 1 to 3 halogen atoms, and
    (v) a formyl group, and
  (g) a $C_{1-6}$ alkyl-carbonyl group optionally substituted by 1 to 3 halogen atoms,
(3) a $C_{3-10}$ cycloalkyl group (e.g., cyclopropyl, cyclobutyl, cyclopentyl, cyclohexyl, adamantyl) optionally substituted by 1 to 3 substituents selected from
  (a) a halogen atom (e.g., a fluorine atom),
  (b) a hydroxy group,
  (c) a $C_{1-6}$ alkoxy group (e.g., methoxy, isopropoxy),
  (d) a $C_{1-6}$ alkyl group (e.g., methyl),
  (e) an amino group optionally mono- or di-substituted by substituent(s) selected from
    (i) a $C_{1-6}$ alkyl group optionally substituted by 1 to 3 halogen atoms,
    (ii) a $C_{1-6}$ alkyl-carbonyl group (e.g., methylcarbonyl, ethylcarbonyl) optionally substituted by 1 to 3 halogen atoms,
    (iii) a $C_{1-6}$ alkoxy-carbonyl group (e.g., methoxycarbonyl, ethoxycarbonyl) optionally substituted by 1 to 3 halogen atoms,
    (iv) a carbamoyl group optionally mono- or di-substituted by $C_{1-6}$ alkyl group(s) (e.g., methylcarbamoyl, ethylcarbamoyl) optionally substituted by 1 to 3 halogen atoms, and
    (v) a formyl group, and
  (f) an oxo group, or
(4) a 5- or 6-membered heterocyclic group (e.g., tetrahydrofuryl, tetrahydropyranyl) each optionally substituted by 1 to 3 substituents selected from
  (a) a halogen atom,
  (b) a hydroxy group,
  (c) a $C_{1-6}$ alkyl group (e.g., methyl), and
  (d) a $C_{1-6}$ alkoxy group, or
2) $R^4$ and $R^5$ form, together with the adjacent nitrogen atom, 4- to 6-membered nitrogen-containing heterocycle (e.g., pyrrolidine, piperidine, piperazine) substituted by 1 to 3 substituents selected from
(1) a halogen atom;
(2) a hydroxy group;
(3) a $C_{1-6}$ alkyl group (e.g., methyl);
(4) a $C_{1-6}$ alkoxy group;
(5) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group (e.g., methylcarbonyl, ethylcarbonyl) optionally substituted by 1 to 3 halogen atoms,
  (c) a $C_{1-6}$ alkoxy-carbonyl group (e.g., methoxycarbonyl, ethoxycarbonyl) optionally substituted by 1 to 3 halogen atoms,
  (d) a carbamoyl group optionally mono- or di-substituted by $C_{1-6}$ alkyl group(s) (e.g., methylcarbamoyl, ethylcarbamoyl) optionally substituted by 1 to 3 halogen atoms, and
  (e) a formyl group, and
(6) an oxo group.

[Compound A3]
Compound (I) wherein
ring A is a tetrahydrofuran ring;
$R^1$ is a hydrogen atom or a halogen atom;
$R^2$ is a hydrogen atom, a halogen atom or a $C_{1-6}$ alkyl group;
$R^3$ is a hydrogen atom or a $C_{1-6}$ alkyl group; and
$R^4$ and $R^5$ are
1) each independently
(1) a hydrogen atom
(2) a $C_{1-6}$ alkyl group (e.g., methyl, ethyl, propyl, isopropyl, butyl, isobutyl, sec-butyl, tert-butyl, pentyl, neopentyl, 1-ethylpropyl, 1,2,2-trimethylpropyl) optionally substituted by 1 to 3 substituents selected from
  (a) a halogen atom (e.g., a fluorine atom),
  (b) a hydroxy group,
  (c) a $C_{1-6}$ alkoxy group (e.g., methoxy, isopropoxy),
  (d) a $C_{3-10}$ cycloalkyl group (e.g., cyclopropyl, cyclohexyl) optionally substituted by 1 to 3 substituents selected from a hydroxy group and a $C_{1-6}$ alkyl group, and
  (e) a 4- to 6-membered oxygen-containing heterocyclic group (e.g., oxetanyl, tetrahydrofuryl, tetrahydropyranyl) optionally substituted by $C_{1-6}$ alkyl group(s) (e.g., methyl), (3) a $C_{3-10}$ cycloalkyl group (e.g., cyclopropyl, cyclobutyl, cyclopentyl, cyclohexyl, adamantyl) optionally substituted by 1 to 3 substituents selected from
  (a) a hydroxy group, and
  (b) a $C_{1-6}$ alkyl group (e.g., methyl), or
(4) a 5- or 6-membered heterocyclic group (e.g., tetrahydrofuryl, tetrahydropyranyl), or
2) $R^4$ and $R^5$ form, together with the adjacent nitrogen atom, 4- to 6-membered nitrogen-containing heterocycle (e.g., piperidine) substituted by hydroxy group(s), which is optionally substituted by $C_{1-6}$ alkyl group(s) (e.g., methyl).

[Compound B1]
Compound (I) wherein
ring A is a tetrahydrofuran ring;
$R^1$ is a hydrogen atom or a fluorine atom;
$R^2$ is a fluorine atom or a methyl group;
$R^3$ is a hydrogen atom or a methyl group;
$R^4$ is
(1) a $C_{1-6}$ alkyl group (e.g., methyl, ethyl, propyl, isopropyl, butyl, isobutyl, sec-butyl, tert-butyl, pentyl, neopentyl, 1-ethylpropyl, 1,2,2-trimethylpropyl) optionally substituted by 1 to 3 substituents selected from
  (i) a halogen atom (e.g., a fluorine atom),
  (ii) a hydroxy group,
  (iii) a $C_{1-6}$ alkoxy group (e.g., methoxy, isopropoxy),
  (iv) a $C_{3-10}$ cycloalkyl group (e.g., cyclopropyl, cyclohexyl) optionally substituted by 1 to 3 substituents selected from a hydroxy group and a $C_{1-6}$ alkyl group, and
  (v) a 4- to 6-membered oxygen-containing heterocyclic group (e.g., oxetanyl, tetrahydrofuryl, tetrahydropyranyl) optionally substituted by $C_{1-6}$ alkyl group(s) (e.g., methyl),
(2) a $C_{3-10}$ cycloalkyl group (e.g., cyclopropyl, cyclobutyl, cyclopentyl, cyclohexyl, adamantyl) optionally substituted by 1 to 3 substituents selected from
  (i) a hydroxy group, and
  (ii) a $C_{1-6}$ alkyl group (e.g., methyl), or
(3) a 5- or 6-membered heterocyclic group (e.g., tetrahydrofuryl, tetrahydropyranyl) optionally substituted by 1 to 3 substituents selected from
  (i) a hydroxy group, and
  (ii) a $C_{1-6}$ alkyl group (e.g., methyl); and
$R^5$ is a hydrogen atom.

[Compound C1]
Compound (I) wherein
ring A is a tetrahydrofuran ring;
$R^1$ is a hydrogen atom or a fluorine atom;
$R^2$ is a fluorine atom or a methyl group;
$R^3$ is a hydrogen atom or a methyl group;
$R^4$ is
(1) a $C_{1-6}$ alkyl group (e.g., methyl, ethyl, propyl, isopropyl, butyl, isobutyl, sec-butyl, tert-butyl, pentyl, neopentyl, 1-ethylpropyl, 1,2,2-trimethylpropyl) optionally substituted by 1 to 3 substituents selected from
  (i) a hydroxy group,
  (ii) a $C_{1-6}$ alkoxy group (e.g., methoxy, isopropoxy), and
  (iii) a 5- or 6-membered oxygen-containing heterocyclic group (e.g., tetrahydrofuryl, tetrahydropyranyl), or
(2) a $C_{3-10}$ cycloalkyl group (e.g., cyclopropyl, cyclobutyl, cyclopentyl, cyclohexyl, adamantyl) optionally substituted by 1 to 3 substituents selected from
  (i) a hydroxy group, and
  (ii) a $C_{1-6}$ alkyl group (e.g., methyl); and
$R^5$ is a hydrogen atom.

[Compound C2]
Compound (I) wherein
ring A is a tetrahydrofuran ring;
$R^1$ is a hydrogen atom or a fluorine atom;
$R^2$ is a fluorine atom or a methyl group (preferably, a methyl group);
$R^3$ is a hydrogen atom or a methyl group (preferably, a hydrogen atom); and
$R^4$ and $R^5$ form, together with the adjacent nitrogen atom, 5- or 6-membered nitrogen-containing heterocycle (e.g., piperidine) substituted by hydroxy group(s), which is optionally substituted by $C_{1-6}$ alkyl group(s) (e.g., methyl).

[Compound D]
N-(3-{[(2-hydroxy-2-methylpropyl)amino]methyl}-8-methylquinolin-7-yl)-4-(tetrahydrofuran-3-ylmethoxy)benzamide or a salt thereof.
N-{8-methyl-3-[(tetrahydro-2H-pyran-4-ylamino)methyl] quinolin-7-yl}-4-(tetrahydrofuran-3-ylmethoxy)benzamide or a salt thereof.
N-(3-{[(trans-4-hydroxycyclohexyl)amino]methyl}-8-methylquinolin-7-yl)-4-(tetrahydrofuran-3-ylmethoxy)benzamide or a salt thereof.
N-{3-[(cyclopentylamino)methyl]-8-methylquinolin-7-yl}-4-(tetrahydrofuran-3-ylmethoxy)benzamide or a salt thereof.
N-[8-methyl-3-({[(2R)-tetrahydrofuran-2-ylmethyl]amino}methyl)quinolin-7-yl]-4-[(2R)-tetrahydrofuran-2-ylmethoxy]benzamide or a salt thereof.
N-{3-[(cyclopentylamino)methyl]-8-methylquinolin-7-yl}-4-[(2R)-tetrahydrofuran-2-ylmethoxy]benzamide or a salt thereof.
N-(3-{[(2,2-dimethylpropyl)amino]methyl}-8-methylquinolin-7-yl)-4-[(2R)-tetrahydrofuran-2-ylmethoxy]benzamide or a salt thereof.
N-[8-methyl-3-({[(2R)-tetrahydrofuran-2-ylmethyl]amino}methyl)quinolin-7-yl]-4-[(2S)-tetrahydrofuran-2-ylmethoxy]benzamide or a salt thereof.
N-(3-{[(2-hydroxy-2-methylpropyl)amino]methyl}-8-methylquinolin-7-yl)-4-[(2S)-tetrahydrofuran-2-ylmethoxy]benzamide or a salt thereof.
N-[8-methyl-3-({[(2S)-tetrahydrofuran-2-ylmethyl]amino}methyl)quinolin-7-yl]-4-[(2S)-tetrahydrofuran-2-ylmethoxy]benzamide or a salt thereof.
N-(3-{[(2-methoxy-2-methylpropyl)amino]methyl}-8-methylquinolin-7-yl)-4-[(2S)-tetrahydrofuran-2-ylmethoxy]benzamide or a salt thereof.
N-{8-methyl-3-[(tetrahydro-2H-pyran-4-ylamino)methyl] quinolin-7-yl}-4-[(2S)-tetrahydrofuran-2-ylmethoxy]benzamide or a salt thereof.
N-(8-methyl-3-{[(tetrahydro-2H-pyran-4-ylmethyl)amino] methyl}quinolin-7-yl)-4-[(2S)-tetrahydrofuran-2-ylmethoxy]benzamide or a salt thereof.
N-(8-methyl-3-{[(tetrahydro-2H-pyran-4-ylmethyl)amino] methyl}quinolin-7-yl)-4-[(2R)-tetrahydrofuran-2-ylmethoxy]benzamide or a salt thereof.
N-[8-methyl-3-({[(3-methyloxetan-3-yl)methyl]amino}methyl)quinolin-7-yl]-4-[(2S)-tetrahydrofuran-2-ylmethoxy]benzamide or a salt thereof.
N{3-[(ethylamino)methyl]-8-methylquinolin-7-yl}-4-[(2S)-tetrahydrofuran-2-ylmethoxy]benzamide or a salt thereof.
N-{3-[(cyclopentylamino)methyl]-8-methylquinolin-7-yl}-4-[(2S)-tetrahydrofuran-2-ylmethoxy]benzamide or a salt thereof.
N-(3-{[(cyclopropylmethyl)amino]methyl}-8-methylquinolin-7-yl)-4-[(2S)-tetrahydrofuran-2-ylmethoxy]benzamide or a salt thereof.

N-(8-methyl-3-{[(2-methylpropyl)amino]methyl}quinolin-7-yl)-4-[(2S)-tetrahydrofuran-2-ylmethoxy]benzamide or a salt thereof.

N-(3-{[(2,2-dimethylpropyl)amino]methyl}-8-methylquinolin-7-yl)-4-[(2S)-tetrahydrofuran-2-ylmethoxy]benzamide or a salt thereof.

N-(3-{[(trans-4-hydroxycyclohexyl)amino]methyl}-8-methylquinolin-7-yl)-4-[(2R)-tetrahydrofuran-2-ylmethoxy]benzamide or a salt thereof.

N-[3-({[(1-hydroxycyclohexyl)methyl]amino}methyl)-8-methylquinolin-7-yl]-4-[(2S)-tetrahydrofuran-2-ylmethoxy]benzamide or a salt thereof.

N-(3-{[(5-hydroxytricyclo[3.3.1.1$^{3,7}$]dec-2-yl)amino]methyl}-8-methylquinolin-7-yl)-4-(tetrahydrofuran-2-ylmethoxy)benzamide or a salt thereof.

N-[8-methyl-3-({[2-(1-methylethoxy)ethyl]amino}methyl)quinolin-7-yl]-4-(tetrahydrofuran-2-ylmethoxy)benzamide or a salt thereof.

N-(3-{[(3-hydroxytricyclo[3.3.1.1$^{3,7}$]dec-1-yl)amino]methyl}-8-methylquinolin-7-yl)-4-(tetrahydrofuran-2-ylmethoxy)benzamide or a salt thereof.

N-{8-methyl-3-[(propylamino)methyl]quinolin-7-yl}-4-[(2S)-tetrahydrofuran-2-ylmethoxy]benzamide or a salt thereof.

N-[3-({[(1R,2R)-2-hydroxycyclohexyl]amino}methyl)-8-methylquinolin-7-yl]-4-[(2S)-tetrahydrofuran-2-ylmethoxy]benzamide or a salt thereof.

N-[3-({[(1S,2S)-2-hydroxycyclohexyl]amino}methyl)-8-methylquinolin-7-yl]-4-[(2S)-tetrahydrofuran-2-ylmethoxy]benzamide or a salt thereof.

N-(3-{[(trans-4-hydroxycyclohexyl)amino]methyl}-8-methylquinolin-7-yl)-4-[(2S)-tetrahydrofuran-2-ylmethoxy]benzamide or a salt thereof.

N-[8-methyl-3-({[2-(1-methylethoxy)ethyl]amino}methyl)quinolin-7-yl]-4-[(2S)-tetrahydrofuran-2-ylmethoxy]benzamide or a salt thereof.

N-(3-{[(trans-4-hydroxy-4-methylcyclohexyl)amino]methyl}-8-methylquinolin-7-yl)-4-[(2S)-tetrahydrofuran-2-ylmethoxy]benzamide or a salt thereof.

N-(3-{[(trans-4-hydroxy-4-methylcyclohexyl)amino]methyl}-8-methylquinolin-7-yl)-4-[(2R)-tetrahydrofuran-2-ylmethoxy]benzamide or a salt thereof.

N-(3-{[(cis-4-hydroxy-4-methylcyclohexyl)amino]methyl}-8-methylquinolin-7-yl)-4-[(2S)-tetrahydrofuran-2-ylmethoxy]benzamide or a salt thereof.

N-(3-{[(1-ethylpropyl)amino]methyl}-8-methylquinolin-7-yl)-4-[(2S)-tetrahydrofuran-2-ylmethoxy]benzamide or a salt thereof.

N-[8-methyl-3-({[(1R)-1-methylpropyl]amino}methyl)quinolin-7-yl]-4-[(2S)-tetrahydrofuran-2-ylmethoxy]benzamide or a salt thereof.

N-[8-methyl-3-({[(1S)-1-methylpropyl]amino}methyl)quinolin-7-yl]-4-[(2S)-tetrahydrofuran-2-ylmethoxy]benzamide or a salt thereof.

N-{3-[(cyclobutylamino)methyl]-8-methylquinolin-7-yl}-4-[(2S)-tetrahydrofuran-2-ylmethoxy]benzamide or a salt thereof.

N-[8-methyl-3-({[(1R)-1,2,2-trimethylpropyl]amino}methyl)quinolin-7-yl]-4-[(2S)-tetrahydrofuran-2-ylmethoxy]benzamide or a salt thereof.

N-(8-methyl-3-{[(2-methylpropyl)amino]methyl}quinolin-7-yl)-4-(tetrahydrofuran-3-ylmethoxy)benzamide or a salt thereof.

N-(3-{[(2,2-dimethylpropyl)amino]methyl}-8-methylquinolin-7-yl)-4-(tetrahydrofuran-3-ylmethoxy)benzamide or a salt thereof.

N-(8-methyl-3-{[(tetrahydro-2H-pyran-4-ylmethyl)amino]methyl}quinolin-7-yl)-4-(tetrahydrofuran-3-ylmethoxy)benzamide or a salt thereof.

N-(3-{[(trans-4-hydroxy-4-methylcyclohexyl)amino]methyl}-8-methylquinolin-7-yl)-4-(tetrahydrofuran-3-ylmethoxy)benzamide or a salt thereof.

N-(3-{[(2-methoxy-2-methylpropyl)amino]methyl}-8-methylquinolin-7-yl)-4-(tetrahydrofuran-3-ylmethoxy)benzamide or a salt thereof.

N-{3-[(4-hydroxy-4-methylpiperidin-1-yl)methyl]-8-methylquinolin-7-yl}-4-(tetrahydrofuran-3-ylmethoxy)benzamide or a salt thereof.

2-fluoro-N-(3-{[(2-hydroxy-2-methylpropyl)amino]methyl}-8-methylquinolin-7-yl)-4-[(2S)-tetrahydrofuran-2-ylmethoxy]benzamide or a salt thereof.

N-(3-{[(2,2-dimethylpropyl)amino]methyl}-8-methylquinolin-7-yl)-2-fluoro-4-[(2S)-tetrahydrofuran-2-ylmethoxy]benzamide or a salt thereof.

2-fluoro-N-(3-{[(trans-4-hydroxy-4-methylcyclohexyl)amino]methyl}-8-methylquinolin-7-yl)-4-[(2S)-tetrahydrofuran-2-ylmethoxy]benzamide or a salt thereof.

2-fluoro-N-(8-methyl-3-{[(2-methylpropyl)amino]methyl}quinolin-7-yl)-4-[(2S)-tetrahydrofuran-2-ylmethoxy]benzamide or a salt thereof.

2-fluoro-N-{8-methyl-3-[(propylamino)methyl]quinolin-7-yl}-4-[(2S)-tetrahydrofuran-2-ylmethoxy]benzamide or a salt thereof.

N-{3-[(4-hydroxy-4-methylpiperidin-1-yl)methyl]-8-methylquinolin-7-yl}-4-[(2S)-tetrahydrofuran-2-ylmethoxy]benzamide or a salt thereof.

[Compound E]

N-[8-methyl-3-({[(2S)-tetrahydrofuran-2-ylmethyl]amino}methyl)quinolin-7-yl]-4-[(2S)-tetrahydrofuran-2-ylmethoxy]benzamide or a salt thereof.

N-{8-methyl-3-[(tetrahydro-2H-pyran-4-ylamino)methyl]quinolin-7-yl}-4-[(2S)-tetrahydrofuran-2-ylmethoxy]benzamide or a salt thereof.

N-(8-methyl-3-{[(2-methylpropyl)amino]methyl}quinolin-7-yl)-4-[(2S)-tetrahydrofuran-2-ylmethoxy]benzamide or a salt thereof.

N-(3-{[(trans-4-hydroxy-4-methylcyclohexyl)amino]methyl}-8-methylquinolin-7-yl)-4-[(2S)-tetrahydrofuran-2-ylmethoxy]benzamide or a salt thereof.

N-{3-[(4-hydroxy-4-methylpiperidin-1-yl)methyl]-8-methylquinolin-7-yl}-4-[(2S)-tetrahydrofuran-2-ylmethoxy]benzamide or a salt thereof.

When compound (I) is in the form of a salt, concrete examples thereof include salts with inorganic bases, ammonium salts, salts with organic bases, salts with inorganic acids, salts with organic acids, salts with basic, or acidic amino acids and the like.

Preferable examples of the salts with inorganic bases include alkali metal salts such as sodium salt, potassium salt, and the like; alkaline earth metal salts such as calcium salts, magnesium salts, barium salts, and the like; aluminum salts, and the like.

Preferable examples of the salts with organic bases include salts with trimethylamine, triethylamine, pyridine, picoline, ethanolamine, diethanolamine, triethanolamine, dicyclohexylamine, N,N'-dibenzylethylenediamine, and the like.

Preferable examples of the salts with inorganic acids include salts with hydrochloric acid, hydrobromic acid, nitric acid, sulfuric acid, phosphoric acid, and the like.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like.

Preferable examples of the salts with basic amino acids include salts with arginine, lysine, ornithine, and the like.

Preferable examples of the salts with acidic amino acids include salts with aspartic acid, glutamic acid, and the like.

Of these, pharmaceutically acceptable salts are preferable.

Compound (I) may be any of anhydride (non-hydrate) and hydrate. In addition, compound (I) may be any of non-solvate and solvate.

Moreover, compound (I) may be labeled with an isotope (e.g., $^3$H, $^{14}$C, $^{35}$S, $^{125}$I etc.).

Furthermore, a deuterium exchange compound wherein $^1$H is converted to $^2$H(D) is also encompassed in compound (I).

Compound (I) may be a pharmaceutically acceptable cocrystal or a cocrystal salt. Here, the cocrystal or cocrystal salt means a crystalline substance, which is constituted from two or more kinds of specific solids each having different physical properties (e.g., structure, melting point, heat of fusion, hygroscopicity, solubility, stability etc.) at room temperature. The cocrystal and cocrystal salt can be produced according to a cocrystallization method known per se.

When compound (I) contains an optical isomer, a stereoisomer, a regioisomer or a rotamer, these are also encompassed in compound (I), and can be obtained as a single product according to synthesis and separation methods known per se. For example, when compound (I) has an optical isomer, an optical isomer resolved from this compound is also encompassed in compound (I).

The optical isomer can be produced by a method known per se (e.g., a fractional recrystallization method, a chiral column method, a diastereomer method).

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer) and organic solvents (e.g., ethanol, methanol, isopropanol, acetonitrile, trifluoroacetic acid, diethylamine) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., fractional recrystallization, a chromatography method) and the like, and is subjected to a chemical treatment such as hydrolysis and the like to separate an optically active reagent moiety, whereby an optical isomer is obtained. For example, when compound (I) contains a hydroxyl group, or a primary or secondary amino group in a molecule, the compound and an optically active organic acid (e.g., MTPA [α-methoxy-α-(trifluoromethyl)phenylacetic acid], (−)-menthoxyacetic acid) and the like are subjected to condensation reaction to give diastereomers in the ester form or in the amide form, respectively. When compound (I) has a carboxyl group, this compound and an optically active amine or alcohol are subjected to condensation reaction to give diastereomers in the amide form or in the ester form, respectively. The separated diastereomer is converted to an optical isomer of the original compound by acid hydrolysis or base hydrolysis.

A prodrug of compound (I) means a compound which is converted to compound (I) with a reaction due to an enzyme, an gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like.

Any of these compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, published by HIROKAWA SHOTEN (1990).

Compound (I) can be produced according to [Production Method 1-1] to [Production Method 3-1], which are described in detail below, or an analogous method thereto.

The compounds for the starting compound may be used in the form of a salt, respectively. As such salt, those exemplified as the salt of the aforementioned compound (I) and the like can be used.

In the following [Production Method 1-1] to [Production Method 3-1], when alkylation reaction, hydrolysis reaction, amination reaction, esterification reaction, amidation reaction, esterification reaction, etherification reaction, oxidation reaction, reduction reaction etc. are to be conducted, these reactions are carried out according to methods known per se, for example, those described in Organic Functional Group Preparations, 2nd Ed., Academic Press Inc., 1989; Comprehensive Organic Transformations, VCH Publishers Inc., 1989; and the like.

In the following production methods, the "room temperature" is 15-30° C.

A solvent to be used in each reaction is explained in the following.

Examples of the "alcohol solvent" include methanol, ethanol, propanol, 2-propanol, butanol, isobutanol, tert-butanol and the like.

Examples of the "ester solvent" include methyl acetate, ethyl acetate, n-butyl acetate, tert-butyl acetate and the like.

Examples of the "ether solvent" include diethyl ether, diisopropyl ether, tert-butyl methyl ether, tetrahydrofuran (THF), 1,4-dioxane, 1,2-dimethoxyethane and the like.

Examples of the "halogenated hydrocarbon solvent" include dichloromethane, chloroform, 1,2-dichloroethane, carbon tetrachloride and the like.

Examples of the "aromatic solvent" include benzene, toluene, xylene, pyridine and the like.

Examples of the "nitrile solvent" include acetonitrile, propionitrile and the like.

Examples of the "amide solvent" include N,N-dimethylformamide (DMF), N,N-dimethylacetamide (DMA), 1-methyl-2-pyrrolidone (NMP) and the like.

Examples of the "ketone solvent" include acetone, methylethylketone and the like.

Examples of the "sulfoxide solvent" include dimethyl sulfoxide (DMSO) and the like.

Examples of the "organic acid solvent" include formic acid, acetic acid and the like.

[Production Method 1-1]

Compound (I) can be produced by, for example, a reductive amination reaction of compound (II) with compound (III) shown in the following reaction scheme 1.

(Reaction scheme 1)

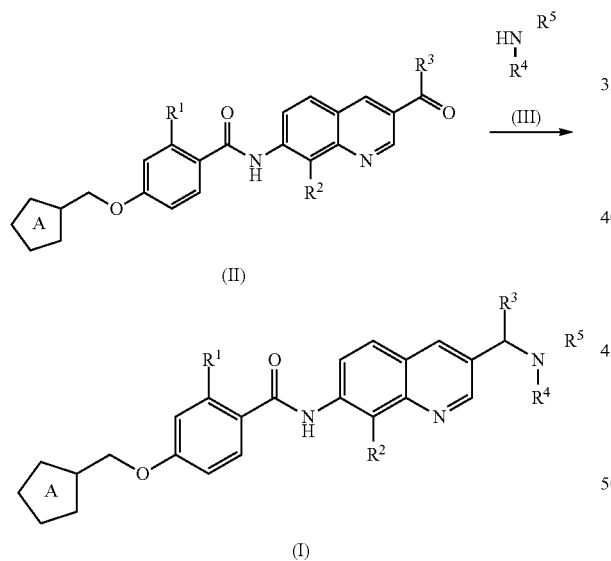

(I)

wherein each symbol is as defined above.

In other words, compound (I) can be obtained by reacting compound (II) and compound (III) in an amount of 1 equivalent to 50 equivalents (preferably 1.2 equivalents to 5 equivalents) relative to compound (II) with a reducing agent in an inert solvent.

Examples of the inert solvent include alcohol solvents, ether solvents, halogenated hydrocarbon solvents, aromatic solvents, nitrile solvents, amide solvents, organic acid solvents and the like. These solvents may be used in a mixture of two or more kinds thereof at an appropriate ratio. Of these, methanol, ethanol, DMF, DMA, NMP, acetic acid and the like are preferable.

As the reducing agent, sodium borohydride, sodium triacetoxyborohydride, sodium cyanoborohydride and the like are used. The amount of the reducing agent to be used is generally 1 equivalent to 20 equivalents, preferably 1 equivalent to 5 equivalents, relative to compound (II).

The reaction temperature is generally −20° C. to 150° C., preferably 0° C. to 60° C. The reaction time is generally 5 min to 40 hr, preferably 1 hr to 24 hr.

In addition, the reaction can also be performed in the presence of an acid. Examples of the acid to be used include organic acids such as acetic acid, methanesulfonic acid and the like; inorganic acids such as hydrochloric acid, sulfuric acid and the like; and Lewis acids such as titanium tetrachloride, titanium isopropoxide and the like. The amount of the acid to be used is generally 0.01 equivalent to 100 equivalents relative to compound (II) for organic acid or Lewis acid, and generally 0.01 equivalent to 10 equivalents relative to compound (II) for inorganic acid. When an organic acid is used, an excess amount of the organic acid may be used as a reaction solvent.

Compound (III) can be produced according to a method known per se.

Compound (II) can be produced by the method described in [Production method 2-1] mentioned below or a method analogous thereto, or from the following compound (IIa) by an oxidation reaction known per se.

[Production Method 1-2]

Compound (I) can also be produced by, for example, an amination reaction of compound (IV) with compound (III) shown in the following reaction scheme 2.

(Reaction scheme 2)

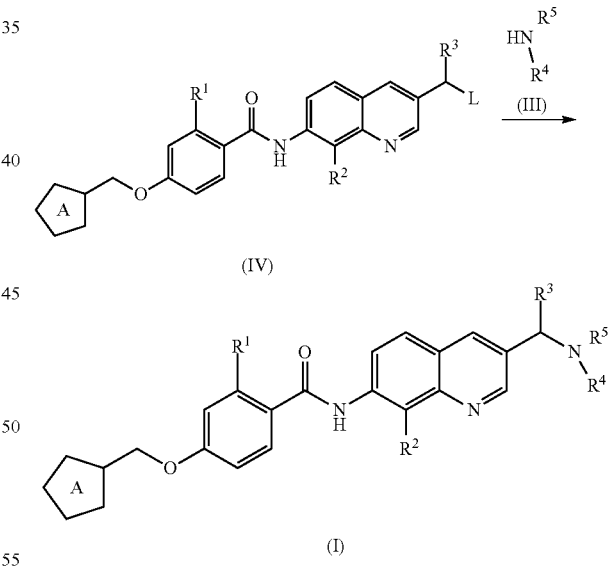

(I)

wherein L is a leaving group, and other symbols are as defined above.

Examples of the "leaving group" for L include a halogen atom (e.g., chlorine, bromine, iodine), optionally halogenated $C_{1-6}$ alkylsulfonyloxy (e.g., methanesulfonyloxy, ethanesulfonyloxy, trifluoromethanesulfonyloxy), $C_{6-10}$ arylsulfonyloxy optionally having substituent(s), hydroxy and the like.

The "leaving group" is preferably a halogen atom (e.g., chlorine, bromine, iodine), methanesulfonyloxy, trifluoromethanesulfonyloxy, p-toluenesulfonyloxy or the like.

This reaction is generally performed in an inert solvent.

Examples of the "inert solvent" include alcohol solvents, ether solvents, halogenated hydrocarbon solvents, aromatic solvents, nitrile solvents, amide solvents, ketone solvents, sulfoxide solvents, water and the like. These may be used in a mixture of two or more kinds thereof at an appropriate ratio. Of these, acetonitrile, DMF, DMA, NMP, acetone, ethanol, pyridine and the like are preferable.

The amount of compound (III) to be used is generally 1 equivalent to 100 equivalents relative to compound (IV). In addition, an excess amount of compound (III) may be used as a reaction solvent.

The reaction temperature is generally about −20° C. to 200° C., preferably room temperature to 100° C. The reaction time is, for example about 0.5 hr to 1 day.

This reaction may be performed in the co-presence of a base as necessary.

Examples of the "base" include;
1) strong bases such as alkali metal or alkaline earth metal hydrides (e.g., lithium hydride, sodium hydride, potassium hydride, calcium hydride), alkali metal or alkaline earth metal amides (e.g., lithium amide, sodium amide, lithium diisopropylamide, lithium dicyclohexylamide, lithium hexamethyldisilazide, sodium hexamethyldisilazide, potassium hexamethyldisilazide), alkali metal or alkaline earth metal $C_{1-6}$ alkoxides (e.g., sodium methoxide, sodium ethoxide, potassium tert-butoxide), and the like;
2) inorganic bases such as alkali metal or alkaline earth metal hydroxides (e.g., sodium hydroxide, potassium hydroxide, lithium hydroxide, barium hydroxide), alkali metal or alkaline earth metal carbonates (e.g., sodium carbonate, potassium carbonate, cesium carbonate), alkali metal hydrogen carbonates (e.g., sodium hydrogen carbonate, potassium hydrogen carbonate) and the like;
3) organic bases such as amines (e.g., triethylamine, N,N-diisopropylethylamine, N-methylmorpholine, 4-dimethylaminopyridine, DBU (1,8-diazabicyclo[5.4.0]undec-7-ene), DBN (1,5-diazabicyclo[4.3.0]non-5-ene)), basic heterocyclic compounds (e.g., pyridine, imidazole, 2,6-lutidine) and the like; and the like.

Of the above-mentioned bases, triethylamine, N,N-diisopropylethylamine, pyridine and the like are preferable.

The amount of the base to be used is generally 0.1 equivalent to 100 equivalents, preferably 1 equivalent to 10 equivalents, relative to compound (IV).

Compound (IV) can be produced according to the method described in [Production method 2-2] or [Production method 2-3] mentioned below, or a method analogous thereto.

[Production Method 2-1]

Compound (IIa) which is compound (II) wherein $R^3$ is hydrogen can be produced by, for example, the method shown in the following reaction scheme 3.

(Reaction scheme 3)

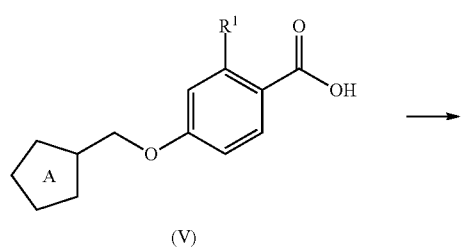

wherein $X^-$ is a counter anion such as tetrahydrofluoroborate anion and the like, and other symbols are as defined above.

Compound (V) is reacted with, for example, a halogenating agent such as oxalyl chloride, thionyl chloride and the like for conversion to compound (Va), which is carboxylic acid halide, and then reacted with compound (VI) in the presence of a base such as triethylamine and the like to give compound (VIa). In addition, compound (VIa) can also be obtained by directly reacting compound (V) with compound (VI) in the presence of a condensing agent such as carbodiimide derivative etc. (e.g., 1-ethyl-3-(3-dimethylaminopropyl)carbodiimide hydrochloride) and an additive such as 1-hydroxybenzotriazole, 4-dimethylaminopyridine and the like.

The nitro group of compound (VIa) is reduced by catalytic hydrogenation or using a reducing agent such as iron, tin chloride and the like to give compound (VIb).

Successively, compound (IIa) can be obtained by, for example, reacting compound (VIb) with compound (VII) in the presence of morpholine in 1-butanol at 80° C. overnight.

Compound (V) can be produced according to a method known per se, or [Production method 3-1] mentioned below.

Compound (VI) can be produced according to a method known per se.

Compound (VII) can be prepared by a method known per se, for example, the method described in Synthesis, 641-645 (1988) and the like.

[Production Method 2-2]

Compound (IVa) which is compound (IV) wherein $R^3$ is to hydrogen can be produced by, for example, the method shown in the following Reaction scheme 4.

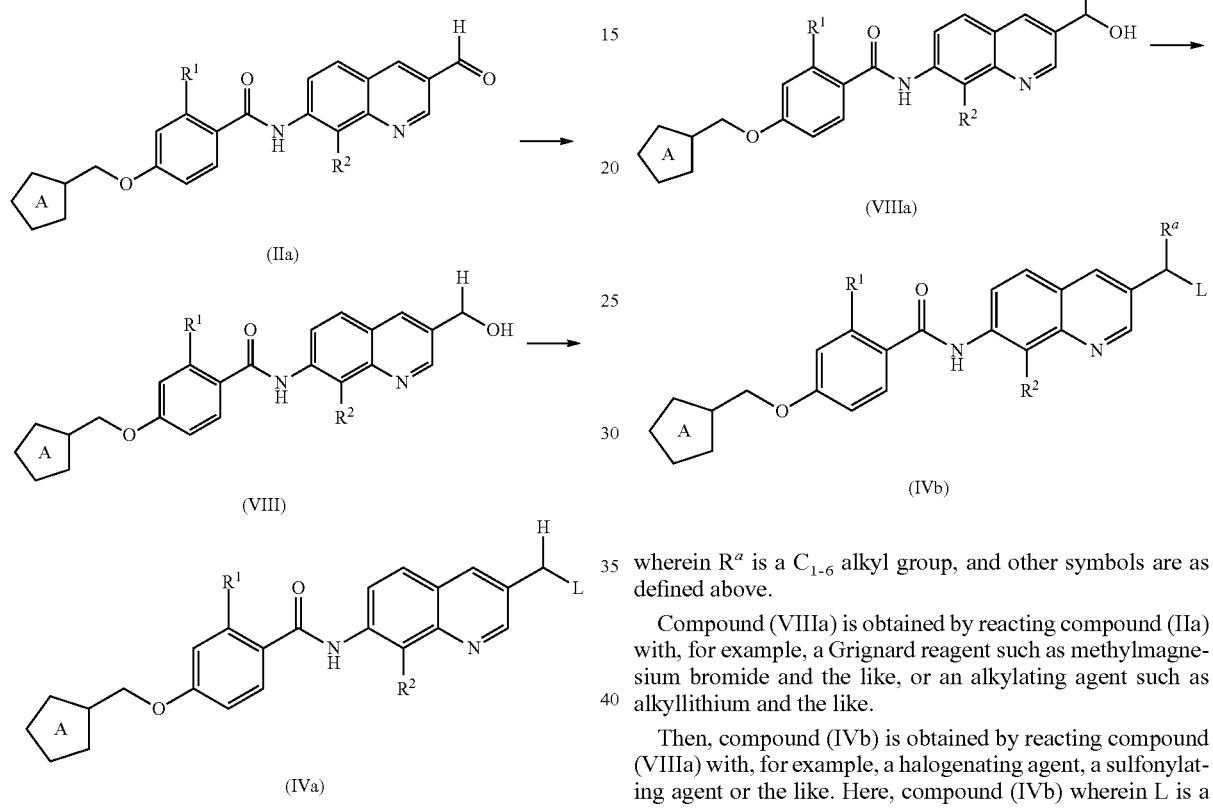

wherein each symbol is as defined above.

Compound (VIII) is obtained by reacting compound (IIa) with, for example, a reducing agent such as sodium borohydride, aluminum lithium hydride and the like.

Then, compound (IVa) is obtained by reacting compound (VIII) with, for example, a halogenating agent, a sulfonylating agent or the like. Here, compound (IVa) wherein L is a halogen atom is obtained by reacting compound (VIII) with, for example, a halogenating agent such as thionyl chloride, tribromophosphine and the like. In addition, compound (IVa) wherein L is sulfonyloxy (e.g., optionally halogenated $C_{1-6}$ alkylsulfonyloxy, $C_{6-10}$ arylsulfonyloxy optionally having substituent(s)) can be obtained by reacting compound (VIII) with, for example, a sulfonylating agent such as methanesulfonyl chloride, p-toluenesulfonyl chloride and the like in the presence of a base such as triethylamine and the like.

[Production Method 2-3]

Compound (IVb) which is compound (IV) wherein $R^3$ is a $C_{1-6}$ alkyl group can be produced by, for example, the method shown in the following Reaction scheme 5.

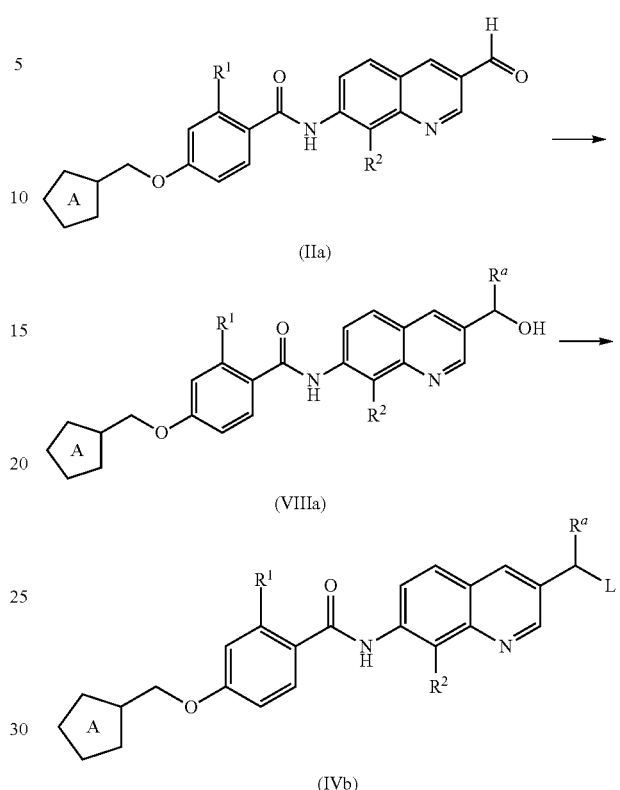

wherein $R^a$ is a $C_{1-6}$ alkyl group, and other symbols are as defined above.

Compound (VIIIa) is obtained by reacting compound (IIa) with, for example, a Grignard reagent such as methylmagnesium bromide and the like, or an alkylating agent such as alkyllithium and the like.

Then, compound (IVb) is obtained by reacting compound (VIIIa) with, for example, a halogenating agent, a sulfonylating agent or the like. Here, compound (IVb) wherein L is a halogen atom is obtained by reacting compound (VIIIa) with, for example, a halogenating agent such as thionyl chloride, tribromophosphine and the like. In addition, compound (IVb) wherein L is sulfonyloxy (e.g., optionally halogenated $C_{1-6}$ alkylsulfonyloxy, $C_{6-10}$ arylsulfonyloxy optionally having substituent(s)) can be obtained by reacting compound (VIIIa) with, for example, a sulfonylating agent such as methanesulfonyl chloride; p-toluenesulfonyl chloride and the like in the presence of a base such as triethylamine and the like.

[Production Method 3-1]

Compound (V) can be produced by, for example, the method shown in the following Reaction scheme 6.

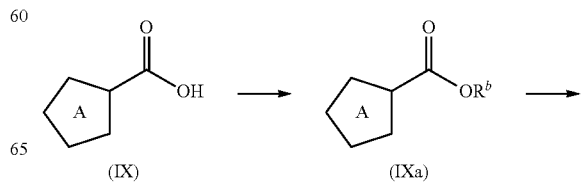

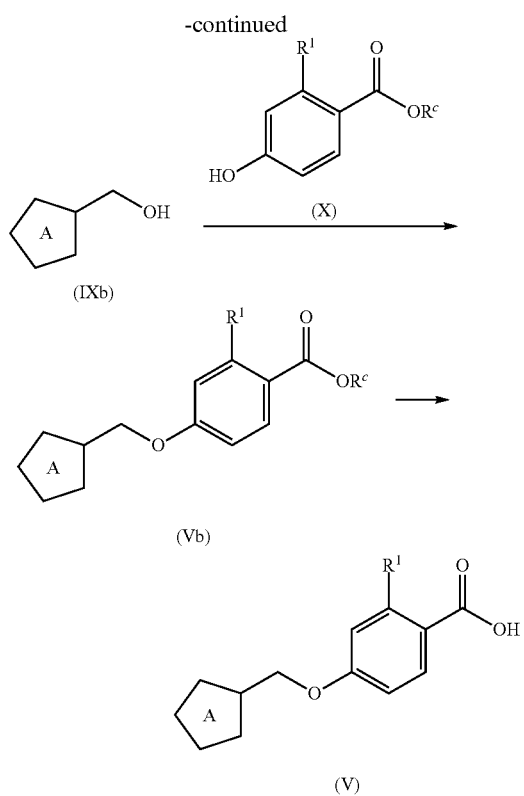

wherein $R^b$ and $R^c$ are each a $C_{1-6}$ alkyl group, and other symbols are as defined above.

Compound (IX) is converted to compound (IXa) by a conventional esterification reaction, and then reacted with, for example, a reducing agent such as sodium borohydride, aluminum lithium hydride and the like to give compound (IXb). In addition, compound (IXb) can also be obtained by directly reacting compound (IX) with, for example, a reducing agent such as aluminum lithium hydride and the like.

Then, compound (IXb) and compound (X) as starting materials are subjected to an etherification reaction such as Mitsunobu reaction using diethyl azodicarboxylate and triphenylphosphine, and the like to give compound (Vb).

The ester compound (Vb) is subjected to conventional hydrolysis to give compound (V).

Compound (IX) and compound (X) can be produced according to a method known per se.

In compound (I) thus obtained, the functional group in a molecule can also be converted to the object functional group by combining chemical reactions known per se. As the examples of such chemical reaction, oxidation reaction, reduction reaction, alkylation reaction, hydrolysis reaction, amination reaction, amidation reaction, esterification reaction, aryl-coupling reaction, deprotection reaction and the like can be mentioned.

In the above-mentioned production methods, when the starting compound has an amino group, a carboxyl group, a hydroxy group, a carbonyl group or a mercapto group as a substituent, a protecting group generally used in peptide chemistry and the like may be introduced into these groups. By removing the protecting group as necessary after the reaction, the objective compound can be obtained.

Examples of the amino-protecting group include a formyl group, a $C_{1-6}$ alkyl-carbonyl group (e.g., acetyl, propionyl), a $C_{1-6}$ alkoxy-carbonyl group (e.g., methoxycarbonyl, ethoxycarbonyl, tert-butoxycarbonyl), a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxyl-protecting group include a $C_{1-6}$ alkyl group, a $C_{7-10}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group and a nitro group.

Examples of the carbonyl-protecting group include cyclic acetal (e.g., 1,3-dioxane), acyclic acetal (e.g., di-$C_{1-6}$ alkyl acetal) and the like.

Examples of the mercapto-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$ alkylamino-carbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

The compound (I) can be isolated and purified by methods known per se such as solvent extraction, changing of liquid properties, transdissolution, crystallization, recrystallization, chromatography, and the like. It is also possible to isolate and purify the starting compounds of a compound (I), or their salts using the same known methods as above, but they can also be used as starting materials in the next process as a reaction mixture without being isolated.

Inasmuch as compound (I) and a prodrug thereof (hereinafter abbreviated as the compound of the present invention) has a superior MCH receptor antagonistic action, it is useful as an agent for the prophylaxis or treatment of diseases caused by MCH.

In addition, the compound of the present invention also shows low toxicity (for example, cardiac toxicity (e.g., hERG inhibitory activity), PLsis inducing potential, acute toxicity, chronic toxicity, genetic toxicity, reproductive toxicity, drug interaction, carcinogenicity, phototoxicity).

Moreover, the compound of the present invention is superior in oral absorbability.

Furthermore, the compound of the present invention is superior in brain transfer function.

Accordingly, the compound of the present invention is safely administered as an agent for the prophylaxis or treatment of diseases caused by MCH, and the like to mammals (e.g., rat, mouse, guinea pig, rabbit, sheep, horse, pig, cow, monkey, human).

The diseases caused by MCH include, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity and the like], hyperphagia, emotional disorder, sexual dysfunction, depression, anxiety and the like.

The compound of the present invention is also useful as a drug for the prophylaxis or treatment of a lifestyle-related diseases such as diabetes (e.g., type 1 diabetes, type 2 diabetes, gestational diabetes, obese diabetes, borderline diabetes), impaired glucose tolerance (IGT), diabetic complications (e.g., diabetic retinopathy, diabetic neuropathy, diabetic nephropathy), hyperlipidemia (e.g., hypertriglyceridemia, hypercholesterolemia, high LDL-cholesterolemia, low HDL-cholesterolemia, postprandial hyperlipemia), arteriosclerosis, arthritis in knee, metabolic syndrome and the like.

Moreover, the compound of the present invention is also useful as an anorexigenic agent.

The compound of the present invention can also be concurrently used with diet therapy (e.g., diet therapy for diabetes), or an exercise therapy.

Furthermore, the compound of the present invention is also useful as a drug for the prophylaxis or treatment of non-alcoholic steatohepatitis (NASH) and non-alcoholic fatty liver disease (NAFLD).

The compound of the present invention can be used for the prophylaxis or treatment of pigmentation disorder based on abnormality of melanin or melanocyte. Here, as the pigmentation disorder, pigment proliferation, pigment decrease and the like can be mentioned. As the pigment proliferation, drug pigmentation caused by antitumor agent and the like; chromatosis and incompetence of pigment associated with diseases such as endocrine metabolism disorder (e.g., Addison's disease), genetic diseases, chronic hepatopathy, kidney failure, acanthosis nigricans, systemic scleroderma and the like; and the like can be mentioned. As the pigment decrease, phenylketonuria, systemic or localized albinism, foliaceous leukoderma or leukoderma vulgaris associated with tuberous sclerosis; depigmentation associated with systemic scleroderma and the like can be mentioned.

The compound of the present invention can be used for the prophylaxis or treatment of depigmentation due to chloasma, ephelides, sunburn and the like; and further, hyperpigmentation or hypopigmentation for cosmetic purposes.

The compound of the present invention is used as is or as a pharmaceutical composition formulated as a preparation together with a pharmacologically acceptable carrier by a method known per se, for example, the method described in the Japanese Pharmacopoeia.

Examples of the pharmacologically acceptable carrier include various organic or inorganic carrier substances conventionally used as a preparation material and, for example, excipient, lubricant, binder and disintegrant for solid preparations; solvent, solubilizing agent, suspending agent, isotonicity agent, buffer and soothing agent for liquid preparations and the like can be mentioned. Where necessary, additives such as preservatives, antioxidants, colorants, sweetening agents, adsorbent, wetting agent and the like can be used during formulation of a preparation.

Examples of the excipient include lactose, sucrose, D-mannitol, starch, cornstarch, crystalline cellulose and light anhydrous silicic acid.

Examples of the lubricant include magnesium stearate, calcium stearate, talc and colloidal silica.

Examples of the binder include crystalline cellulose, sucrose, D-mannitol, dextrin, hydroxypropylcellulose, hydroxypropylmethylcellulose, polyvinylpyrrolidone, starch, sucrose, gelatin, methylcellulose and sodium carboxymethylcellulose.

Examples of the disintegrant include starch, carboxymethylcellulose, calcium carboxymethylcellulose, croscarmellose sodium, sodium carboxymethylstarch and low-substituted hydroxypropylcellulose (L-HPC).

Examples of the solvent include water for injection, alcohol, propylene glycol, macrogol, sesame oil and corn oil.

Examples of the solubilizing agent include polyethylene glycol, propylene glycol, D-mannitol, benzyl benzoate, ethanol, trisaminomethane, cholesterol, triethanolamine, sodium carbonate and sodium citrate.

Examples of the suspending agent include surfactants such as stearyltriethanolamine, sodium lauryl sulfate, lauryl aminopropionic acid, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like.

Examples of the isotonicity agent include glucose, D-sorbitol, sodium chloride, glycerol and D-mannitol.

Examples of the buffer include buffers such as phosphate, acetate, carbonate, citrate and the like.

Examples of the soothing agent include benzyl alcohol.

Examples of the preservative include p-oxybenzoates, chlorobutanol, benzyl alcohol, phenethyl alcohol, dehydroacetic acid and sorbic acid.

Examples of the antioxidant include sulfite and ascorbic acid salt.

Examples of the colorant include water-soluble food tar color (e.g., food colors such as Food Color Red No. 2 and No. 3, Food Color Yellow No. 4 and No. 5, Food Color Blue No. 1 and No. 2 and the like), water-insoluble lake dye (e.g., aluminum salt of the aforementioned water-soluble food tar color), and natural dye (e.g., β-carotene, chlorophyll, ferric oxide red).

Examples of the sweetening agent include saccharin sodium, dipotassium glycyrrhizinate, aspartam and stevia.

Examples of the adsorbent include porous starch, calcium silicate (product name: Florite RE), metasilicate magnesium aluminate (product name: Neusilin) and light anhydrous silicic acid (product name: Sylysia).

Examples of the wetting agent include propyleneglycol monostearate, sorbitan monooleate, diethylene glycol monolaurate and polyoxyethylenelauryl ether.

Examples of the dosage form of the aforementioned pharmaceutical composition include tablet (including sugar-coated tablet, film-coated tablet, sublingual tablet, orally disintegrating tablet, buccal tablet etc.), pill, powder, granule, capsule (including soft capsule, microcapsule), troche, syrup, liquid, emulsion, suspension, controlled-release preparation (e.g., immediate-release preparation, sustained-release preparation, sustained-release microcapsule), aerosol, film (e.g., orally disintegrable film, oral mucous membrane patch film), injection (e.g., subcutaneous injection, intravenous injection, intramuscular injection, intraperitoneal injection, drip infusion), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, and they can be administered safely by oral or parenteral administration (e.g., intravenous, intramuscular, subcutaneous, intraorgan, intranasal, intradermal, ocular instillation, intracerebral, rectal, vaginal, intraperitoneal and intratumor administrations, administration to the vicinity of tumor etc. and direct administration to the lesion).

The content of the compound of the present invention in the pharmaceutical composition is, for example, about 0.1 to 100 wt % of the entire pharmaceutical composition.

The dose of the compound of the present invention is appropriately determined according to the subject of administration, administration route, disease and the like.

For example, the daily dose of the compound of the present invention for oral administration to an adult patient (body weight about 60 kg) with obesity is about 0.1 to about 500 mg, preferably about 1 to about 100 mg, more preferably about 5 to about 100 mg. This amount can be administered at once or in several portions (e.g., 1-3 times) for one day.

In an attempt to enhance the action (therapeutic effect for obesity, diabetes, depression, anxiety etc.) of the compound of the present invention and decrease the amount of the compound of the present invention to be used and the like, as well as prevent or treat complications and improve prognosis, for example, the compound of the present invention can be used in combination with a concomitant drug that does not adversely influence the compound of the present invention. Examples of such concomitant drug include "therapeutic drug for diabetes", "therapeutic drug for diabetic complications", "anti-obesity agent", "therapeutic drug for hypertension", "therapeutic drug for hyperlipidemia", "antiarteriosclerotic drug", "antithrombotic", "diuretic", "therapeutic drug for arthritis", "antianxiety drug", "antidepressant", "psychoneurotic agent", "sleep-inducing drug" and the like. These concomitant drugs may be low-molecular-weight compounds, or high-molecular-weight proteins, polypeptides, antibodies, vaccines or the like. In addition, two or more kinds of these concomitant drugs may be used in combination at an appropriate ratio.

Examples of the above-mentioned "agent for treating diabetes" include insulin preparations (e.g., animal insulin preparations extracted from pancreas of bovine and swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO2007/013694, WO2007/018314, WO2008/093639 or WO2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof), dipeptidyl peptidase IV inhibitors (e.g., Alogliptin or a salt thereof (preferably, benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), 133 agonists (e.g., N-5984), GPR40 agonists (e.g., compound described in WO2004/041266, WO2004/106276, WO2005/063729, WO2005/063725, WO2005/087710, WO2005/095338, WO2007/013689 or WO2008/001931), GLP-1 receptor agonists (e.g., GLP-1, GLP-1MR agent, Liraglutide, Exenatide, AVE-0010, BIM-51077, Aib(8,35)hGLP-1(7,37)$NH_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or an agonist thereof, IKK inhibitors (e.g., AS-2868), leptin resistance-improving drugs, somatostatin receptor agonists, glucokinase activators (e.g., Piragliatin, AZD1656, AZD6370, TTP-355, compound described in WO2006/112549, WO2007/028135, WO2008/047821, WO2008/050821, WO2008/136428 or WO2008/156757), GIP (Glucose-dependent insulinotropic peptide), GPR119 agonists (e.g., PSN821), FGF21, FGF analogue and the like.

Examples of the above-mentioned "therapeutic drug for diabetic complications" include aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF and neurotrophin production/secretion promoting agents described in WO01/14372 (e.g., 4-(4-chlorophenyl)-2-(2-methyl-1-imidazolyl)-5-[3-(2-methylphenoxy)propyl]oxazole), the compounds described in WO2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, pregabalin), serotonin-norepinephrine reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitor and the like.

Examples of the above-mentioned "anti-obesity agent" include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptors, GABA-modulating agents (e.g., topiramate), neuropeptide γ antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetyl CoA carboxylase (ACC) inhibitors, stearoyl-CoA desaturation enzyme inhibitors, microsomal triglyceride transfer protein inhibitors (e.g., R-256918), Na-glucose cotransport carrier inhibitors (e.g., JNJ-28431754, remogliflozin), NFκ inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparation extracted from pancreas of bovine and swine; human GLP-1 preparations genetically synthesized using *Escherichia coli*, yeast; fragment or derivative of GLP-1 (e.g., exenatide, liraglutide)), amylin preparations (e.g., pramlintide, AC-2307), neuropeptide γ agonists (e.g., PYY3-36, derivative of PYY3-36, obinepitide, TM-30339, TM-30335), oxyntomodulin preparations: FGF21 preparations (e.g., animal FGF21 preparation extracted from pancreas of bovine and swine; human FGF21 preparations genetically synthesized using *Escherichia coli*, yeast; fragment or derivative of FGF21)), anorexigenic agents (e.g., P-57) and the like.

Examples of the above-mentioned "therapeutic drug for hypertension" include angiotensin converting enzyme inhibitors (e.g., captopril, enalapril, delapril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine), β blockers (e.g., metoprolol, atenolol, propranolol, carvedilol, pindolol), clonidine and the like.

Examples of the above-mentioned "therapeutic drug for hyperlipidemia" include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., the compounds described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterol (e.g., soysterol, γ-oryzanol), cholesterol absorption inhibitors (e.g., zetia), CETP inhibitors (e.g., dalcetrapib, anacetrapib), ω-3 fatty acid preparations (e.g., ω-3-acid ethyl esters 90) and the like.

Examples of the above-mentioned "antiarteriosclerotic drug" include acyl coenzyme A cholesterol acyltransferase (ACAT) inhibitors (e.g., K-604), LpPLA2 inhibitors (e.g., darapladib, rilapladib), FLAP inhibitors (e.g., AM103, AM803 and the like), 5LO inhibitors (e.g., VIA-2291), sPLA2 inhibitors (e.g., A-002), apoAI mimetic peptides (e.g., D4F), HDL preparations (e.g., CSL-111) and the like.

Examples of the above-mentioned "antithrombotic" include heparin (e.g., heparin sodium, heparin calcium, enoxaparin sodium, dalteparin sodium), warfarin (e.g., warfarin potassium), anti-thrombin drugs (e.g., aragatroban, dabigatran), FXa inhibitors (e.g., rivaroxaban, apixaban, edoxaban, YM150, the compounds described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the above-mentioned "diuretic agent" include xanthine derivatives (e.g., theobromine sodium salicylate, theobromine calcium salicylate), thiazide preparations (e.g., ethiazide, cyclopenthiazide, trichlormethiazide, hydrochlorothiazide, hydroflumethiazide, bentylhydrochlorothiazide, penflutiazide, poly5thiazide, methyclothiazide), antialdosterone preparations (e.g., spironolactone, triamterene), carbonic anhydrase inhibitors (e.g., acetazolamide), chlorobenzenesulfonamide preparations (e.g., chlorthalidone, mefruside, indapamide), azosemide, isosorbide, ethacrynic acid, piretanide, bumetanide, furosemide and the like.

Examples of the above-mentioned "therapeutic drug for arthritis" include ibuprofen and the like.

Examples of the above-mentioned "antianxiety drug" include alprazolam, etizolam, oxazolam, tandospirone, cloxazolam, clotiazepam, clorazepate dipotassium, chlordiazepoxide, diazepam, fludiazepam, flutazolam, flutoprazepam, prazepam, bromazepam, prazepam, bromazepam, mexazolam, medazepam, ethyl loflazepate, lorazepam and the like.

Examples of the above-mentioned "antidepressant" include tricyclic antidepressants (e.g., imipramine, trimipramine, clomipramine, amitriptyline, nortriptyline, amoxapine, lofepramine, dosulepin, desipramine), tetracyclic antidepressants (e.g., maprotiline, mianserin, Japanese parsley purine), selective serotonin uptake inhibitors (e.g., fluoxetine, fluvoxamine, paroxetine, sertraline, escitalopram), serotoninnoradrenaline uptake inhibitors (e.g., milnacipran, duloxetine, venlafaxine), trazodone, mirtazapine, moclobemide and the like.

Examples of the above-mentioned "psychoneurotic agent" include conventional antipsychotic agents (e.g., clocapramine, chlorpromazine, phenobarbital, sultopride, tiapride, thioridazine, floropipamide, mosapramine, moperone, oxypertine, carpipramine, spiperone, sulpiride, zotepine, timiperone, nemonapride, haloperidol, pimozide, prochlorperazine, propericiazine, bromperidol, perphenazine, fluphenazine maleate, mizoribine, levomepromazine), atypical antipsychotic agents (e.g., perospirone, olanzapine, quetiapine, risperidone, clozapine, aripiprazole, ziprasidone, blonanserin, lurasidone) and the like.

Examples of the above-mentioned "sleep-inducing drug" include Ramelteon, GABAergic hypnotics brotizolam, estazolam, flurazepam, nitrazepam, triazolam, flunitrazepam, lormetazepam, rilmazafone, quazepam, zopiclone, eszopiclone, zolpidem, zaleplon, indiplon, gabaxadol); non-GABAergic hypnotics (e.g., eplivanserin, pruvanserin, diphenhydramine, trazodone, doxepin) and the like.

The administration time of the aforementioned concomitant drug is not limited, and the compound of the present invention and the concomitant drug can be administered to an administration subject simultaneously, or may be administered at staggered times. The dosage of the concomitant drug may be determined according to the dose clinically used, and can be appropriately selected depending on an administration subject, administration route, disease, combination and the like.

The administration mode of the concomitant drug is not particularly limited, and the compound of the present invention and the concomitant drug only need to be combined on administration. Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The compounding ratio of the compound of the present invention to the concomitant drug can be appropriately selected depending on the administration subject, administration route, diseases and the like.

EXAMPLES

The present invention is described in detail by way of the following Reference Examples, Examples, Formulation Example and Experimental Example. These are not intended to restrict the present invention, and may be modified within the range not deviating from the scope of this invention.

The "room temperature" in the following Reference Examples and Examples means a temperature of 15° C. to 30° C. For drying an organic layer, anhydrous magnesium sulfate or anhydrous sodium sulfate was employed. Unless otherwise specifically indicated, "%" means percent by weight.

2-Dimethylaminomethylene-1,3-bis(dimethylimmonio) propane bistetrafluoroborate used in the following Reference Examples and Examples was prepared by the method of F. Wudl et al. (Synthesis 1988, 641-644).

Abbreviations used in the present specification mean the following.
Ac: acetyl
Me: methyl
s: singlet
d: doublet
t: triplet
q: quartet
dd: double doublet
dt: double triplet
m: multiplet
br: broad
J: coupling constant
Hz: Hertz
$CDCl_3$: deuterated chloroform
DMA: dimethylacetamide
THF: tetrahydrofuran
NMP: 1-methyl-2-pyrrolidone
DMF: N,N-dimethylformamide
DMSO: dimethyl sulfoxide
$^1$H-NMR: proton nuclear magnetic resonance
FABMS (pos): mass spectrum measured by the (+) method in the Fast Atom Bombardment Mass Spectrometry Reference Example 1

4-(tetrahydrofuran-2-ylmethoxy)benzoic acid

To a solution of tetrahydrofurfuryl alcohol (25 g), methyl 4-hydroxybenzoate (38 g), and triphenylphosphine (72 g) in tetrahydrofuran (300 mL) was slowly added dropwise a solution of diethyl azodicarboxylate in toluene (136 mL, 40% toluene solution) at 0° C., and the mixture was stirred at room temperature for 2 hr. The reaction solution was concentrated, and triphenylphosphine oxide was precipitated from ethyl acetate-hexane. Triphenylphosphine oxide was removed by filtration with a glass filter, and the mother liquor was concentrated. The residue was purified by silica gel column chromatography [developing solvent; hexane:ethyl acetate=100:0 (volume ratio)→hexane:ethyl acetate=70:10 (volume ratio)] to give a colorless oil. The obtained colorless oil was dissolved in tetrahydrofuran (200 mL) and methanol (100 mL), 8N aqueous sodium hydroxide solution (100 mL) was added, and the mixture was stirred at 80° C. for 2 hr with heating. The reaction solution was concentrated, cooled to 0° C., neutralized with 6N hydrochloric acid, and extracted with ethyl acetate. The organic layer was washed with saturated brine and dried over anhydrous magnesium sulfate, and the solvent was evaporated under reduced pressure to give the title compound (17 g, yield 31%) as colorless crystals.
$^1$H NMR (300 MHz, DMSO-$d_6$) δ: 1.61-1.72 (1H, m), 1.76-1.87 (2H, m), 1.89-2.06 (1H, m), 3.69 (1H, q, J=6.9 Hz), 3.79 (1H, q, J=6.9 Hz), 3.82-4.06 (2H, m), 4.12-4.20 (1H, m), 6.99-7.04 (2H, m), 7.85-7.90 (2H, m), 12.61 (1H, s).

Reference Example 2

N-(3-formyl-8-methylquinolin-7-yl)-4-(tetrahydrofuran-2-ylmethoxy)benzamide 4-(Tetrahydrofuran-2-ylmethoxy)benzoic acid (17.0 g) obtained in Reference Example 1, oxalyl dichloride (19.0 g) and N,N-dimethylformamide (2 drops) were mixed with tetrahydrofuran (250 mL), and the mixture was stirred at room temperature for 2 hr. The reaction mixture was concentrated under reduced pressure, and N,N-dimethylacetamide (50 mL) was added thereto. To the mixture was added a solution of 2-methyl-3-nitroaniline (10.3 g) and triethylamine (13.9 mL) in N,N-dimethylacetamide (50 ml) under ice-cooling, and the mixture was stirred at room temperature for 24 hr. Water was added to the reaction mixture, and the mixture was extracted with ethyl acetate. The organic layer was washed with saturated brine and dried over anhydrous magnesium sulfate, and the solvent was evaporated under reduced pressure to give crystals. The obtained crystals, reduced iron (19.5 g) and calcium chloride (3.9 g) in a mixed solvent of ethanol (500 mL) and water (70 mL) was stirred at 90° C. for 4 hr with heating. The reaction mixture was filtered, and the solvent was evaporated under reduced pressure. Water was added, and the mixture was extracted with ethyl acetate. The organic layer was washed with saturated brine and dried over anhydrous magnesium sulfate, and the solvent was evaporated under reduced pressure. To the obtained residue were added morpholine (26.2 mL), 2-dimethylaminomethylene-1,3-bis(dimethylimmonio)propane bistetrafluoroborate (35.7 g) and 1-butanol (300 ml), and the mixture was stirred at 90° C. for 24 hr. To the reaction mixture were added acetic acid (50 mL) and water (50 mL), and the mixture was stirred at room temperature for 4 hr. The precipitated crystals were collected by filtration, washed with acetic acid and water, and dried to give the title compound (7.0 g, yield 23%) as brown crystals.
$^1$H NMR (300 MHz, DMSO-$d_6$) δ: 1.66-1.75 (1H, m), 1.82-1.94 (2H, m), 1.98-2.06 (1H, m), 2.69 (3H, s), 3.69 (1H, q, J=6.0 Hz), 3.78 (1H, q, J=6.0 Hz), 3.99-4.11 (2H, m), 4.16-4.21 (1H, m), 7.10 (2H, d, J=8.7 Hz), 7.81 (1H, d, J=8.7 Hz), 8.01-8.07 (3H, m), 8.92 (1H, d, J=2.1 Hz), 9.30 (1H, d, J=2.1 Hz), 10.18 (1H, s), 10.25 (1H, s).

Reference Example 3

4-(tetrahydrofuran-3-ylmethoxy)benzoic acid

To a solution of tetrahydrofuran-3-ylmethanol (21.89 g), methyl 4-hydroxybenzoate (33.5 g) and triphenylphosphine (64.5 g) in tetrahydrofuran (400 ml) was slowly added dropwise a solution of diethyl azodicarboxylate in toluene (120 mL, 40% toluene solution) at 0° C., and the mixture was stirred at room temperature for 2 hr. The reaction solution was concentrated, triphenylphosphine oxide was precipitated from ethyl acetate-hexane and removed by filtration with a glass filter, and the mother liquor was concentrated. The residue was purified by silica gel column chromatography [developing solvent; hexane:ethyl acetate=90:10 (volume ratio)-*hexane:ethyl acetate=40:10 (volume ratio)] to give a colorless oil. The obtained colorless oil was dissolved in tetrahydrofuran (200 mL) and methanol (100 mL), 8N aqueous sodium hydroxide solution (100 mL) was added, and the mixture was stirred at 80° C. for 2 hr with heating. The reaction solution was concentrated, cooled to 0° C., neutralized with 6N hydrochloric acid, and extracted with ethyl acetate. The organic layer was washed with saturated brine and dried over anhydrous magnesium sulfate, and the solvent was evaporated under reduced pressure to give the title compound (23 g, yield 48%) as colorless crystals.

$^1$H NMR (300 MHz, DMSO-$d_6$) δ: 1.61-1.71 (1H, m), 1.97-2.08 (1H, m), 2.60-2.73 (1H, m), 3.48-3.56 (1H, m), 3.62-3.69 (1H, m), 3.73-3.82 (2H, m), 3.88-4.04 (2H, m), 7.02 (2H, d, J=9.3 Hz), 7.88 (2H, d, J=9.3 Hz), 12.59 (1H, br).

Reference Example 4

N-(3-formyl-8-methylquinolin-7-yl)-4-(tetrahydrofuran-3-ylmethoxy)benzamide 4-(Tetrahydrofuran-3-ylmethoxy)benzoic acid (22.2 g) obtained in Reference Example 3, oxalyl dichloride (10.2 mL) and N,N-dimethylformamide (2 drops) were mixed with tetrahydrofuran (250 mL), and the mixture was stirred at room temperature for 3 hr. The reaction mixture was concentrated under reduced pressure, and tetrahydrofuran (200 mL) was added to the concentration residue. To this mixture was added under ice-cooling a solution of 2-methyl-3-nitroaniline (14.1 g) and triethylamine (16.7 mL) in tetrahydrofuran (100 mL), and the mixture was stirred at room temperature for 24 hr. Water was added to the reaction mixture, and the mixture was extracted with ethyl acetate. The organic layer was washed with saturated brine and dried over anhydrous magnesium sulfate, and the solvent was evaporated under reduced pressure to give crystals. A solution of the obtained crystals, reduced iron (26.0 g) and calcium chloride (5.6 g) in a mixed solvent of ethanol (500 mL) and water (50 mL) was stirred with heating at 90° C. for 16 hr. The reaction mixture was filtered, and the solvent was evaporated under reduced pressure. Water was added, and the mixture was extracted with ethyl acetate. The organic layer was washed with saturated brine and dried over anhydrous magnesium sulfate, and the solvent was evaporated under reduced pressure. To the obtained residue were added morpholine (26.2 mL), 2-dimethylaminomethylene-1,3-bis(dimethylimmonio)propane bistetrafluoroborate (35.7 g) and 1-butanol (300 mL), and the mixture was stirred at 90° C. for 24 hr. To the reaction mixture were added acetic acid (50 mL) and water (50 mL), and the mixture was stirred at room temperature for 4 hr. The precipitated crystals were washed with acetic acid and water, collected by filtration, and dried to give the title compound (18.0 g, yield 50%) as brown crystals.

FABMS (pos): 391 [MH]$^+$

Reference Example 5

4-[(2R)-tetrahydrofuran-2-ylmethoxy]benzoic acid

A solution of (2R)-tetrahydrofuran-2-carboxylic acid (23.2 g) in toluene (240 mL) and methanol (80 mL) was cooled to 0° C., and (trimethylsilyl)diazomethane (100 mL, 2.0M hexane solution) was slowly added dropwise. After the completion of the dropwise addition, the mixture was stirred at 0° C. for 30 min. The reaction solution was concentrated, and tetrahydrofuran (500 mL) was added to the residue. The reaction solution was cooled to 0° C., aluminum lithium hydride (100 mL, 2.0M tetrahydrofuran solution) was slowly added dropwise. After the completion of the dropwise addition, the mixture was stirred at 0° C. for 2 hr. To the reaction solution was slowly added sodium sulfate decahydrate at 0° C. carefully until foaming ceased, and the mixture was stirred at room temperature for 2 hr. The reaction solution was filtered through celite to remove insoluble materials, and the solvent was evaporated under reduced pressure to give a colorless liquid (18.0 g). To a solution of the obtained colorless liquid (18.0 g), methyl 4-hydroxybenzoate (27.4 g), and triphenylphosphine (53.2 g) in tetrahydrofuran (400 ml) was slowly added dropwise a solution (99 mL) of diethyl azodicarboxylate in toluene (40% toluene solution) at 0° C., and the mixture was stirred at room temperature for 2 hr. The reaction solution was concentrated, triphenylphosphine oxide was precipitated from ethyl acetate-hexane and removed by filtration with a glass filter, and the mother liquor was concentrated. The residue was purified by NH-silica gel column chromatography [developing solvent; hexane:ethyl acetate=100:0 (volume ratio)→hexane:ethyl acetate=90:10 (volume ratio)] to give a colorless oil. The obtained colorless oil was dissolved in tetrahydrofuran (200 mL) and methanol (200 ml), 8N aqueous sodium hydroxide solution (100 mL) was added, and the mixture was stirred at 80° C. for 2 hr with heating. The reaction solution was concentrated, cooled to 0° C., neutralized with 6N hydrochloric acid, and extracted with ethyl acetate. The organic layer was washed with saturated brine and dried over anhydrous magnesium sulfate, and the solvent was evaporated under reduced pressure to give the title compound (38.6 g, yield 87%) as colorless crystals.

$^1$H NMR (300 MHz, DMSO-$d_6$) δ: 1.61-1.72 (1H, m), 1.75-1.92 (2H, m), 1.94-2.06 (1H, m), 3.67 (1H, q, J=6.3 Hz), 3.77 (1H, q, J=6.3 Hz), 3.81-4.06 (2H, m), 4.12-4.20 (1H, m), 7.01 (2H, d, J=9.0 Hz), 7.87 (2H, d, J=8.4 Hz), 12.60 (1H, s).

Reference Example 6

N-(3-formyl-8-methylquinolin-7-yl)-4-[(2R)-tetrahydrofuran-2-ylmethoxy]benzamide 4-[(2R)-Tetrahydrofuran-2-ylmethoxy]benzoic acid (38.3 g) obtained in Reference Example 5, oxalyl dichloride (17.5 mL) and N,N-dimethylformamide (3 drops) were mixed with tetrahydrofuran (250 mL), and the mixture was stirred at room temperature for 2 hr. The reaction mixture was concentrated under reduced pressure, and tetrahydrofuran (300 mL) was added to the concentration residue. To this mixture was added a solution of 2-methyl-3-nitroaniline (25 g) and triethylamine (28.7 mL) in tetrahydrofuran (100 mL) under ice-cooling, and the mixture was stirred at room temperature for 24 hr. Water was added to the reaction mixture, and the mixture was extracted with ethyl acetate. The organic layer was washed with saturated brine and dried over anhydrous magnesium sulfate, and the solvent was evaporated under reduced pressure to give crystals. To a solution of the obtained crystals in methanol (500 mL) and tetrahydrofuran (200 mL) was added palladium carbon (1.5 g), and the mixture was stirred under a hydrogen atmosphere at room temperature for 4 hr. After completion of the reaction, the solvent was evaporated under reduced pressure. To the obtained residue were added morpholine (78 mL), 2-dimethylaminomethylene-1,3-bis(dimethylimmonio)propane bistetrafluoroborate (107 g)

and 1-butanol (500 mL), and the mixture was stirred at 80° C. for 14 hr. To the reaction mixture were added acetic acid (70 mL) and water (80 mL), and the mixture was stirred at room temperature for 2 hr. The reaction mixture was extracted with ethyl acetate, and the organic layer was purified by silica gel column chromatography [developing solvent; ethyl acetate] to give the title compound (54 g, yield 81%) as brown crystals.

$^1$H NMR (300 MHz, DMSO-$d_6$) δ: 1.66-1.75 (1H, m), 1.81-1.94 (2H, m), 1.98-2.04 (1H, m), 2.69 (3H, s), 3.68 (1H, q, J=6.3 Hz), 3.78 (1H, q, J=6.3 Hz), 3.99-4.10 (2H, m), 4.17-4.21 (1H, m), 7.08-7.12 (2H, m), 7.81 (1H, d, J=8.7 Hz), 8.01-8.06 (3H, m), 8.91 (1H, d, J=2.4 Hz), 9.30 (1H, d, J=2.4 Hz), 10.17 (1H, s), 10.24 (1H, s).

Reference Example 7

(2S)-tetrahydrofurfurylalcohol

A solution of (2S)-tetrahydrofuran-2-carboxylic acid (46.4 g) in toluene (480 mL) and methanol (160 mL) was cooled to 0° C., and (trimethylsilyl)diazomethane (200 mL, 2.0M hexane solution) was slowly added dropwise. After the completion of the dropwise addition, the mixture was stirred at 0° C. for 30 min. The reaction solution was concentrated, and tetrahydrofuran (500 mL) was added to the residue. The reaction solution was cooled to 0° C., aluminum lithium hydride (200 mL, 2.0M tetrahydrofuran solution) was slowly added dropwise. After the completion of the dropwise addition, the mixture was stirred at 0° C. for 2 hr. To the reaction solution was slowly added sodium sulfate decahydrate at 0° C. carefully until foaming ceased, and the mixture was stirred at room temperature for 2 hr. The reaction solution was filtered through celite to remove insoluble materials, and the solvent was evaporated under reduced pressure to give the title compound (28.7 g, yield 70%) as a colorless oil.

$^1$H NMR (300 MHz, CDCl$_3$) δ: 1.62-1.70 (1H, m), 1.85-1.99 (3H, m), 2.56-2.62 (1H, m), 3.46-3.54 (1H, m), 3.63-3.70 (1H, m), 3.74-3.90 (2H, m), 3.97-4.05 (1H, m).

Reference Example 8

4-[(2S)-tetrahydrofuran-2-ylmethoxy]benzoic acid

To a solution of (2S)-tetrahydrofurfuryl alcohol (28.7 g) obtained in Reference Example 7, methyl 4-hydroxybenzoate (44 g) and triphenylphosphine (85 g) in tetrahydrofuran (400 mL) was slowly added dropwise a solution (99 mL) of diethyl azodicarboxylate in toluene (40% toluene solution) at 0° C., and the mixture was stirred at room temperature for 2 hr. The reaction solution was concentrated, triphenylphosphine oxide was precipitated from ethyl acetate-hexane and removed by filtration with a glass filter, and the mother liquor was concentrated. The residue was purified by NH-silica gel column chromatography [developing solvent; hexane:ethyl acetate=100:0 (volume ratio)→hexane:ethyl acetate=90:10 (volume ratio)] to give a colorless oil. The obtained colorless oil was dissolved in tetrahydrofuran (400 mL) and methanol (200 mL), 8N aqueous sodium hydroxide solution (120 mL) was added, and the mixture was stirred at 80° C. for 2 hr with heating. The reaction solution was concentrated, cooled to 0° C., neutralized with 6N hydrochloric acid, and extracted with ethyl acetate. The organic layer was washed with saturated brine and dried over anhydrous magnesium sulfate, and the solvent was evaporated under reduced pressure to give the title compound (47 g, yield 75%) as colorless crystals.

$^1$H NMR (300 MHz, DMSO-$d_6$) δ: 1.64-1.72 (1H, m), 1.82-1.92 (2H, m), 1.95-2.04 (1H, m), 3.68 (1H, q, J=7.2 Hz), 3.78 (1H, q, J=7.2 Hz), 3.95-4.06 (2H, m), 4.14-4.19 (1H, m), 7.02 (2H, d, J=8.7 Hz), 7.88 (2H, d, J=8.4 Hz), 12.62 (1H, s).

Reference Example 9

N-(3-formyl-8-methylquinolin-7-yl)-4-[(2S)-tetrahydrofuran-2-ylmethoxy]benzamide 4-[(2S)-Tetrahydrofuran-2-ylmethoxy]benzoic acid (45 g) obtained in Reference Example 8, oxalyl dichloride (19.5 mL) and N,N-dimethylformamide (0.50 mL) were mixed with tetrahydrofuran (280 mL), and the mixture was stirred at room temperature for 2 hr. The reaction mixture was concentrated under reduced pressure, and tetrahydrofuran (300 mL) was added to the concentration residue. To this mixture was added under ice-cooling a solution of 2-methyl-3-nitroaniline (29.5 g) and triethylamine (32 mL) in tetrahydrofuran (100 mL), and the mixture was stirred at room temperature for 24 hr. Water was added to the reaction mixture, and the mixture was extracted with ethyl acetate. The organic layer was washed with saturated brine and dried over anhydrous magnesium sulfate, and the solvent was evaporated under reduced pressure to give crystals. To a solution of the obtained crystals in methanol (600 mL) was added palladium carbon (3.0 g), and the mixture was stirred under a hydrogen atmosphere at room temperature for 4 hr. After completion of the reaction, the solvent was evaporated under reduced pressure. To the obtained residue were added morpholine (102 mL), 2-dimethylaminomethylene-1,3-bis(dimethylimmonio)propane bistetrafluoroborate (139 g) and 1-butanol (500 mL), and the mixture was stirred at 80° C. for 14 hr. To the reaction mixture were added acetic acid (70 mL) and water (80 mL), and the mixture was stirred at room temperature for 2 hr. The reaction mixture was extracted with ethyl acetate, and the organic layer was purified by silica gel column chromatography [developing solvent; ethyl acetate] to give the title compound (50 g, yield 66%) as brown crystals.

$^1$H NMR (300 MHz, DMSO-$d_6$) δ: 1.69-1.75 (1H, m), 1.84-1.94 (2H, m), 1.98-2.07 (1H, m), 2.69 (3H, s), 3.69 (1H, q, J=6.6 Hz), 3.79 (1H, q, J=6.6 Hz), 3.99-4.10 (2H, m), 4.15-4.22 (1H, m), 7.10 (2H, d, J=8.7 Hz), 7.82 (1H, d, J=8.7 Hz), 8.02-8.05 (3H, m), 8.89 (1H, d, J=2.1 Hz), 9.29 (1H, d, J=2.4 Hz), 10.17 (1H, s), 10.24 (1H, s).

Reference Example 10 methyl 2-fluoro-4-hydroxybenzoate

A solution of 2-fluoro-4-hydroxybenzoic acid (50.0 g) and concentrated sulfuric acid (10 mL) in methanol (700 mL) was stirred at 90° C. for 16 hr with heating. The reaction solution was concentrated, and the resulting colorless crystals were washed with water, and dried to give the title compound (51 g, yield 94%) as colorless crystals.

$^1$H NMR (300 MHz, DMSO-$d_6$) δ: 3.79 (3H, s), 6.61-6.72 (2H, m), 7.73-7.79 (1H, m), 10.80 (1H, br).

Reference Example 11

2-fluoro-4-[(2S)-tetrahydrofuran-2-ylmethoxy]benzoic acid

To a solution of (2S)-tetrahydrofurfuryl alcohol (30.0 g) obtained in Reference Example 7, methyl 2-fluoro-4-hydroxybenzoate (50.0 g) obtained in Reference Example 10 and triphenylphosphine (88.9 g) in tetrahydrofuran (350 mL) was slowly added dropwise a solution (166 mL) of diethyl azodicarboxylate in toluene (40% toluene solution) at 0° C., and the mixture was stirred at room temperature for 2 hr. The reaction solution was concentrated, triphenylphosphine oxide was precipitated from ethyl acetate-hexane and removed by filtration with a glass filter, and the mother liquor was concentrated. The residue was purified by NH-silica gel column chromatography [developing solvent; hexane:ethyl acetate=95:5 (volume ratio)→hexane:ethyl acetate=90:10 (volume ratio)] to give colorless crystals. The obtained colorless crystals were dissolved in tetrahydrofuran (500 mL), 8N aqueous sodium hydroxide solution (100 mL) was added, and the mixture was stirred at 60° C. for 3 hr with heating. The reaction solution was concentrated, cooled to 0° C., neutralized with 6N hydrochloric acid, and extracted with ethyl acetate. The organic layer was washed with saturated brine and dried over anhydrous magnesium sulfate, and the solvent was evaporated under reduced pressure to give the title compound (60.0 g, yield 85%) as colorless crystals.

$^1$H NMR (300 MHz, DMSO-$d_6$) δ: 1.60-1.71 (1H, m), 1.75-1.92 (2H, m), 1.94-2.06 (1H, m), 3.69 (1H, q, J=6.9 Hz), 3.77 (1H, q, J=6.9 Hz), 3.96-4.09 (2H, m), 4.12-4.20 (1H, m), 6.84-6.92 (2H, m), 7.78-7.84 (1H, m), 12.85 (1H, br).

Reference Example 12

2-fluoro-N-(3-formyl-8-methylquinolin-7-yl)-4-[(2S)-tetrahydrofuran-2-ylmethoxy]benzamide 2-Fluoro-4-[(2S)-tetrahydrofuran-2-ylmethoxy]benzoic acid (11.0 g) obtained in Reference Example 11, oxalyl dichloride (4.74 mL) and N,N-dimethylformamide (0.50 mL) were mixed with tetrahydrofuran (200 mL), and the mixture was stirred at room temperature for 3 hr. The reaction mixture was concentrated under reduced pressure, and tetrahydrofuran (200 mL) was added to the concentration residue. To this mixture was added under ice-cooling a solution of 2-methyl-3-nitroaniline (6.85 g) and triethylamine (8.36 mL) in tetrahydrofuran (100 mL), and the mixture was stirred at room temperature for 24 hr. Water was added to the reaction mixture, and the mixture was extracted with ethyl acetate. The organic layer was washed with saturated brine and dried over anhydrous magnesium sulfate, and the solvent was evaporated under reduced pressure to give crystals. To a solution of the obtained crystals in methanol (750 mL) was added palladium carbon (1.0 g), and the mixture was stirred under a hydrogen atmosphere at room temperature for 4 hr. After completion of the reaction, the solvent was evaporated under reduced pressure. To the obtained residue were added morpholine (23 mL), 2-dimethylaminomethylene-1,3-bis(dimethylimmonio)propane bistetrafluoroborate (30.0 g) and 1-butanol (300 mL), and the mixture was stirred at 80° C. for 14 hr. To the reaction mixture were added acetic acid (20 mL) and water (20 mL), and the mixture was stirred at room temperature for 2 hr. The reaction mixture was extracted with ethyl acetate. The organic layer was washed with saturated brine and dried over anhydrous magnesium sulfate, and the solvent was evaporated under reduced pressure to give the title compound (16 g, yield 87%) as pale-brown crystals.

$^1$H NMR (300 MHz, DMSO-$d_6$) δ: 1.64-1.73 (1H, m), 1.83-1.93 (2H, m), 1.97-2.05 (1H, m), 2.72 (3H, s), 3.71 (1H, q, J=6.3 Hz), 3.79 (1H, q, J=6.3 Hz), 4.00-4.09 (2H, m), 4.11-4.20 (1H, m), 6.93-7.04 (2H, m), 7.77 (1H, d, J=8.7 Hz), 7.97-8.08 (2H, m), 8.91 (1H, s), 9.29 (1H, s), 10.03 (1H, s), 10.24 (1H, s).

Reference Example 13 benzyl(cis-4-hydroxy-4-methylcyclohexyl)carbamate benzyl(trans-4-hydroxy-4-methylcyclohexyl)carbamate Under a nitrogen atmosphere, benzyl (4-oxocyclohexyl)carbamate (201 mg) was dissolved in THF (15 mL), and the mixture was cooled to −78° C. A solution (1.5M, 1.63 mL) of methyllithium-lithium bromide complex in THF was added dropwise at the same temperature, and the mixture was stirred for 3.5 hr. A saturated aqueous ammonium chloride solution was added, and the mixture was heated to room temperature, and partitioned and extracted with ethyl acetate. The organic layer was washed with water and saturated brine, and concentrated under reduced pressure. The residue was purified by silica gel column chromatography [developing solvent; hexane:ethyl acetate=8:2 (volume ratio)→hexane:ethyl acetate=7:13 (volume ratio)] to give the title compound (cis form 133 mg, yield 62%) as a colorless oil, and the title compound (trans form 33.9 mg, yield 16%) as a colorless oil.

cis form: $^1$H NMR (300 MHz, CDCl$_3$) δ: 1.09 (1H, br. s.), 1.23 (3H, s), 1.41-1.71 (6H, m), 1.74-1.88 (2H, m), 3.48 (1H, br. s.), 4.65 (1H, br. s.), 5.09 (2H, s), 7.28-7.39 (5H, m).

trans form: $^1$H NMR (300 MHz, CDCl$_3$) δ: 1.19-1.30 (4H, m), 1.31-1.47 (2H, m), 1.47-1.70 (4H, m), 1.88-2.03 (2H, m), 3.57-3.72 (1H, m), 4.69 (1H, br. s.), 5.09 (2H, s), 7.29-7.40 (5H, m).

Reference Example 14 cis-4-amino-1-methylcyclohexanol

Benzyl(cis-4-hydroxy-4-methylcyclohexyl)carbamate (28.76 g) obtained in Reference Example 13 and activated carbon-supported palladium hydroxide (Pd:20%, 2.876 g) were mixed in a mixed solvent of THF (100 mL) and methanol (100 mL), and the mixture was stirred under a hydrogen atmosphere at 1 atm for 15 hr. The reaction solution was filtered through celite, and the filtrate was concentrated under reduced pressure. The residue was suspended in ethyl acetate, and the precipitate was collected by filtration, washed with ethyl acetate, and dried under reduced pressure to give the title compound (13.67 g, yield 95%) as a colorless solid.

$^1$H NMR (300 MHz, DMSO-$d_6$) δ: 1.06 (3H, s), 1.17-1.57 (8H, m), 2.42-2.47 (1H, m).

Reference Example 15 trans-4-amino-1-methylcyclohexanol

Benzyl(trans-4-hydroxy-4-methylcyclohexyl)carbamate (100 g) obtained in Reference Example 13 and palladium carbon (Pd:5%, 10 g) were mixed in methanol (1 L), and the mixture was stirred under a hydrogen atmosphere for 18 hr. The insoluble material was filtered off, and the filtrate was concentrated under reduced pressure to give the title compound (49.3 g, yield 100%) as a colorless solid.

$^1$H NMR (300 MHz, CDCl$_3$) δ: 1.18-1.87 (14H, m), 2.76-2.87 (1H, m).

Reference Example 16 benzyl 4-hydroxy-4-methylpiperidine-1-carboxylate

Methylmagnesium chloride (9.53 mL, 3.0M tetrahydrofuran solution) was added to tetrahydrofuran (45.5 mL). Benzyl 4-oxopiperidine-1-carboxylate (5.00 g) was dissolved in tetrahydrofuran (8.8 mL), and added dropwise to a solution of ice-cooled methylmagnesium chloride in tetrahydrofuran, and the mixture was stirred at room temperature for 14 hr. The reaction mixture was ice-cooled, aqueous ammonium chloride solution (ammonium chloride 1.41 g, water 15 mL) was added dropwise, and the mixture was partitioned and extracted with ethyl acetate. The aqueous layer was extracted with ethyl acetate, and the combined organic layer was dried over magnesium sulfate, and purified by NH-silica gel column chromatography [developing solvent; hexane:ethyl acetate=80:20 (volume ratio)→60:40 (volume ratio)]. The obtained solid was washed with isopropyl ether, and dried under reduced pressure to give the title compound (4.20 g, yield 79%) as a colorless solid.

$^1$H NMR (300 MHz, DMSO-$d_6$) δ: 1.12 (3H, s), 1.31-1.52 (4H, m), 3.20 (2H, br. s), 3.63 (2H, dt, J=13.0, 3.9 Hz), 4.35 (1H, s), 5.06 (2H, s), 7.26-7.54 (5H, m)

Reference Example 17

4-methylpiperidin-4-ol monohydrochloride

Benzyl 4-hydroxy-4-methylpiperidine-1-carboxylate (6.28 g) was dissolved in methanol (125 ml), 10% palladium carbon (900 mg) was added, and the mixture was stirred under a hydrogen atmosphere at room temperature for 14 hr. Insoluble materials were filtered off, and the filtrate was concentrated under reduced pressure. The residue was diluted with methanol (25 ml), and 1N hydrochloric acid (25.2 ml) was added. The mixture was concentrated under reduced pressure, and the obtained solid was washed with acetone and dried under reduced pressure to give the title compound (3.57 g, 93%) as a colorless solid.

$^1$H NMR (300 MHz, DMSO-$d_6$) δ: 1.16 (3H, s), 1.54-1.74 (4H, m), 2.95-3.08 (4H, m), 4.70 (1H, s), 8.90 (1H, s), 9.00 (1H, s).

Example 1

N-(3-{[(2-hydroxy-2-methylpropyl)amino]methyl}-8-methylquinolin-7-yl)-4-(tetrahydrofuran-2-ylmethoxy)benzamide

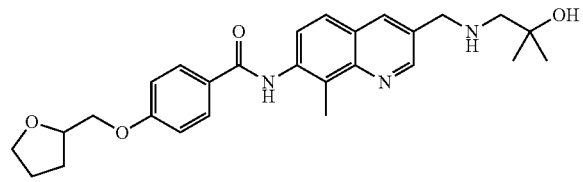

N-(3-Formyl-8-methylquinolin-7-yl)-4-(tetrahydrofuran-2-ylmethoxy)benzamide (1.0 g) obtained in Reference Example 2 and 1-amino-2-methylpropan-2-ol (321 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (280 mg, yield 24%) as a colorless solid.

$^1$H NMR (300 MHz, DMSO-$d_6$) δ: 1.12 (6H, s), 1.66-1.75 (1H, m), 1.83-1.92 (2H, m), 1.94-2.05 (1H, m), 2.42 (2H, s), 2.64 (3H, s), 3.33 (1H, br), 3.66-3.73 (1H, m), 3.77-3.84 (1H, m), 3.94 (2H, s), 3.98-4.10 (2H, m), 4.15-4.22 (2H, m), 7.08 (2H, d, J=9.0 Hz), 7.58 (1H, d, J=8.7 Hz), 7.77 (1H, d, J=8.7 Hz), 8.02 (2H, d, J=9.0 Hz), 8.19 (1H, s), 8.90 (1H, s), 10.05 (1H, s).

melting point: 138° C.

elemental analysis value ($C_{27}H_{33}N_3O_4$·0.25$H_2O$)

Calculated: C, 69.28; H, 7.21; N, 8.98.

Found: C, 69.26; H, 7.13; N, 8.68.

Example 2

N-(3-{[(trans-4-hydroxycyclohexyl)amino]methyl}-8-methylquinolin-7-yl)-4-(tetrahydrofuran-2-ylmethoxy)benzamide

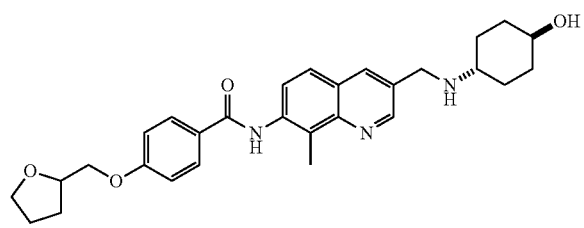 [SMILES: Cc1c(NC(=O)c2ccc(OCC3CCCO3)cc2)ccc2cc(CN[C@H]3CC[C@H](O)CC3)cnc12]

N-(3-Formyl-8-methylquinolin-7-yl)-4-(tetrahydrofuran-2-ylmethoxy)benzamide (1.0 g) obtained in Reference Example 2 and trans-4-aminocyclohexanol (415 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (130 mg, yield 10%) as a colorless solid.

$^1$H NMR (300 MHz, DMSO-$d_6$) δ: 1.01-1.14 (4H, m), 1.72-2.01 (9H, m); 2.10-2.37 (2H, m), 2.63 (3H, s), 3.68-3.71 (1H, m), 3.79-3.81 (1H, m), 3.91 (2H, s), 4.00-4.10 (2H, m), 4.17-4.19 (1H, m), 4.45 (1H, s), 7.08 (2H, d, J=8.4 Hz), 7.57 (1H, d, J=8.7 Hz), 7.77 (1H, d, J=8.7 Hz), 8.01 (2H, d, J=8.4 Hz), 8.19 (1H, s), 8.88 (1H, s), 10.04 (1H, s).

melting point: 155° C.

Example 3

N-[3-({[(1S,2S)-2-hydroxycyclohexyl]amino}methyl)-8-methylquinolin-7-yl]-4-(tetrahydrofuran-2-ylmethoxy)benzamide

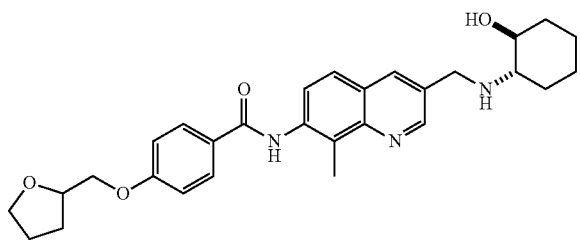

N-(3-Formyl-8-methylquinolin-7-yl)-4-(tetrahydrofuran-2-ylmethoxy)benzamide (1.0 g) obtained in Reference Example 2% and trans-2-aminocyclohexanol (546 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (395 mg, yield 32%) as a colorless solid.

$^1$H NMR (300 MHz, DMSO-$d_6$) δ: 0.98-1.23 (4H, m), 1.59-2.08 (9H, m), 2.22-2.29 (1H, m), 2.64 (3H, s), 3.17-3.19 (1 H, m), 3.66-3.91 (3H, m), 3.98-4.10 (3H, m), 4.15-4.23 (1H, m), 4.64 (1H, d, J=4.8 Hz), 7.08 (2H, d, J=9.0 Hz), 7.57 (1H, d, J=9.0 Hz), 7.77 (1H, d, J=9.0 Hz), 8.01 (2H, d, J=9.0 Hz), 8.21 (1H, s), 8.89 (1H, s), 10.04 (1H, s).

melting point: 197° C.

elemental analysis value ($C_{29}H_{35}N_3O_4 \cdot 0.2H_2O$)

Calculated: C, 70.62; H, 7.23; N, 8.52.

Found: C, 70.81; H, 7.28; N, 8.31.

Example 4

N-[3-({[(1S,2S)-2-hydroxycyclopentyl]amino}methyl)-8-methylquinolin-7-yl]-4-(tetrahydrofuran-2-ylmethoxy)benzamide

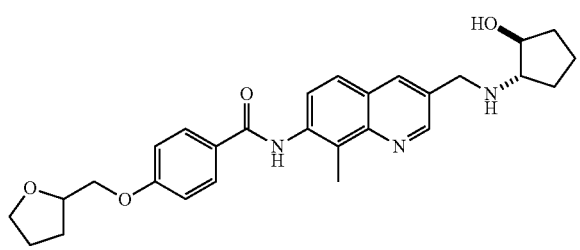 [SMILES: Cc1c(NC(=O)c2ccc(OCC3CCCO3)cc2)ccc2cc(CN[C@H]3CCC[C@@H]3O)cnc12]

N-(3-Formyl-8-methylquinolin-7-yl)-4-(tetrahydrofuran-2-ylmethoxy)benzamide (1.3 g) obtained in Reference Example 2 and (1S,2S)-2-aminocyclopentanol (633 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture, and the mixture was partitioned and extracted with ethyl acetate. The organic layer was washed with saturated brine and dried over anhydrous sodium sulfate, and the solvent was evaporated under reduced pressure. The residue was purified by silica gel column chromatography [developing solvent; methanol:ethyl acetate=0:100 (volume ratio)→methanol:ethyl acetate=20:80 (volume ratio)] to give the title compound (59.2 mg, yield 4%) as a colorless solid.

$^1$H NMR (300 MHz, DMSO-$d_6$) δ: 1.29-1.46 (3H, m), 1.53-1.63 (2H, m), 1.66-1.76 (1H, m), 1.77-1.94 (3H, m), 1.98-2.06 (1H, m), 2.23 (1H, br), 2.63 (3H, s), 2.78-2.81 (1H, m), 3.66-3.73 (1H, m), 3.77-3.84 (2H, m), 3.92 (2H, s), 3.98-4.10 (2H, m), 4.15-4.21 (1H, m), 4.51 (1H, d, J=4.2 Hz), 7.08 (2H, d, J=8.7 Hz), 7.57 (1H, d, J=8.4 Hz), 7.77 (1H, d, J=8.4 Hz), 8.01 (2H, d, J=8.7 Hz), 8.20 (1H, s), 8.89 (1H, s), 10.03 (1H, s).

elemental analysis value ($C_{28}H_{33}N_3O_4$)

Calculated: C, 70.71; H, 6.99; N, 8.84.

Found: C, 70.48; H, 7.02; N, 8.68.

Example 5

N-(3-{[(2-methoxy-2-methylpropyl)amino]methyl}-8-methylquinolin-7-yl)-4-(tetrahydrofuran-2-ylmethoxy)benzamide monohydrochloride

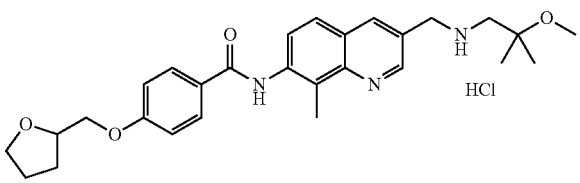 [SMILES: COC(C)(C)CNCc1cnc2c(C)c(NC(=O)c3ccc(OCC4CCCO4)cc3)ccc2c1 ; Cl]

N-(3-Formyl-8-methylquinolin-7-yl)-4-(tetrahydrofuran-2-ylmethoxy)benzamide (1.0 g) obtained in Reference Example 2 and 2-methoxy-2-methylpropan-1-amine 0.5 oxalate (600 mg) were suspended in 1-methyl-2-pyrrolidone (10 mL) and acetic acid (5.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained amorphous product was dissolved in ethyl acetate, and 4N hydrogen chloride-ethyl acetate solution (0.15 mL) was added. The obtained solid was recrystallized from ethyl acetate-methanol to give the title compound (101 mg, yield 8%) as a colorless solid.

¹H NMR (300 MHz, DMSO-d₆) δ: 1.20 (6H, s), 1.68-1.72 (1H, m), 1.87-1.90 (2H, m), 1.96-2.00 (2H, m), 2.68 (3H, s), 2.97-3.00 (1H, m), 3.11 (3H, s), 3.68-3.81 (2H, m), 4.02-4.06 (2H, m), 4.16-4.20 (1H, m), 4.42 (2H, s), 7.09 (2H, d, J=8.7 Hz), 7.75 (1H, d, J=8.7 Hz), 7.90 (1H, d, J=8.7 Hz), 8.04 (2H, d, J=8.7 Hz), 8.72 (1H, s), 9.20 (1H, s), 9.27 (2H, br), 10.25 (1H, s).

Example 6

N-(3-{[(2-hydroxy-2-methylpropyl)amino]methyl}-8-methylquinolin-7-yl)-4-(tetrahydrofuran-3-yl-methoxy)benzamide

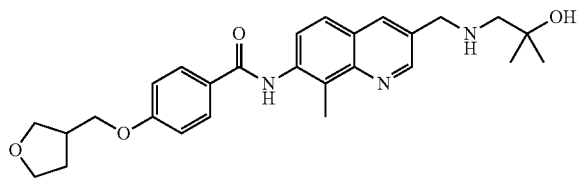 [SMILES: Cc1c(NC(=O)c2ccc(OCC3CCOC3)cc2)ccc2cc(CNCC(C)(C)O)cnc12]

N-(3-Formyl-8-methylquinolin-7-yl)-4-(tetrahydrofuran-3-ylmethoxy)benzamide (1.1 g) obtained in Reference Example 4 and 1-amino-2-methylpropan-2-ol (351 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture, and the mixture was partitioned and extracted with ethyl acetate. The organic layer was washed with saturated brine and dried over anhydrous sodium sulfate, and the solvent was evaporated under reduced pressure. The residue was purified by silica gel column chromatography [developing solvent; methanol:ethyl acetate=0:100 (volume ratio)→methanol:ethyl acetate=20:80 (volume ratio)] to give the title compound (58 mg, yield 4%) as a colorless solid.

¹H NMR (300 MHz, DMSO-d₆) δ: 1.11 (6H, s), 1.66-1.72 (1H, m), 1.99-2.08 (1H, m), 2.31 (1H, br), 2.48 (2H, s), 2.64% (3H, s), 2.69-2.72 (1H, m), 3.54-3.58 (1H, m), 3.63-3.71 (1H, m), 3.75-3.84 (2H, m), 3.94 (2H, s), 3.99-4.08 (2H, m), 4.21 (1H, s), 7.09 (2H, d, J=8.4 Hz), 7.57 (1 H, d, J=8.7 Hz), 7.77 (1H, d, J=8.7 Hz), 8.02 (2H, d, J=8.4 Hz), 8.20 (1H, s), 8.91 (1H, s), 10.05 (1H, s).

elemental analysis value (C₂₇H₃₃N₃O₄.0.75H₂O)
Calculated: C, 67.97; H, 7.29; N, 8.81.
Found: C, 67.85; H, 6.90; N, 8.43.

Example 7

N-(8-methyl-3-{[(1-methylethyl)amino]methyl}quinolin-7-yl)-4-(tetrahydrofuran-3-yl-methoxy)benzamide

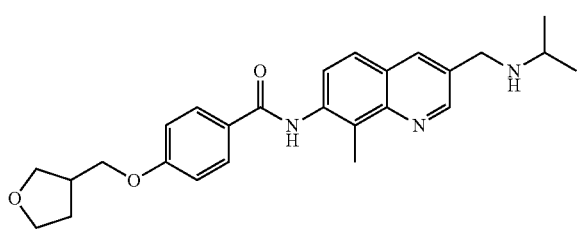 [SMILES: Cc1c(NC(=O)c2ccc(OCC3CCOC3)cc2)ccc2cc(CNC(C)C)cnc12]

N-(3-Formyl-8-methylquinolin-7-yl)-4-(tetrahydrofuran-3-ylmethoxy)benzamide (1.1 g) obtained in Reference Example 4 and isopropylamine (233 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (789 mg, yield 65%) as a colorless solid.

¹H NMR (300 MHz, DMSO-d₆) δ: 1.04 (6H, d, J=6.0 Hz), 1.67-1.71 (1H, m), 2.03-2.07 (1H, m), 2.50-2.54 (2H, m), 2.63 (3H, s), 2.69-2.77 (2H, m), 3.54-3.58 (1H, m), 3.66-3.71 (1H, m), 3.79-3.84 (2H, m), 3.89-4.04 (3H, m), 7.08 (2H, d, J=8.4 Hz), 7.57 (1H, d, J=8.7 Hz), 7.77 (1H, d, J=8.7 Hz), 8.02 (2H, d, J=8.4 Hz), 8.20 (1H, s), 8.89 (1H, s), 10.04 (1H, s).

melting point: 106° C.
elemental analysis value (C₂₆H₃₁N₃O₃.3.0H₂O)
Calculated: C, 64.05; H, 7.65; N, 8.62.
Found: C, 64.03; H, 7.38; N, 8.31.

Example 8

N-{8-methyl-3-[(tetrahydro-2H-pyran-4-ylamino)methyl]quinolin-7-yl}-4-(tetrahydrofuran-3-yl-methoxy)benzamide

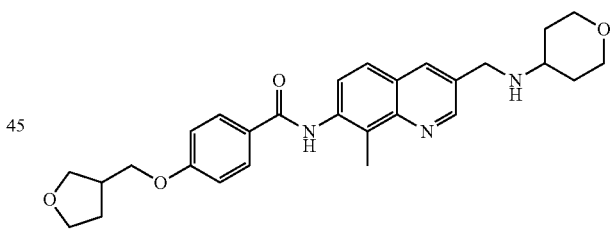

N-(3-Formyl-8-methylquinolin-7-yl)-4-(tetrahydrofuran-3-ylmethoxy)benzamide (1.5 g) obtained in Reference Example 4 and tetrahydro-2H-pyran-4-amine hydrochloride (743 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture, and the mixture was partitioned and extracted with ethyl acetate. The organic layer was washed with saturated brine and dried over anhydrous sodium sulfate, and the solvent was evaporated under reduced pressure. The residue was purified by silica gel column chromatography [developing solvent; methanol:ethyl acetate=0:100 (volume ratio)→methanol:ethyl acetate=20:80 (volume ratio)] to give the title compound (187 mg, yield 10%) as a colorless solid.

$^1$H NMR (300 MHz, DMSO-d$_6$) δ: 1.24-1.37 (2H, m), 1.65-1.74 (1H, m), 1.80-1.84 (2H, m), 1.99-2.10 (1H, m), 2.58 (2H, s), 2.61-2.73 (1H, m), 2.63 (3H, s), 3.22-3.39 (4H, m), 3.54-3.63 (1H, m), 3.66-3.75 (1H, m), 3.77-3.85 (3H, m), 3.94 (1H, s), 3.98-4.08 (2H, m), 7.08 (2H, d, J=8.7 Hz), 7.57 (1H, d, J=8.7 Hz), 7.77 (1H, d, J=8.7 Hz), 8.02 (2H, d, J=8.7 Hz), 8.20 (1H, s), 8.90 (1H, s), 10.05 (1H, s).

elemental analysis value (C$_{28}$H$_{33}$N$_3$O$_4$·1.6H$_2$O)

Calculated: C, 66.67; H, 7.23; N, 8.33.

Found: C, 66.50; H, 7.06; N, 8.03.

Example 9

N-(3-{[(trans-4-hydroxycyclohexyl)amino]methyl}-8-methylquinolin-7-yl)-4-(tetrahydrofuran-3-yl-methoxy)benzamide

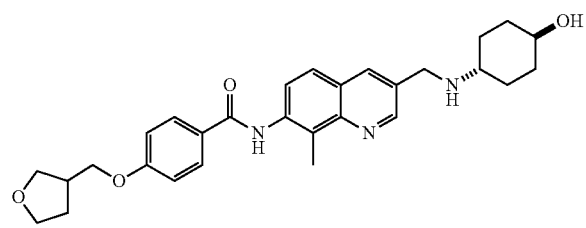 [SMILES: Cc1c(NC(=O)c2ccc(OCC3CCOC3)cc2)ccc2cc(CN[C@H]3CC[C@H](O)CC3)cnc12]

N-(3-Formyl-8-methylquinolin-7-yl)-4-(tetrahydrofuran-3-ylmethoxy)benzamide (1.5 g) obtained in Reference Example 4 and trans-4-aminocyclohexanol (622 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (820 mg, yield 43%) as a colorless solid.

$^1$H NMR (300 MHz, DMSO-d$_6$) δ: 1.02-1.14 (4H, m), 1.63-1.74 (2H, m), 1.78-1.91 (4H, m), 1.99-2.10 (1H, m), 2.36-2.38 (1H, m), 2.63 (3H, s), 2.64-2.71 (1H, m), 3.32-3.34 (1H, m), 3.53-3.58 (1H, m), 3.63-3.70 (1H, m), 3.75-3.84 (2H, m), 3.91 (2H, s), 3.95-4.08 (2H, m), 4.44 (1H, d, J=3.9 Hz), 7.09 (2H, d, J=8.7 Hz), 7.57 (1H, d, J=8.7 Hz), 7.77 (1H, d, J=8.7 Hz), 8.02 (2H, d, J=8.7 Hz), 8.18 (1H, s), 8.88 (1H, s), 10.03 (1H, s).

elemental analysis value (C$_{29}$H$_{35}$N$_3$O$_4$·0.4H$_2$O)

Calculated: C, 70.11; H, 7.26; N, 8.46.

Found: C, 70.41; H, 7.25; N, 8.49.

Example 10

N-(8-methyl-3-{[(tetrahydrofuran-2-ylmethyl)amino]methyl}quinolin-7-yl)-4-(tetrahydrofuran-2-ylmethoxy)benzamide

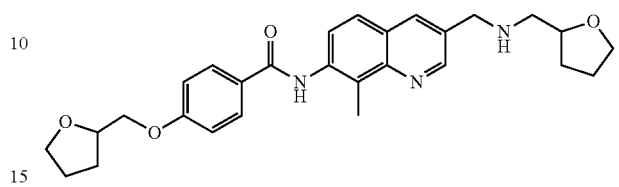

N-(3-Formyl-8-methylquinolin-7-yl)-4-(tetrahydrofuran-2-ylmethoxy)benzamide (2.5 g) obtained in Reference Example 2 and tetrahydrofurfurylamine (1.01 g) were suspended in 1-methyl-2-pyrrolidone (20 mL) and acetic acid (7.0 mL) and the mixture was stirred at room temperature for 3 hr. Sodium triacetoxyborohydride (3.5 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (1.93 g, yield 63%) as a colorless solid.

$^1$H NMR (300 MHz, DMSO-d$_6$) δ: 1.50-1.58 (1H, m), 1.66-2.08 (6H, m), 2.57-2.59 (2H, m), 2.63 (3H, s), 3.27-3.32 (2H, m), 3.56-3.66 (1H, m), 3.68-3.84 (3H, m), 3.86-3.93 (4H, m), 3.98-4.10 (2H, m), 4.15-4.23 (1H, m), 7.08 (2H, d, J=8.7 Hz), 7.57 (1H, d, J=8.7 Hz), 7.77 (1H, d, J=8.7 Hz), 8.02 (2H, d, J=8.7 Hz), 8.19 (1H, s), 8.89 (1H, s), 10.05 (1H, s).

elemental analysis value (C$_{28}$H$_{33}$N$_3$O$_4$·2.5H$_2$O)

Calculated: C, 64.60; H, 7.36; N, 8.07.

Found: C, 64.47; H, 7.20; N, 8.08.

Example 11

N-(3-{[(2,2-dimethylpropyl)amino]methyl}-8-methylquinolin-7-yl)-4-(tetrahydrofuran-2-ylmethoxy)benzamide

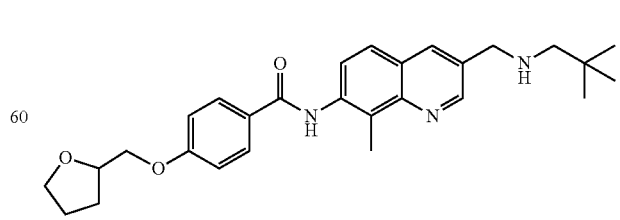

N-(3-Formyl-8-methylquinolin-7-yl)-4-(tetrahydrofuran-2-ylmethoxy)benzamide (2.5 g) obtained in Reference Example 2 and neopentylamine (872 mg) were suspended in 1-methyl-2-pyrrolidone (20 mL) and acetic acid (7.0 mL) and the mixture was stirred at room temperature for 3 hr. Sodium triacetoxyborohydride (3.5 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (1.79 g, yield 61%) as a colorless solid.

$^1$H NMR (300 MHz, DMSO-$d_6$) δ: 0.88 (9H, s), 1.66-1.75 (1H, m), 1.84-1.94 (2H, m), 1.98-2.06 (1H, m), 2.15 (1H, br), 2.27 (2H, s), 2.64 (3H, s), 3.69 (1H, q, J=8.1 Hz), 3.79 (1H, q, J=8.1 Hz), 3.92 (2H, s), 3.98-4.10 (2H, m), 4.17-4.21 (1H, m), 7.08 (2H, d, J=9.0 Hz), 7.57 (1H, d, J=9.0 Hz), 7.77 (1H, d, J=9.0 Hz), 8.01 (2H, d, J=9.0 Hz), 8.18 (1% H, s), 8.90 (1H, s), 10.04 (1H, s).

elemental analysis value ($C_{28}H_{35}N_3O_3 \cdot 0.4H_2O$)

Calculated: C, 71.74; H, 7.70; N, 8.96.

Found: C, 71.98; H, 7.47; N, 8.75.

Example 12

N-{3-[(cyclopropylamino)methyl]-8-methylquinolin-7-yl}-4-(tetrahydrofuran-2-ylmethoxy)benzamide

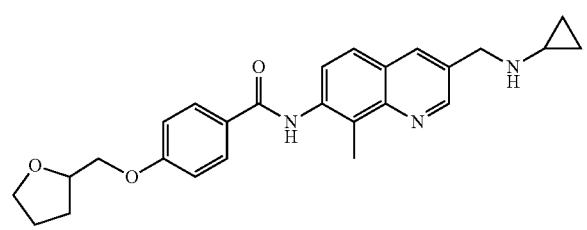 [SMILES: Cc1c(NC(=O)c2ccc(OCC3CCCO3)cc2)ccc2cc(CNC3CC3)cnc12]

N-(3-Formyl-8-methylquinolin-7-yl)-4-(tetrahydrofuran-2-ylmethoxy)benzamide (2.5 g) obtained in Reference Example 2 and cyclopropylamine (571 mg) were suspended in 1-methyl-2-pyrrolidone (20 mL) and acetic acid (7.0 mL) and the mixture was stirred at room temperature for 3 hr. Sodium triacetoxyborohydride (3.5 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (1.86 g, yield 67%) as a colorless solid.

$^1$H NMR (300 MHz, DMSO-$d_6$) δ: 0.25-0.29 (2H, m), 0.32-0.40 (2H, m), 1.66-1.75 (1H, m), 1.82-1.97 (2H, m), 2.00-2.11 (2H, m), 2.64 (3H, s), 2.88 (1H, br), 3.70 (1H, q, J=7.2 Hz), 3.80 (1H, q, J=7.2 Hz), 3.84 (2H, s), 3.93-4.10 (2H, m), 4.17-4.21 (1H, m), 7.08 (2H, d, J=9.0 Hz), 7.57 (1H, d, J=8.4 Hz), 7.77 (1H, d, J=8.4 Hz), 8.01 (2H, d, J=9.0 Hz), 8.18 (1H, s), 8.88 (1H, s), 10.03 (1H, s).

elemental analysis value ($C_{26}H_{29}N_3O_3 \cdot 1.5H_2O$)

Calculated: C, 68.10; H, 7.03; N, 9.16.

Found: C, 68.16; H, 6.91; N, 9.12.

Example 13

N-(8-methyl-3-{[(1-methylethyl)amino]methyl}quinolin-7-yl)-4-(tetrahydrofuran-2-ylmethoxy)benzamide

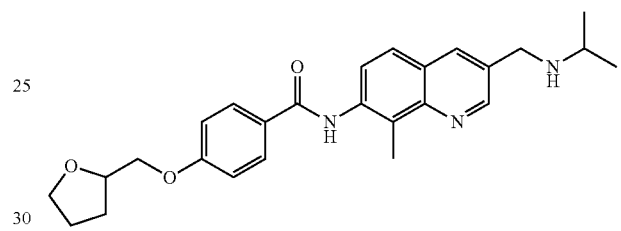

N-(3-Formyl-8-methylquinolin-7-yl)-4-(tetrahydrofuran-2-ylmethoxy)benzamide (2.5 g) obtained in Reference Example 2 and isopropylamine (591 mg) were suspended in 1-methyl-2-pyrrolidone (20 mL) and acetic acid (7.0 mL) and the mixture was stirred at room temperature for 3 hr. Sodium triacetoxyborohydride (3.5 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (1.20 g, yield 43%) as a colorless solid.

$^1$H NMR (300 MHz, DMSO-$d_6$) δ: 1.04 (6H, d, J=6.3 Hz), 1.63-1.77 (1H, m), 1.80-1.94 (2H, m), 1.97-2.08 (1H, m), 2.21 (1H, br), 2.64 (3H, s), 2.69-2.80 (1H, m), 3.69 (1H, q, J=7.2 Hz), 3.81 (1H, q, J=7.2 Hz), 3.90 (2H, s), 3.98-4.10 (2H, m), 4.15-4.23 (1H, m), 7.09 (2H, d, J=9.0 Hz), 7.57 (1H, d, J=8.7 Hz), 7.77 (1H, d, J=8.7 Hz), 8.01 (2H, d, J=9.0 Hz), 8.20 (1H, s), 8.89 (1H, s), 10.04 (1H, s).

elemental analysis value ($C_{26}H_{31}N_3O_3 \cdot 1.5H_2O$)

Calculated: C, 67.80; H, 7.44; N, 9.12.

Found: C, 68.00; H, 7.37; N, 9.18.

Example 14

N-{8-methyl-3-[(tetrahydro-2H-pyran-4-ylamino)methyl]quinolin-7-yl}-4-(tetrahydrofuran-2-yl-methoxy)benzamide

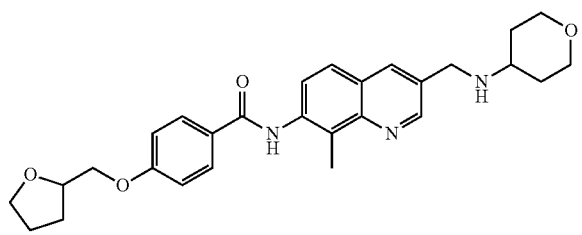

N-(3-Formyl-8-methylquinolin-7-yl)-4-(tetrahydrofuran-2-ylmethoxy)benzamide (2.5 g) obtained in Reference Example 2 and tetrahydro-2H-pyran-4-amine hydrochloride (1.37 g) were suspended in 1-methyl-2-pyrrolidone (20 mL) and acetic acid (7.0 mL) and the mixture was stirred at room temperature for 3 hr. Sodium triacetoxyborohydride (3.5 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (300 mg, yield 10%) as a colorless solid.

$^1$H NMR (300 MHz, DMSO-$d_6$) δ: 1.26-1.37 (2H, m), 1.66-1.75 (1H, m), 1.80-1.94 (4H, m), 1.97-2.06 (1H, m), 2.42 (1H, br), 2.59-2.69 (1H, m), 2.64 (3H, s), 3.23-3.39 (2H, m), 3.69 (1H, q, J=8.1 Hz), 3.76-3.85 (3H, m), 3.94 (2H, s), 3.98-4.10 (2H, m), 4.17-4.21 (1H, m), 7.08 (2H, d, J=8.7 Hz), 7.57 (1H, d, J=8.7 Hz), 7.77 (1H, d, J=8.7 Hz), 8.01 (2H, d, J=8.7 Hz), 8.21 (1H, s), 8.90 (1H, s), 10.04 (1H, s).

elemental analysis value ($C_{28}H_{33}N_3O_4 \cdot 1.0H_2O$)
Calculated: C, 68.13; H, 7.15; N, 8.51.
Found: C, 68.00; H, 6.97; N, 8.39.

Example 15

N-(3-{[(cyclopropylmethyl)amino]methyl}-8-methylquinolin-7-yl)-4-(tetrahydrofuran-2-ylmethoxy)benzamide

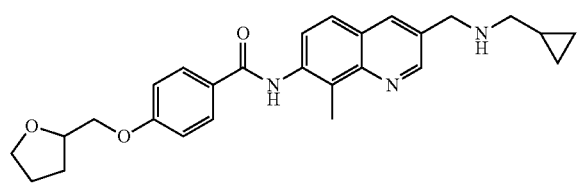 [SMILES: Cc1c(NC(=O)c2ccc(OCC3CCCO3)cc2)ccc2cc(CNCC3CC3)cnc12]

N-(3-Formyl-8-methylquinolin-7-yl)-4-(tetrahydrofuran-2-ylmethoxy)benzamide (2.5 g) obtained in Reference Example 2 and cyclopropylmethylamine (711 mg) were suspended in 1-methyl-2-pyrrolidone (20 mL) and acetic acid (7.0 mL) and the mixture was stirred at room temperature for 3 hr. Sodium triacetoxyborohydride (3.5 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (1.6 g, yield 56%) as a colorless solid.

$^1$H NMR (300 MHz, DMSO-$d_6$) δ: 0.08-0.13 (2H, m), 0.38-0.44 (2H, m), 0.91-0.95 (1H, m), 1.66-1.75 (1H, m), 1.81-1.91 (2H, m), 1.94-2.06 (1H, m), 2.31 (1H, br), 2.42 (2H, d, J=6.6 Hz), 2.64 (3H, s), 3.69 (1H, q, J=8.1 Hz), 3.80 (1H, q, J=8.1 Hz), 3.92 (2H, s), 3.98-4.10 (2H, m), 4.16-4.22 (1H, m), 7.08 (2H, d, J=9.0 Hz), 7.57 (1H, d, J=9.0 Hz), 7.77 (1H, d, J=9.0 Hz), 8.01 (2H, d, J=9.0 Hz), 8.20 (1H, s), 8.89 (1H, s), 10.04 (1H, s).

elemental analysis value ($C_{27}H_{31}N_3O_3 \cdot 0.2H_2O$)
Calculated: C, 72.20; H, 7.05; N, 9.36.
Found: C, 72.28; H, 7.06; N, 9.29.

Example 16

N-{3-[(cyclopentylamino)methyl]-8-methylquinolin-7-yl}-4-(tetrahydrofuran-3-ylmethoxy)benzamide

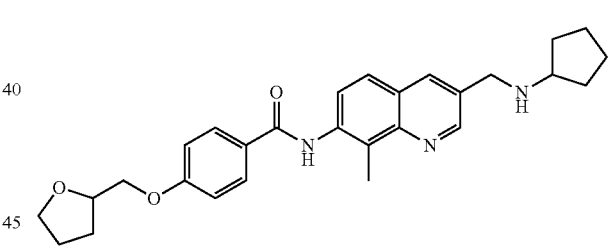

N-(3-Formyl-8-methylquinolin-7-yl)-4-(tetrahydrofuran-3-ylmethoxy)benzamide (1.5 g) obtained in Reference Example 4 and cyclopentylamine (511 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (582 mg, yield 33%) as a colorless solid.

¹H NMR (300 MHz, DMSO-d₆) δ: 1.38-1.49 (4H, m), 1.63-1.76 (5H, m), 2.01-2.08 (1H, m), 2.63 (3H, s), 2.65-2.71 (1H, m), 3.03-3.07 (1H, m), 3.29-3.35 (1H, m), 3.54-3.58 (1H, m), 3.66-3.71 (1H, m), 3.75-3.84 (2H, m), 3.90 (2H, s), 3.95-4.04 (2H, m), 7.09 (2H, d, J=8.7 Hz), 7.57 (1H, d, J=8.7 Hz), 7.77 (1H, d, J=8.7 Hz), 8.02 (2H, d, J=8.7 Hz), 8.21 (1H, s), 8.89 (1H, s), 10.04 (1H, s).

melting point: 148-149° C.

elemental analysis value ($C_{28}H_{33}N_3O_3 \cdot 0.5H_2O$)

Calculated: C, 71.77; H, 7.31; N, 8.97.

Found: C, 71.47; H, 7.23; N, 8.83.

Example 17

N-[8-methyl-3-({[(2R)-tetrahydrofuran-2-ylmethyl]amino}methyl)quinolin-7-yl]-4-[(2R)-tetrahydrofuran-2-ylmethoxy]benzamide

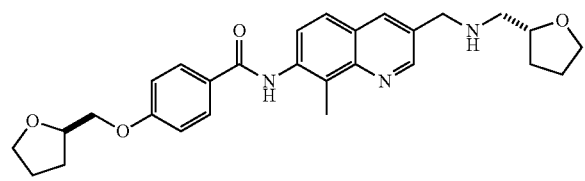 [SMILES: Cc1c(NC(=O)c2ccc(OC[C@H]3CCCO3)cc2)ccc2cc(CNC[C@H]3CCCO3)cnc12]

N-(3-Formyl-8-methylquinolin-7-yl)-4-[(2R)-tetrahydrofuran-2-ylmethoxy]benzamide (3.0 g) obtained in Reference Example 6 and (R)-tetrahydrofurfurylamine (1.1 g) were suspended in 1-methyl-2-pyrrolidone (20 mL) and acetic acid (7.0 mL) and the mixture was stirred at room temperature for 3 hr. Sodium triacetoxyborohydride (4.0 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (1.68 g, yield 46%) as a colorless solid.

¹H NMR (300 MHz, DMSO-d₆) δ: 1.47-1.63 (1H, m), 1.66-1.91 (6H, m), 1.93-2.08 (1H, m), 2.29 (1H, br), 2.56-2.59 (2H, m), 2.64 (3H, s), 3.56-3.81 (5H, m), 3.83-4.00 (2H, m), 4.01-4.10 (2H, m), 4.15-4.23 (1H, m), 7.08 (2H, d, J=8.7 Hz), 7.57 (1H, d, J=8.7 Hz), 7.77 (1H, d, J=8.7 Hz), 8.01 (2H, d, J=8.7 Hz), 8.19 (1H, s), 8.88 (1H, s), 10.03 (1H, s).

elemental analysis value ($C_{28}H_{33}N_3O_4 \cdot 2.0H_2O$)

Calculated: C, 65.73; H, 7.29; N, 8.21.

Found: C, 66.02; H, 7.19; N, 8.32.

Example 18

N-(3-{[(2-methoxy-2-methylpropyl)amino]methyl}-8-methylquinolin-7-yl)-4-[(2R)-tetrahydrofuran-2-ylmethoxy]benzamide dihydrochloride

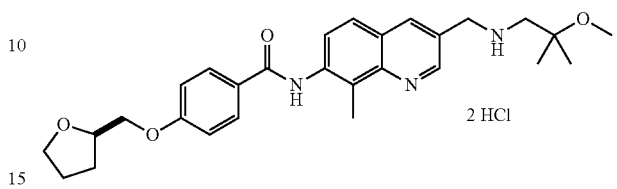

N-(3-Formyl-8-methylquinolin-7-yl)-4-[(2R)-tetrahydrofuran-2-ylmethoxy]benzamide (3.0 g) obtained in Reference Example 6 and 2-methoxy-2-methylpropan-1-amine 0.5 oxalate (1.0 g) were suspended in 1-methyl-2-pyrrolidone (20 mL) and acetic acid (7.0 mL) and the mixture was stirred at room temperature for 3 hr. Sodium triacetoxyborohydride (3.5 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 ml), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained amorphous product was dissolved in ethyl acetate, and 4N hydrogen chloride-ethyl acetate solution (0.40 mL) was added. The obtained solid was recrystallized from ethyl acetate-methanol to give the title compound (388 mg, yield 14%) as a colorless solid.

¹H NMR (300 MHz, DMSO-d₆) δ: 1.20 (6H, s), 1.66-1.75 (1H, m), 1.84-1.94 (2H, m), 1.98-2.06 (2H, m), 2.69 (3H, s), 2.96-3.00 (1H, m), 3.11 (3H, s), 3.70 (1H, q, J=7.5 Hz), 3.80 (1H, q, J=7.5 Hz), 3.99-4.11 (2H, m), 4.15-4.21 (1H, m), 4.44 (2H, s), 4.69 (1H, br), 7.09 (2H, d, J=8.7 Hz), 7.78 (1H, d, J=9.0 Hz), 7.93 (1H, d, J=9.0 Hz), 8.05 (2H, d, J=8.7 Hz), 8.78 (1H, s), 9.23 (1H, s), 9.30 (2H, br), 10.29 (1H, s).

elemental analysis value ($C_{28}H_{37}N_3O_4Cl_2 \cdot 1.5H_2O$)

Calculated: C, 58.23; H, 6.98; N, 7.28.

Found: C, 57.97; H, 6.88; N, 7.68.

Example 19

N-[8-methyl-3-({[(2S)-tetrahydrofuran-2-ylmethyl]amino}methyl)quinolin-7-yl]-4-[(2R)-tetrahydrofuran-2-ylmethoxy]benzamide

N-(3-Formyl-8-methylquinolin-7-yl)-4-[(2R)-tetrahydrofuran-2-ylmethoxy]benzamide (3.0 g) obtained in Reference Example 6 and (S)-tetrahydrofurfurylamine (1.1 g) were suspended in 1-methyl-2-pyrrolidone (20 mL) and acetic acid (7.0 mL) and the mixture was stirred at room temperature for 3 hr. Sodium triacetoxyborohydride (4.0 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (2.2 g, yield 60%) as a colorless solid.

$^1$H NMR (300 MHz, DMSO-$d_6$) δ: 1.47-1.58 (1H, m), 1.63-1.91 (6H, m), 1.93-2.08 (1H, m), 2.31 (1H, br), 2.56-2.58 (2H, m), 2.64 (3H, s), 3.41-3.81 (5H, m), 3.90 (2H, s), 3.93-4.09 (2H, m), 4.15-4.23 (1H, m), 7.08 (2H, d, J=8.7 Hz), 7.57 (1H, d, J=8.7 Hz), 7.77 (1H, d, J=8.7 Hz), 8.01 (2H, d, J=8.7 Hz), 8.19 (1H, s), 8.88 (1H, s), 10.04 (1H, s).

elemental analysis value ($C_{28}H_{33}N_3O_4 \cdot 1.75H_2O$)
Calculated: C, 66.32; H, 7.25; N, 8.29.
Found: C, 66.22; H, 7.28; N, Example 20

N-{8-methyl-3-[(tetrahydro-2H-pyran-4-ylamino)methyl]quinolin-7-yl}-4-[(2R)-tetrahydrofuran-2-ylmethoxy]benzamide

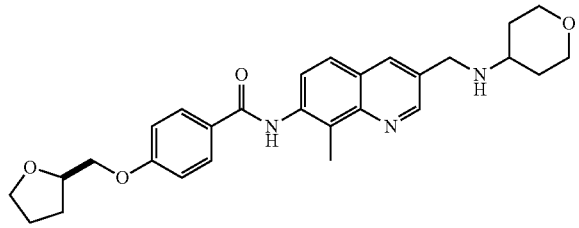 [SMILES: Cc1c(NC(=O)c2ccc(OC[C@H]3CCCO3)cc2)ccc2cc(CNC3CCOCC3)cnc12]

N-(3-Formyl-8-methylquinolin-7-yl)-4-[(2R)-tetrahydrofuran-2-ylmethoxy]benzamide (3.5 g) obtained in Reference Example 6 and tetrahydro-2H-pyran-4-amine hydrochloride (3.57 g) were suspended in 1-methyl-2-pyrrolidone (20 mL) and acetic acid (7.0 mL) and the mixture was stirred at room temperature for 3 hr. Sodium triacetoxyborohydride (4.0 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (583 mg, yield 14%) as a colorless solid.

$^1$H NMR (300 MHz, DMSO-$d_6$) δ: 1.28-1.33 (2H, m), 1.69-1.73 (1H, m), 1.78-1.86 (4H, m), 1.98-2.03 (1H, m), 2.53-2.58 (2H, m), 2.64 (3H, s), 3.23-3.30 (2H, m), 3.66-3.83 (4H, m), 3.94 (2H, s), 4.01-4.06 (2H, m), 4.16-4.20 (1H, m), 7.08 (2H, d, J=8.4 Hz), 7.57 (1H, d, J=8.4 Hz), 7.77 (1H, d, J=8.4 Hz), 8.01 (2H, d, J=8.4 Hz), 8.20 (1H, s), 8.90 (1H, s), 10.04 (1H, s).

elemental analysis value ($C_{28}H_{33}N_3O_4 \cdot 0.75H_2O$)
Calculated: C, 68.76; H, 7.11; N, 8.59.
Found: C, 68.77; H, 7.09; N, 8.68.

Example 21

N-(3-{[(2-hydroxy-2-methylpropyl)amino]methyl}-8-methylquinolin-7-yl)-4-[(2R)-tetrahydrofuran-2-ylmethoxy]benzamide

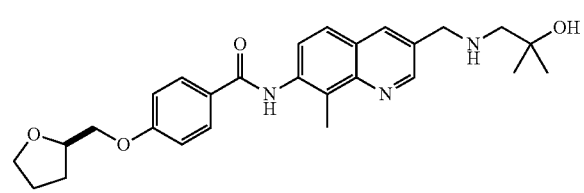 [SMILES: Cc1c(NC(=O)c2ccc(OC[C@H]3CCCO3)cc2)ccc2cc(CNCC(C)(C)O)cnc12]

N-(3-Formyl-8-methylquinolin-7-yl)-4-[(2R)-tetrahydrofuran-2-ylmethoxy]benzamide (2.0 g) obtained in Reference Example 6 and 1-amino-2-methylpropan-2-ol (1.78 g) were suspended in 1-methyl-2-pyrrolidone (20 mL) and acetic acid (7.0 mL) and the mixture was stirred at room temperature for 3 hr. Sodium triacetoxyborohydride (3.5 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (790 mg, yield 33%) as a colorless solid.

$^1$H NMR (300 MHz, DMSO-$d_6$) δ: 1.11 (6H, s), 1.66-1.75 (1H, m), 1.84-1.90 (4H, m), 1.97-2.03 (1H, m), 2.18 (1H, s), 2.64 (3H, s), 3.68-3.73 (1H, m), 3.77-3.83 (1H, m), 3.95 (2H, s), 4.02-4.06 (2H, m), 4.21 (2H, s), 7.08 (2H, d, J=8.4 Hz), 7.58 (1H, d, J=8.7 Hz), 7.77 (1H, d, J=8.7 Hz), 8.02 (2H, d, J=8.4 Hz), 8.19 (1H, s), 8.91 (1H, s), 10.04 (1H, s).

elemental analysis value ($C_{27}H_{33}N_3O_4 \cdot 0.2H_2O$)
Calculated: C, 69.42; H, 7.21; N, 8.99.
Found: C, 69.54; H, 7.17; N, 8.98.

Example 22

N-[8-methyl-3-({[(3-methyloxetan-3-yl)methyl]amino}methyl)quinolin-7-yl]-4-[(2R)-tetrahydrofuran-2-ylmethoxy]benzamide

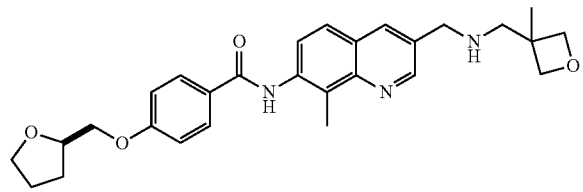 [SMILES: Cc1c(NC(=O)c2ccc(OC[C@H]3CCCO3)cc2)ccc2cc(CNCC3(C)COC3)cnc12]

N-(3-Formyl-8-methylquinolin-7-yl)-4-[(2R)-tetrahydrofuran-2-ylmethoxy]benzamide (2.15 g) obtained in Reference Example 6 and 1-(3-methyloxetan-3-yl)methanamine (500 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (780 mg, yield 33%) as a colorless solid.

$^1$H NMR (300 MHz, DMSO-$d_6$) δ: 1.26 (3H, s), 1.69-1.74 (1H, m), 1.86-1.93 (4H, m), 1.99-2.01 (1H, m), 2.65 (3H, s), 2.68 (2H, s), 3.68-3.72 (1H, m), 3.79-3.81 (1H, m), 3.94 (2H, s), 4.01-4.06 (2H, m), 4.16-4.18 (2H, m), 4.35 (2H, d, J=4.8 Hz), 7.07 (2H, d, J=8.4 Hz), 7.57 (1H, d, J=8.4 Hz), 7.77 (1H, d, J=8.4 Hz), 8.01 (2H, d, J=8.4 Hz), 8.20 (1H, s), 8.92 (1H, s), 10.04 (1H, s).

elemental analysis value ($C_{28}H_{33}N_3O_4 \cdot 1.7H_2O$)
Calculated: C, 66.44; H, 7.25; N, 8.30.
Found: C, 66.64; H, 7.05; N, 8.00.

Example 23

N-(8-methyl-3-{[(3,3,3-trifluoropropyl)amino]methyl}quinolin-7-yl)-4-[(2R)-tetrahydrofuran-2-ylmethoxy]benzamide

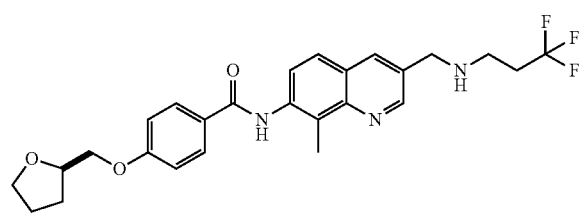 [SMILES: Cc1c(NC(=O)c2ccc(OC[C@H]3CCCO3)cc2)ccc2cc(CNCCC(F)(F)F)cnc12]

N-(3-Formyl-8-methylquinolin-7-yl)-4-[(2R)-tetrahydrofuran-2-ylmethoxy]benzamide (3.0 g) obtained in Reference Example 6 and 3,3,3-trifluoropropan-1-amine hydrochloride (1.0 g) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (462 mg, yield 14%) as a colorless solid.

$^1$H NMR (300 MHz, DMSO-$d_6$) δ: 1.67-1.72 (1H, m), 1.87-1.92 (4H, m), 1.97-2.01 (1H, m), 2.54 (1H, br), 2.64 (3H, s), 2.69-2.79 (2H, m), 3.68-3.73 (1H, m), 3.76-3.81 (1H, m), 3.93 (2H, s), 3.98-4.06 (2H, m), 4.17-4.18 (1H, m), 7.08 (2H, d, J=8.4 Hz), 7.58 (1H, d, J=8.7 Hz), 7.77 (1H, d, J=8.7 Hz), 8.01 (2H, d, J=8.4 Hz), 8.20 (1H, s), 8.89 (1H, s), 10.05 (1H, s).

elemental analysis value ($C_{26}H_{28}N_3O_3F_3 \cdot 3.5H_2O$)
Calculated: C, 56.72; H, 6.41; N, 7.63.
Found: C, 56.54; H, 6.18; N, 7.79.

Example 24

N-{3-[(cyclopentylamino)methyl]-8-methylquinolin-7-yl}-4-[(2R)-tetrahydrofuran-2-ylmethoxy]benzamide

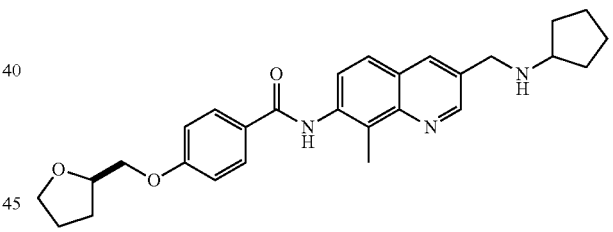

N-(3-Formyl-8-methylquinolin-7-yl)-4-[(2R)-tetrahydrofuran-2-ylmethoxy]benzamide (2.0 g) obtained in Reference Example 6 and cyclopentylamine (851 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (1.06 g, yield 45%) as a colorless solid.

$^1$H NMR (300 MHz, DMSO-d$_6$) δ: 1.34-1.49 (4H, m), 1.62-1.75 (5H, m), 1.79-1.94 (2H, m), 1.97-2.01 (1H, m), 2.41 (1H, br), 2.64 (3H, s), 2.99-3.07 (1H, m), 3.69 (1H, q, J=6.0 Hz), 3.80 (1H, q, J=6.0 Hz), 3.88 (2H, s), 3.98-4.09 (2H, m), 4.15-4.23 (1H, m), 7.08 (2H, d, J=8.7 Hz), 7.57 (1H, d, J=8.7 Hz), 7.76 (1H, d, J=8.7 Hz), 8.01 (2H, d, J=8.7 Hz), 8.19 (1H, s), 8.88 (1H, s), 10.03 (1H, s).

elemental analysis value (C$_{28}$H$_{33}$N$_3$O$_3$·1.0H$_2$O)
Calculated: C, 70.42; H, 7.39; N, 8.80.
Found: C, 70.65; H, 7.23; N, 8.90.

Example 25

N-(3-{[(2,2-dimethylpropyl)amino]methyl}-8-methylquinolin-7-yl)-4-[(2R)-tetrahydrofuran-2-ylmethoxy]benzamide

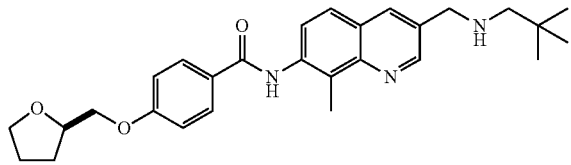 [SMILES: Cc1c(NC(=O)c2ccc(OC[C@H]3CCCO3)cc2)ccc2cc(CNCC(C)(C)C)cnc12]

N-(3-Formyl-8-methylquinolin-7-yl)-4-[(2R)-tetrahydrofuran-2-ylmethoxy]benzamide (2.0 g) obtained in Reference Example 6 and neopentylamine (1.74 g) were suspended in 1-methyl-2-pyrrolidone (20 mL) and acetic acid (7.0 mL) and the mixture was stirred at room temperature for 3 hr. Sodium triacetoxyborohydride (3.5 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (1.79 g, yield 61%) as a colorless solid.

$^1$H NMR (300 MHz, DMSO-d$_6$) δ: 0.88 (9H, s), 1.66-1.75 (1H, m), 1.82-1.91 (2H, m), 1.98-2.06 (1H, m), 2.13 (1H, br), 2.27 (2H, s), 2.64 (3H, s), 3.69 (1H, q, J=8.1 Hz), 3.80 (1H, q, J=8.1 Hz), 3.92 (2H, s), 3.98-4.10 (2H, m), 4.17-4.21 (1H, m), 7.09 (2H, d, J=8.7 Hz), 7.58 (1H, d, J=8.7 Hz), 7.76 (1H, d, J=8.7 Hz), 8.01 (2H, d, J=8.7 Hz), 8.18 (1H, s), 8.90 (1H, s), 10.04 (1H, s).

melting point: 110-111° C.
elemental analysis value (C$_{28}$H$_{35}$N$_3$O$_3$·1.5H$_2$O)
Calculated: C, 68.83; H, 7.84; N, 8.60.
Found: C, 68.55; H, 7.81; N, 8.66.

Example 26

N-(3-{[(cyclopropylmethyl)amino]methyl}-8-methylquinolin-yl)-4-[(2R)-tetrahydrofuran-2-ylmethoxy]benzamide

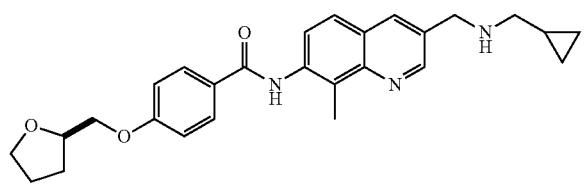 [SMILES: Cc1c(NC(=O)c2ccc(OC[C@H]3CCCO3)cc2)ccc2cc(CNCC3CC3)cnc12]

N-(3-Formyl-8-methylquinolin-7-yl)-4-[(2R)-tetrahydrofuran-2-ylmethoxy]benzamide (2.0 g) obtained in Reference Example 6 and cyclopropylmethylamine (1.44 g) were suspended in 1-methyl-2-pyrrolidone (20 mL) and acetic acid (7.0 mL) and the mixture was stirred at room temperature for 3 hr. Sodium triacetoxyborohydride (3.5 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (720 mg, yield 32%) as a colorless solid.

$^1$H NMR (300 MHz, DMSO-d$_6$) δ: 0.11-0.12 (2H, m), 0.38-0.44 (2H, m), 0.90-0.96 (1H, m), 1.66-1.75 (1H, m), 1.86-1.91 (2H, m), 1.98-2.06 (1H, m), 2.44 (2H, d, J=6.6 Hz), 2.63 (3H, s), 3.32 (1H, br), 3.69 (1H, q, J=6.9 Hz), 3.80 (1H, q, J=6.9 Hz), 3.94 (2H, s), 3.98-4.10 (2H, m), 4.17-4.21 (1H, m), 7.08 (2H, d, J=9.0 Hz), 7.57 (1H, d, J=8.7% Hz), 7.77 (1H, d, J=8.7 Hz), 8.01 (2H, d, J=9.0 Hz), 8.21 (1H, s), 8.89 (1H, s), 10.04 (1H, s).

elemental analysis value (C$_{27}$H$_{31}$N$_3$O$_3$·1.8H$_2$O)
Calculated: C, 67.85; H, 7.30; N, 8.79.
Found: C, 66.91; H, 7.38; N, 8.65.

Example 27

N-[8-methyl-3-({[(2R)-tetrahydrofuran-2-ylmethyl]amino}methyl)quinolin-7-yl]-4-[(2S)-tetrahydrofuran-2-ylmethoxy]benzamide

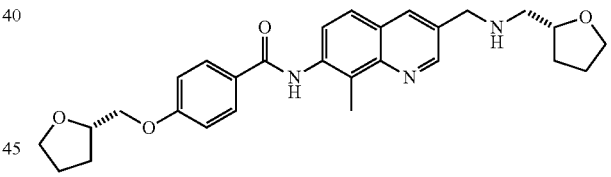

N-(3-Formyl-8-methylquinolin-7-yl)-4-[(2S)-tetrahydrofuran-2-ylmethoxy]benzamide (2.5 g) obtained in Reference Example 9 and (R)-tetrahydrofurfurylamine (1.1 g) were suspended in 1-methyl-2-pyrrolidone (20 mL) and acetic acid (7.0 ml) and the mixture was stirred at room temperature for 3 hr. Sodium triacetoxyborohydride (4.0 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (1.4 g, yield 46%) as a colorless solid.

$^1$H NMR (300 MHz, DMSO-$d_6$) δ: 1.52-1.56 (2H, m), 1.69-1.93 (6H, m), 2.59 (2H, d, J=5.7 Hz), 2.64 (3H, s), 3.32 (1H, br), 3.59-3.89 (4H, m), 3.91-3.98 (3H, m), 4.01-4.10 (2H, m), 4.17-4.21 (1H, m), 7.08 (2H, d, J=8.7 Hz), 7.57 (1H, d, J=8.7 Hz), 7.77 (1H, d, J=8.7 Hz), 8.01 (2H, d, J=8.7 Hz), 8.19 (1H, s), 8.89 (1H, s), 10.04 (1H, s).

melting point: 92-94° C.

elemental analysis value ($C_{28}H_{33}N_3O_4 \cdot 0.5H_2O$)

Calculated: C, 69.40; H, 7.07; N, 8.67.

Found: C, 69.35; H, 6.98; N, 8.62.

Example 28

N-(3-{[(2-hydroxy-2-methylpropyl)amino]methyl}-8-methylquinolin-7-yl)-4-[(2S)-tetrahydrofuran-2-ylmethoxy]benzamide

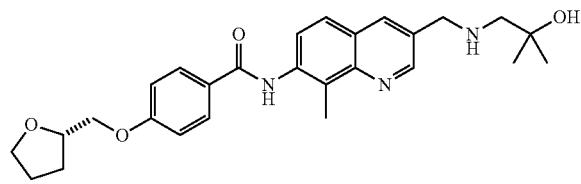 [SMILES: Cc1c(NC(=O)c2ccc(OC[C@@H]3CCCO3)cc2)ccc2cc(CNCC(C)(C)O)cnc12]

N-(3-Formyl-8-methylquinolin-7-yl)-4-[(2S)-tetrahydrofuran-2-ylmethoxy]benzamide (3.0 g) obtained in Reference Example 9 and 1-amino-2-methylpropan-2-ol (1.78 g) were suspended in 1-methyl-2-pyrrolidone (20 mL) and acetic acid (7.0 mL) and the mixture was stirred at room temperature for 3 hr. Sodium triacetoxyborohydride (4.0 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (1.0 g, yield 28%) as a colorless solid.

$^1$H NMR (300 MHz, DMSO-$d_6$) δ: 0.11 (6H, s), 1.66-1.75 (1H, m), 1.82-1.91 (2H, m), 1.90 (1H, br), 1.97-2.06 (1H, m), 2.42 (2H, s), 2.64 (3H, s), 3.69 (1H, q, J=6.3 Hz), 3.77 (1H, q, J=6.3 Hz), 3.94 (2H, s), 3.98-4.10 (2H, m), 4.20 (2H, s), 7.08 (2H, d, J=8.7 Hz), 7.57 (1H, d, J=8.7 Hz), 7.77 (1H, d, J=8.7 Hz), 8.01 (2H, d, J=8.7 Hz), 8.19 (1H, s), 8.90 (1H, s), 10.04 (1H, s).

elemental analysis value ($C_{27}H_{33}N_3O_4 \cdot 0.2H_2O$)

Calculated: C, 69.42; H, 7.21; N, 8.99.

Found: C, 69.35; H, 7.11; N, 8.90.

Example 29

N-[8-methyl-3-({[(2S)-tetrahydrofuran-2-ylmethyl]amino}methyl)quinolin-7-yl]-4-[(2S)-tetrahydrofuran-2-ylmethoxy]benzamide

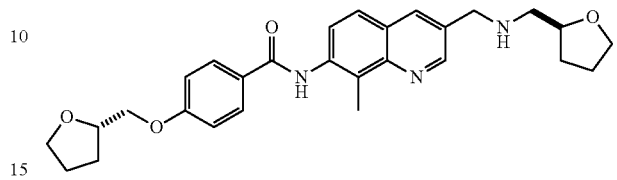

N-(3-Formyl-8-methylquinolin-7-yl)-4-[(2S)-tetrahydrofuran-2-ylmethoxy]benzamide (3.0 g) obtained in Reference Example 9 and (S)-tetrahydrofurfurylamine (1.1 g) were suspended in 1-methyl-2-pyrrolidone (20 mL) and acetic acid (7.0 mL) and the mixture was stirred at room temperature for 3 hr. Sodium triacetoxyborohydride (4.0 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (1.9 g, yield 52%) as a colorless solid.

$^1$H NMR (300 MHz, DMSO-$d_6$) δ: 1.50-1.58 (1H, m), 1.66-1.97 (6H, m), 2.00-2.05 (1H, m), 2.25 (1H, br), 2.58 (2H, d, J=6.0 Hz), 2.64 (3H, s), 3.56-3.90 (5H, m), 3.93 (2H, is), 3.98-4.10 (2H, m), 4.15-4.21 (1H, m), 7.08 (2H, d, J=8.7 Hz), 7.57 (1H, d, J=8.7 Hz), 7.76 (1H, d, J=8.7 Hz), 8.01 (2H, d, J=8.7 Hz), 8.18 (1H, s), 8.88 (1H, s), 10.03 (1H, s).

melting point: 93-94° C.

elemental analysis value ($C_{28}H_{33}N_3O_4 \cdot 1.8H_2O$)

Calculated: C, 66.20; H, 7.26; N, 8.27.

Found: C, 65.86; H, 6.84; N, 8.29.

Example 30

N-(3-{[(2-methoxy-2-methylpropyl)amino]methyl}-8-methylquinolin-7-yl)-4-[(2S)-tetrahydrofuran-2-ylmethoxy]benzamide dihydrochloride

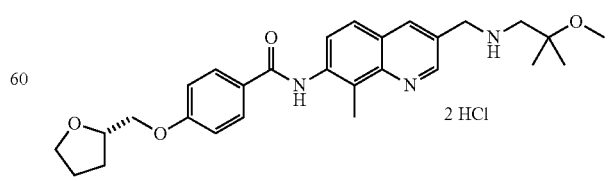

N-(3-Formyl-8-methylquinolin-7-yl)-4-[(2S)-tetrahydrofuran-2-ylmethoxy]benzamide (2.15 g) obtained in Reference Example 9 and 2-methoxy-2-methylpropan-1-amine 0.5 oxalate (1.0 g) were suspended in 1-methyl-2-pyrrolidone (20 mL) and acetic acid (7.0 mL) and the mixture was stirred at room temperature for 3 hr. Sodium triacetoxyborohydride (4.0 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained amorphous product was dissolved in ethyl acetate, and 4N hydrogen chloride-ethyl acetate solution (0.40 mL) was added. The obtained solid was recrystallized from ethyl acetate-methanol to give the title compound (497 mg, yield 17%) as a colorless solid.

$^1$H NMR (300 MHz, DMSO-$d_6$) δ: 1.21 (6H, s), 1.66-1.75 (1H, m), 1.73-1.94 (2H, m), 1.98-2.06 (1H, m), 2.71 (3H, s), 3.01 (2H, s), 3.12 (3H, s), 3.69 (1H, q, J=7.8 Hz), 3.78 (1H, q, J=7.8 Hz), 3.99-4.11 (2H, m), 4.17-4.21 (1H, m), 4.48 (2H, s), 7.09 (2H, d, J=9.0 Hz), 7.86 (1H, d, J=8.7 Hz), 7.99 (1H, d, J=8.7 Hz), 8.07 (2H, d, J=9.0 Hz), 8.98 (1H, s), 9.34 (1H, s), 9.43 (3H, br), 10.42 (1H, s).

melting point: 235-237° C.

elemental analysis value ($C_{28}H_{37}N_3O_4Cl_2 \cdot 0.5H_2O$)
Calculated: C, 60.11; H, 6.85; N, 7.51.
Found: C, 59.94; H, 6.72; N, 7.52.

Example 31

N-{8-methyl-3-[(tetrahydro-2H-pyran-4-ylamino) methyl]quinolin-7-yl}-4-[(2S)-tetrahydrofuran-2-ylmethoxy]benzamide

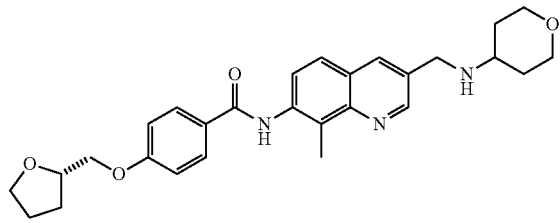

N-(3-Formyl-8-methylquinolin-7-yl)-4-[(2S)-tetrahydrofuran-2-ylmethoxy]benzamide (3.0 g) obtained in Reference Example 9 and tetrahydro-2H-pyran-4-amine hydrochloride (3.0 g) were suspended in 1-methyl-2-pyrrolidone (20 mL) and acetic acid (7.0 mL) and the mixture was stirred at room temperature for 3 hr. Sodium triacetoxyborohydride (4.0 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (576 mg, yield 16%) as a colorless solid.

$^1$H NMR (300 MHz, DMSO-$d_6$) δ: 1.25-1.38 (2H, m), 1.66-1.75 (1H, m), 1.80-1.94 (4H, m), 1.97-2.05 (1H, m), 2.35 (1H, br), 2.63 (3H, s), 3.23-3.27 (2H, m), 3.66-3.73 (1H, m), 3.76-3.85 (4H, m), 3.94 (2H, s), 3.98-4.10 (2H, m), 4.17-4.21 (1H, m), 7.08 (2H, d, J=9.0 Hz), 7.57 (1H, d, J=9.0 Hz), 7.77 (1H, d, J=9.0 Hz), 8.01 (2H, d, J=9.0 Hz), 8.21 (1H, s), 8.89 (1H, s), 10.03 (1H, s).

melting point: 158-159° C.

elemental analysis value ($C_{28}H_{33}N_3O_4$)
Calculated: C, 70.71; H, 6.99; N, 8.84.
Found: C, 70.44; H, 6.84; N, 8.86.

Example 32

N-(8-methyl-3-{[(tetrahydro-2H-pyran-4-ylmethyl) amino]methyl}quinolin-7-yl)-4-[(2S)-tetrahydrofuran-2-ylmethoxy]benzamide

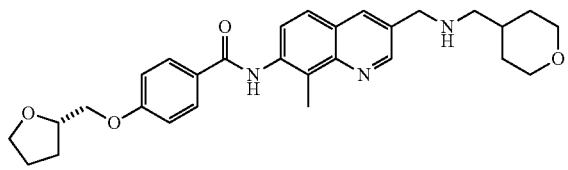

N-(3-Formyl-8-methylquinolin-7-yl)-4-[(2S)-tetrahydrofuran-2-ylmethoxy]benzamide (3.0 g) obtained in Reference Example 9 and 1-(tetrahydro-2H-pyran-4-yl)methanamine (1.32 g) were suspended in 1-methyl-2-pyrrolidone (20 mL) and acetic acid (7.0 mL) and the mixture was stirred at room temperature for 3 hr. Sodium triacetoxyborohydride (4.0 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was is evaporated under reduced pressure. The obtained solid was recrystallized from ethyl acetate-diisopropyl ether to give the title compound (1.62 g, yield 43%) as a colorless solid.

$^1$H NMR (300 MHz, DMSO-$d_6$) δ: 1.10-1.21 (2H, m), 1.63-1.75 (4H, m), 1.82-1.94 (2H, m), 1.97-2.06 (1H, m), 2.45 (2H, d, J=6.3 Hz), 2.64 (3H, s), 3.23-3.32 (2H, m), 3.66-3.73 (1H, m), 3.76-3.85 (3H, m), 3.93 (2H, s), 3.98-4.10 (2H, m), 4.15-4.21 (1H, m), 7.08 (2H, d, J=8.7 Hz), 7.57 (1H, d, J=8.7 Hz), 7.77 (1H, d, J=8.7 Hz), 8.01 (2H, d, J=8.7 Hz), 8.20 (1H, s), 8.89 (1H, s), 10.04 (1H, s).

melting point: 92-94° C.

elemental analysis value ($C_{29}H_{35}N_3O_4 \cdot 1.5H_2O$)
Calculated: C, 67.42; H, 7.41; N, 8.13.
Found: C, 67.53; H, 7.27; N, 8.17.

Example 33

N-(8-methyl-3-{[(tetrahydro-2H-pyran-4-ylmethyl)amino]methyl}quinolin-7-yl)-4-[(2R)-tetrahydrofuran-2-ylmethoxy]benzamide

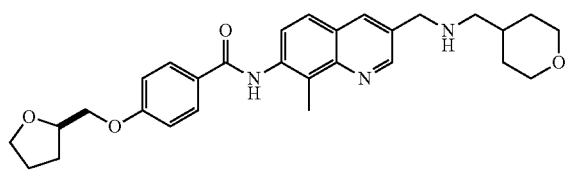

N-(3-Formyl-8-methylquinolin-7-yl)-4-[(2R)-tetrahydrofuran-2-ylmethoxy]benzamide (3.0 g) obtained in Reference Example 6 and 1-(tetrahydro-2H-pyran-4-yl)methanamine (1.32 g) were suspended in 1-methyl-2-pyrrolidone (20 mL) and acetic acid (7.0 mL) and the mixture was stirred at room temperature for 3 hr. Sodium triacetoxyborohydride (4.0 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 ml), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (980 mg, yield 26%) as a colorless solid.
$^1$H NMR (300 MHz, DMSO-$d_6$) δ: 1.09-1.17 (2H, m), 1.63-1.66 (4H, m), 1.86-1.90 (2H, m), 1.95-2.02 (1H, m), 2.38 (1H, br), 2.41 (2H, d, J=6.3 Hz), 2.64 (3H, s), 3.23-3.33 (2H, m), 3.68-3.72 (1H, m), 3.77-3.83 (3H, m), 3.90 (2H, s), 3.98-4.06 (2H, m), 4.16-4.20 (1H, m), 7.08 (2H, d, J=8.7 Hz), 7.57 (1H, d, J=8.7 Hz), 7.77 (1H, d, J=8.7 Hz), 8.01 (2H, d, J=8.7 Hz), 8.18 (1H, s), 8.89 (1H, s), 10.03 (1H, s).
elemental analysis value ($C_{29}H_{35}N_3O_4 \cdot 1.0H_2O$)
Calculated: C, 68.62; H, 7.35; N,
Found: C, 68.41; H, 7.28; N, 8.39.

Example 34

N-[8-methyl-3-({[(3-methyloxetan-3-yl)methyl]amino}methyl)quinolin-7-yl]-4-[(2S)-tetrahydrofuran-2-ylmethoxy]benzamide

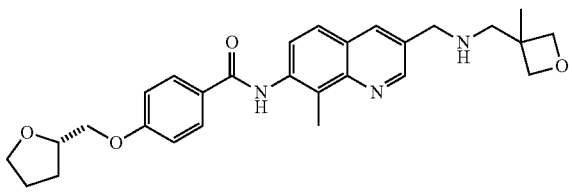

N-(3-Formyl-8-methylquinolin-7-yl)-4-[(2S)-tetrahydrofuran-2-ylmethoxy]benzamide (2.15 g) obtained in Reference Example 9 and 1-(3-methyloxetan-3-yl)methanamine (500 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (960 mg, yield 41%) as a colorless solid.
$^1$H NMR (300 MHz, DMSO-$d_6$) δ: 1.25 (3H, s), 1.66-1.75 (1H, m), 1.86-1.89 (4H, m), 1.97-2.04 (1H, m), 2.64 (3H, s), 2.67 (2H, s), 3.69 (1H, q, J=6.9 Hz), 3.80 (1H, q, J=6.9 Hz), 3.94 (2H, s), 3.98-4.10 (2H, m), 4.17 (2H, d, J=5.4 Hz), 4.35 (2H, d, J=5.4 Hz), 7.08 (2H, d, J=8.7 Hz), 7.58 (1H, d, J=8.7 Hz), 7.77 (1H, d, J=8.7 Hz), 8.01 (2H, d, J=8.7 Hz), 8.20 (1H, s), 8.91 (1H, s), 10.03 (1H, s).
melting point: 117-119° C.
elemental analysis value ($C_{28}H_{33}N_3O_4 \cdot 1.9H_2O$)
Calculated: C, 65.97; H, 7.28; N, 8.24.
Found: C, 66.05; H, 7.03; N, 8.25.

Example 35

N-{3-[(ethylamino)methyl]-8-methylquinolin-7-yl}-4-[(2S)-tetrahydrofuran-2-ylmethoxy]benzamide

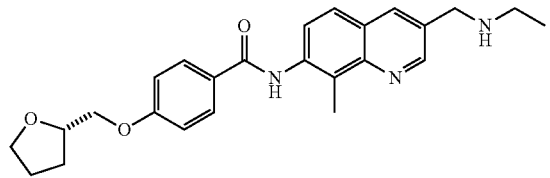

N-(3-Formyl-8-methylquinolin-7-yl)-4-[(2S)-tetrahydrofuran-2-ylmethoxy]benzamide (1.0 g) obtained in Reference Example 9 and ethylamine (4 mL, 2.0M tetrahydrofuran solution) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (392 mg, yield 37%) as a colorless solid.
$^1$H NMR (300 MHz, DMSO-$d_6$) δ: 1.06 (3H, t, J=7.2 Hz), 1.64-1.75 (1H, m), 1.77-1.92 (2H, m), 1.94-2.08 (1H, m), 2.42 (1H, br), 2.57 (2H, q, J=7.2 Hz), 2.64 (3H, s), 3.69% (1H, q, J=6.3 Hz), 3.80 (1H, q, J=6.3 Hz), 3.89 (2H, s), 3.98-4.10

(2H, m), 4.15-4.23 (1H, m), 7.08 (2H, d, J=8.7 Hz), 7.57 (1H, d, J=8.7 Hz), 7.77 (1H, d, J=8.7 Hz), 8.01 (2H, d, J=8.7 Hz), 8.18 (1H, s), 8.88 (1H, s), 10.03 (1H, s).

melting point: 149-151° C.

elemental analysis value ($C_{25}H_{29}N_3O_3 \cdot 1.9H_2O$)

Calculated: C, 66.18; H, 7.29; N, 9.26.

Found: C, 66.23; H, 7.09; N, 9.20.

Example 36

N-{3-[(cyclopentylamino)methyl]-8-methylquinolin-7-yl}-4-[(2S)-tetrahydrofuran-2-ylmethoxy]benzamide

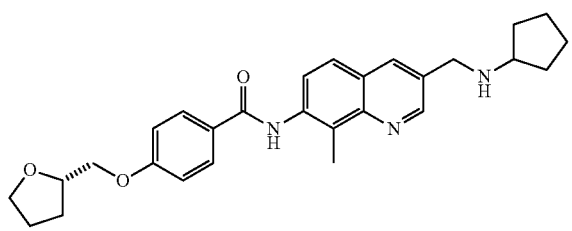

N-(3-Formyl-8-methylquinolin-7-yl)-4-[(2S)-tetrahydrofuran-2-ylmethoxy]benzamide (1.0 g) obtained in Reference Example 9 and cyclopentylamine (851 mg) were suspended in 1-methyl-2-pyrrolidone (20 mL) and acetic acid (7.0 mL) and the mixture was stirred at room temperature for 3 hr. Sodium triacetoxyborohydride (3.5 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (375 mg, yield 32%) as a colorless solid.

$^1$H NMR (300 MHz, DMSO-d$_6$) δ: 1.37-1.49 (4H, m), 1.62-1.75 (5H, m), 1.82-1.94 (2H, m), 1.98-2.05 (1H, m), 2.29 (1H, br), 2.63 (3H, s), 3.03 (1H, t, J=6.0 Hz), 3.70 (1H, q, J=6.1 Hz), 3.80 (1H, q, J=6.1 Hz), 3.88 (2H, s), 3.98-4.10 (2H, m), 4.15-4.21 (1H, m), 7.08 (2H, d, J=8.7 Hz), 7.57 (1H, d, J=8.7 Hz), 7.77 (1H, d, J=8.7 Hz), 8.01 (2H, d, J=8.7 Hz), 8.20 (1H, s), 8.88 (1H, s), 10.03 (1H, s).

melting point: 152-153° C.

elemental analysis value ($C_{28}H_{33}N_3O_3$)

Calculated: C, 73.18; H, 7.24; N, 9.14.

Found: C, 72.92; H, 7.25; N, 9.08.

Example 37

N-(3-{[(cyclopropylmethyl)amino]methyl}-8-methylquinolin-7-yl)-4-[(2S)-tetrahydrofuran-2-ylmethoxy]benzamide

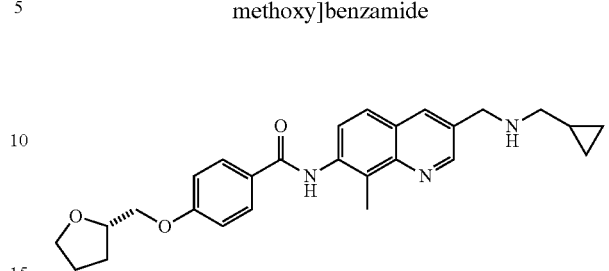

N-(3-Formyl-8-methylquinolin-7-yl)-4-[(2S)-tetrahydrofuran-2-ylmethoxy]benzamide (1.0 g) obtained in Reference Example 9 and cyclopropylmethylamine (711 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (298 mg, yield 26%) as a colorless solid.

$^1$H NMR (300 MHz, DMSO-d$_6$) δ: 0.10-0.15 (2H, m), 0.39-0.45 (2H, m), 0.92-0.95 (1H, m), 1.66-1.75 (1H, m), 1.83-1.90 (2H, m), 1.98-2.05 (1H, m), 2.46 (2H, d, J=6.6 Hz), 2.64 (3H, s), 3.49 (1H, br), 3.69 (1H, q, J=7.2 Hz), 3.80 (1H, q, J=6.9 Hz), 3.96 (2H, s), 3.98-4.10 (2H, m), 4.15-4.21 (1H, m), 7.08 (2H, d, J=8.7 Hz), 7.58 (1H, d, J=8.7 Hz), 7.77 (1H, d, J=8.7 Hz), 8.01 (2H, d, J=8.7 Hz), 8.22 (1H, s), 8.89 (1H, s), 10.05 (1H, s).

melting point: 156-158° C.

elemental analysis value ($C_{27}H_{31}N_3O_3 \cdot 1.5H_2O$)

Calculated: C, 68.62; H, 7.25; N, 8.89.

Found: C, 68.53; H, 6.89; N, 8.81.

Example 38

N-(8-methyl-3-{[(2-methylpropyl)amino]methyl}quinolin-7-yl)-4-[(2S)-tetrahydrofuran-2-ylmethoxy]benzamide

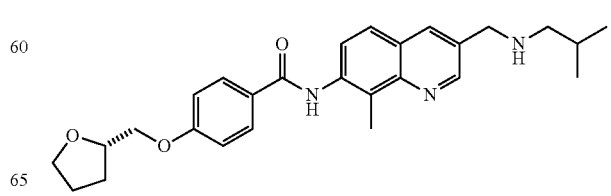

N-(3-Formyl-8-methylquinolin-7-yl)-4-[(2S)-tetrahydrofuran-2-ylmethoxy]benzamide (1.6 g) obtained in Reference Example 9 and isobutylamine (730 mg) were suspended in 1-methyl-2-pyrrolidone (20 mL) and acetic acid (7.0 mL) and the mixture was stirred at room temperature for 3 hr. Sodium triacetoxyborohydride (3.0 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (704 mg, yield 38%) as a colorless solid.

$^1$H NMR (300 MHz, DMSO-d$_6$) δ: 0.88 (6H, d, J=6.6 Hz), 1.66-1.75 (2H, m), 1.84-1.94 (2H, m), 1.98-2.06 (1H, m), 2.25 (1H, br), 2.34 (2H, d, J=6.6 Hz), 2.63 (3H, s), 3.72 (1H, q, J=6.3 Hz), 3.81 (1H, q, J=6.3 Hz), 3.89 (2H, s), 3.98-4.09 (2H, m), 4.17-4.21 (1H, m), 7.08 (2H, d, J=9.0 Hz), 7.57 (1H, d, J=8.7 Hz), 7.77 (1H, d, J=8.7 Hz), 8.01 (2H, d, J=9.0 Hz), 8.19 (1H, s), 8.89 (1H, s), 10.04 (1H, s).

melting point: 142-143° C.
elemental analysis value (C$_{27}$H$_{33}$N$_3$O$_3$.1.0H$_2$O)
Calculated: C, 69.65; H, 7.58; N, 9.03.
Found: C, 69.77; H, 7.50; N, 9.04.

Example 39

N-(3-{[(2,2-dimethylpropyl)amino]methyl}-8-methylquinolin-7-yl)-4-[(2S)-tetrahydrofuran-2-ylmethoxy]benzamide

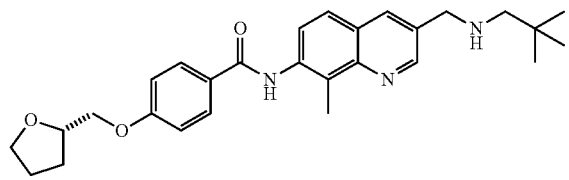

N-(3-Formyl-8-methylquinolin-7-yl)-4-[(2S)-tetrahydrofuran-2-ylmethoxy]benzamide (3.0 g) obtained in Reference Example 9 and neopentylamine (2.5 g) were suspended in 1-methyl-2-pyrrolidone (20 mL) and acetic acid (7.0 mL) and the mixture was stirred at room temperature for 3 hr. Sodium triacetoxyborohydride (6.35 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (1.18 g, yield 33%) as a colorless solid.

$^1$H NMR (300 MHz, DMSO-d$_6$) δ: 0.88 (9H, s), 1.66-1.75 (1H, m), 1.86-1.89 (4H, m), 1.97-2.05 (1H, m), 2.14 (1H, br), 2.27 (2H, s), 2.64 (3H, s), 3.71 (1H, q, J=6.3 Hz), 3.82 (1H, q, J=6.3 Hz), 3.92 (2H, s), 3.98-4.10 (2H, m), 4.17-4.21 (1H, m), 7.08 (2H, d, J=9.0 Hz), 7.57 (1H, d, J=9.0 Hz), 7.77 (1H, d, J=9.0 Hz), 8.02 (2H, d, J=9.0 Hz), 8.19 (1H, s), 8.91 (1H, s), 10.05 (1H, s).

melting point: 114-116° C.
elemental analysis value (C$_{28}$H$_{35}$N$_3$O$_3$.1.5H$_2$O)
Calculated: C, 68.83; H, 7.84; N, 8.60.
Found: C, 68.58; H, 7.68; N, 8.61.

Example 40

N-(3-{[(trans-4-hydroxycyclohexyl)amino]methyl}-8-methylquinolin-7-yl)-4-[(2R)-tetrahydrofuran-2-ylmethoxy]benzamide

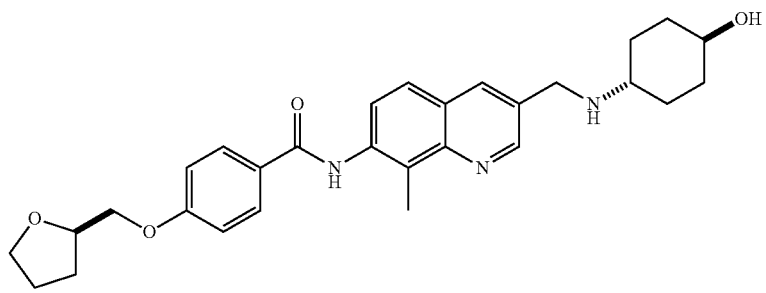

N-(3-Formyl-8-methylquinolin-7-yl)-4-[(2R)-tetrahydrofuran-2-ylmethoxy]benzamide (1.6 g) obtained in Reference Example 6 and trans-4-aminocyclohexanol (944 mg) were suspended in 1-methyl-2-pyrrolidone (20 mL) and acetic acid (7.0 mL) and the mixture was stirred at room temperature for 3 hr. Sodium triacetoxyborohydride (4.2 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (400 mg, yield 20%) as a colorless solid.

$^1$H NMR (300 MHz, DMSO-$d_6$) δ: 1.02-1.12 (4H, m), 1.66-1.73 (1H, m), 1.75-2.07 (7H, m), 2.38 (1H, br), 2.63 (3H, s), 3.33-3.39 (2H, m), 3.69 (1H, q, J=6.3 Hz), 3.79 (1H, q, J=6.3 Hz), 3.93 (2H, s), 3.98-4.10 (2H, m), 4.15-4.21 (1H, m), 4.45 (1H, d, J=4.5 Hz), 7.08 (2H, d, J=9.0 Hz), 7.57 (1H, d, J=9.0 Hz), 7.77 (1H, d, J=9.0 Hz), 8.01 (2H, d, J=9.0 Hz), 8.19 (1H, s), 8.88 (1H, s), 10.04 (1H, s).

melting point: 182-183° C.
elemental analysis value ($C_{29}H_{35}N_3O_4 \cdot 0.3H_2O$)
Calculated: C, 70.36; H, 7.25; N, 8.49.
Found: C, 70.47; H, 7.22; N, 8.52.

Example 41

N-[3-({[(1-hydroxycyclohexyl)methyl]amino}methyl)-8-methylquinolin-7-yl]-4-[(2S)-tetrahydrofuran-2-ylmethoxy]benzamide dihydrochloride

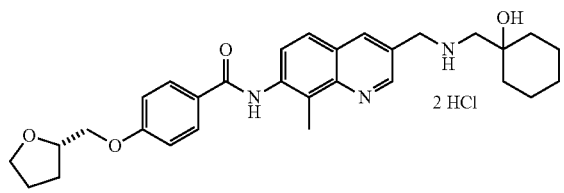

N-(3-Formyl-8-methylquinolin-7-yl)-4-[(2S)-tetrahydrofuran-2-ylmethoxy]benzamide (1.6 g) obtained in Reference Example 9 and 1-(aminomethyl)cyclohexanol hydrochloride (1.36 g) were suspended in 1-methyl-2-pyrrolidone (20 mL) and acetic acid (7.0 mL) and the mixture was stirred at room temperature for 3 hr. Sodium triacetoxyborohydride (4.2 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained amorphous product was dissolved in ethyl acetate, and 4N hydrogen chloride-ethyl acetate solution (0.40 mL) was added. The obtained solid was recrystallized from ethyl acetate-methanol to give the title compound (292 mg, yield 12%) as a colorless solid.

$^1$H NMR (300 MHz, DMSO-$d_6$) δ: 1.15-1.23 (1H, m), 1.41-1.57 (9H, m), 1.64-1.72 (1H, m), 1.73-1.94 (2H, m), 1.98-2.08 (1H, m), 2.71 (3H, s), 2.91-2.94 (2H, m), 3.69 (1H, q, J=6.3 Hz), 3.80 (1H, q, J=6.3 Hz), 3.99-4.11 (2H, m), 4.15-4.23 (1H, m), 4.47 (2H, s), 6.38 (2H, br), 7.10 (2H, d, J=9.0 Hz), 7.85 (1H, d, J=8.7 Hz), 7.99 (1H, d, J=8.7 Hz), 8.06 (2H, d, J=9.0 Hz), 8.94 (1H, s), 9.30 (1H, s), 9.41 (2H, br), 10.39 (1H, s).

melting point: 242-244° C.
elemental analysis value ($C_{30}H_{39}N_3O_4Cl_2 \cdot 0.5H_2O$)
Calculated: C, 61.53; H, 6.89; N, 7.18.
Found: C, 61.48; H, 6.82; N, 7.25.

Example 42

N-(3-{[(5-hydroxytricyclo[3.3.1.1$^{3,7}$]dec-2-yl)amino]methyl}-8-methylquinolin-7-yl)-4-(tetrahydrofuran-2-ylmethoxy)benzamide

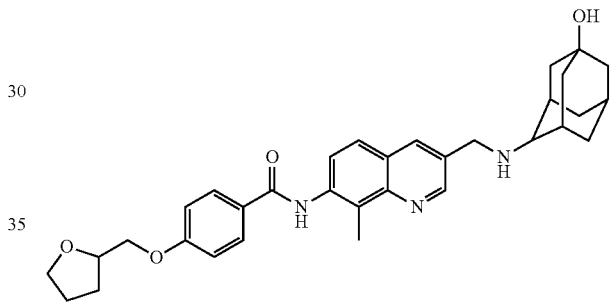

N-(3-Formyl-8-methylquinolin-7-yl)-4-(tetrahydrofuran-2-ylmethoxy)benzamide (3.2 g) obtained in Reference Example 2 and 4-aminoadamantan-1-ol hydrochloride (3.46 g) were suspended in 1-methyl-2-pyrrolidone (20 mL) and acetic acid (7.0 mL) and the mixture was stirred at room temperature for 3 hr. Sodium triacetoxyborohydride (6.0 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (1.4 g, yield 23%) as a colorless solid.

$^1$H NMR (300 MHz, DMSO-$d_6$) δ: 1.07-1.11 (1H, m), 1.17-1.30 (2H, m), 1.58 (3H, s), 1.66-1.80 (1H, m), 1.85-2.05 (6H, In), 2.15-2.20 (2H, m), 2.37 (1H, br), 2.64 (3H, s), 2.69 (2H, s), 3.27-3.39 (1H, m), 3.69 (1H, q, J=6.3 Hz), 3.80 (1H, q, J=6.3 Hz), 3.89 (2H, s), 3.98-4.10 (2H, m), 4.15-4.21 (1H, m), 4.30 (1H, s), 7.08 (2H, d, J=9.0 Hz), 7.57 (1H, d, J=9.0 Hz), 7.77 (1H, d, J=9.0 Hz), 8.02 (2H, d, J=9.0 Hz), 8.20 (1H, s), 8.91 (1H, s), 10.04 (1H, s).

Example 43

N-[8-methyl-3-({[2-(1-methylethoxy)ethyl]amino}methyl)quinolin-7-yl]-4-(tetrahydrofuran-2-ylmethoxy)benzamide

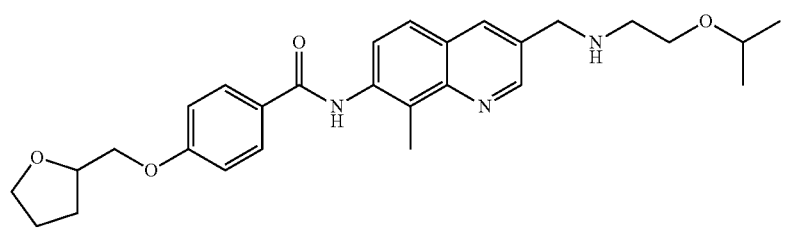 [SMILES: Cc1c(NC(=O)c2ccc(OCC3CCCO3)cc2)ccc2cc(CNCCOC(C)C)cnc12]

N-(3-Formyl-8-methylquinolin-7-yl)-4-(tetrahydrofuran-2-ylmethoxy)benzamide (3.2 g) obtained in Reference Example 2 and 2-(1-methylethoxy)ethanamine (1.73 g) were suspended in 1-methyl-2-pyrrolidone (20 mL) and acetic acid (7.0 mL) and the mixture was stirred at room temperature for 3 hr. Sodium triacetoxyborohydride (6.0 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (980 mg, yield 25%) as a colorless solid.

$^1$H NMR (300 MHz, DMSO-$d_6$) δ: 1.08 (6H, d, J=6.0 Hz), 1.66-1.75 (1H, m), 1.84-1.97 (2H, m), 2.00-2.05 (2H, m), 2.64 (3H, s), 2.66-2.70 (2H, m), 3.33 (1H, br), 3.44-3.48 (2H, m), 3.51-3.57 (1H, m), 3.69 (1H, q, J=6.3 Hz), 3.80 (1H, q, J=6.3 Hz), 3.94 (2H, s), 3.98-4.10 (2H, m), 4.17-4.21 (1H, m), 7.08 (2H, d, J=9.0 Hz), 7.58 (1H, d, J=9.0 Hz), 7.77 (1H, d, J=9.0 Hz), 8.02 (2H, d, J=9.0 Hz), 8.20 (1H, s), 8.88 (1H, s), 10.05 (1H, s).

elemental analysis value ($C_{28}H_{35}N_3O_4 \cdot 1.8H_2O$)
Calculated: C, 65.94; H, 7.63; N, 8.24.
Found: C, 65.73; H, 7.23; N, 8.24.

Example 44

N-(3-{[(3-hydroxytricyclo[3.3.1.1$^{3,7}$]dec-1-yl)amino]methyl}-8-methylquinolin-7-yl)-4-(tetrahydrofuran-2-ylmethoxy)benzamide

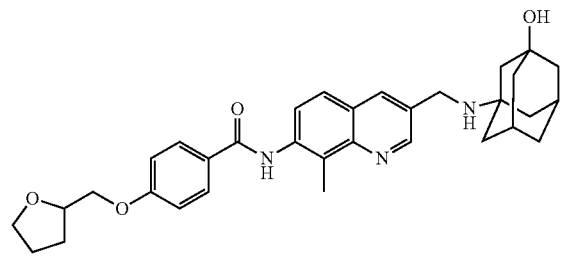 [SMILES: Cc1c(NC(=O)c2ccc(OCC3CCCO3)cc2)ccc2cc(CNC34CC5CC(CC(O)(C5)C3)C4)cnc12]

N-(3-Formyl-8-methylquinolin-7-yl)-4-(tetrahydrofuran-2-ylmethoxy)benzamide (1.5 g) obtained in Reference Example 2 and 3-aminoadamantan-1-ol hydrochloride (1.29 g) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (172 mg, yield 8%) as a colorless solid.

$^1$H NMR (300 MHz, DMSO-$d_6$) δ: 1.15 (2H, br), 1.53-1.56 (9H, m), 1.66-1.75 (1H, m), 1.72-1.91 (2H, m), 1.94-2.05 (1H, m), 2.15 (2H, br), 2.63 (3H, s), 3.33-3.39 (2H, m), 3.69 (1H, q, J=7.2 Hz), 3.79 (1H, q, J=7.2 Hz), 3.90 (2H, s), 3.98-4.09 (2H, m), 4.17-4.21 (1H, m), 4.41 (1H, s), 7.08 (2H, d, J=8.7 Hz), 7.56 (1H, d, J=8.7 Hz), 7.77 (1H, d, J=8.7 Hz), 8.01 (2H, d, J=8.7 Hz), 8.20 (1H, s), 8.88 (1H, s), 10.03 (1H, s).

elemental analysis value ($C_{33}H_{39}N_3O_4$·0.5$H_2O$)
Calculated: C, 71.97; H, 7.32; N, 7.63.
Found: C, 72.21; H, 7.20; N, 7.57.

Example 45

N-{8-methyl-3-[(propylamino)methyl]quinolin-7-yl}-4-[(2S)-tetrahydrofuran-2-ylmethoxy]benzamide

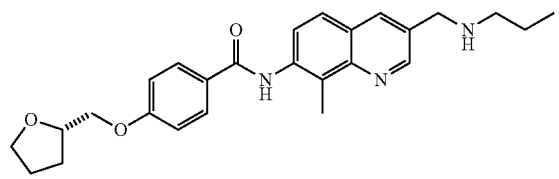

N-(3-Formyl-8-methylquinolin-7-yl)-4-[(2S)-tetrahydrofuran-2-ylmethoxy]benzamide (1.0 g) obtained in Reference Example 9 and n-propylamine (414 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (523 mg, yield 47%) as a colorless solid.

$^1$H NMR (300 MHz, DMSO-$d_6$) δ: 0.88 (3H, t, J=7.2 Hz), 1.40-1.52 (2H, m), 1.66-1.75 (1H, m), 1.82-1.98 (4H, m), 2.00-2.06 (1H, m), 2.51 (2H, t, J=7.2 Hz), 2.64 (3H, s), 3.31 (1H, br), 3.69 (1H, q, J=6.6 Hz), 3.78 (1H, q, J=6.6 Hz), 3.89 (2H, s), 3.98-4.10 (2H, m), 4.15-4.21 (1H, m), 7.08 (2H, d, J=8.7 Hz), 7.57 (1H, d, J=8.7 Hz), 7.77 (1H, d, J=8.7 Hz), 8.02 (2H, d, J=8.7 Hz), 8.19 (1H, s), 8.89 (1H, s), 10.04 (1.H, s).

melting point: 121-122° C.
elemental analysis value ($C_{26}H_{31}N_3O_3$·1.6$H_2O$)
Calculated: C, 67.54; H, 7.46; N, 9.09.
Found: C, 67.27; H, 7.20; N, 8.86.

Example 46

N-[3-({[(1R,2R)-2-hydroxycyclohexyl]amino}methyl)-8-methylquinolin-7-yl]-4-[(2S)-tetrahydrofuran-2-ylmethoxy]benzamide

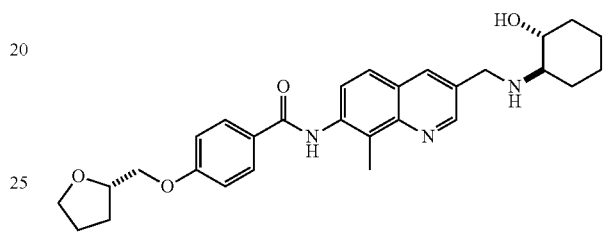

N-(3-Formyl-8-methylquinolin-7-yl)-4-[(2S)-tetrahydrofuran-2-ylmethoxy]benzamide (1.0 g) obtained in Reference Example 9 and (1R,2R)-2-aminocyclohexanol hydrochloride (1.52 g) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (78 mg, yield 6%) as a colorless solid.

$^1$H NMR (300 MHz, DMSO-$d_6$) δ: 0.98-1.17 (6H, m), 1.59-2.00 (8H, m), 2.26 (1H, br), 2.64 (3H, s), 3.16-3.19 (1H, m), 3.68-3.73 (1H, m), 3.77-3.91 (2H, m), 4.00-4.05 (2H, m), 4.17-4.19 (1H, m), 4.64-4.67 (1H, m), 7.08 (2H, d, J=8.7 Hz), 7.57 (1H, d, J=8.7 Hz), 7.78 (1H, d, J=8.7 Hz), 8.01 (2H, d, J=8.7 Hz), 8.21 (1H, s), 8.90 (1H, s), 10.05 (1H, s).

melting point: 142-143° C.
elemental analysis value ($C_{29}H_{35}N_3O_4$·0.6$H_2O$)
Calculated: C, 69.60; H, 7.29; N, 8.40.
Found: C, 69.30; H, 7.09; N, 8.16.

Example 47

N-[3-({[(1S,2S)-2-hydroxycyclohexyl]amino}methyl)-8-methylquinolin-7-yl]-4-[(2S)-tetrahydrofuran-2-ylmethoxy]benzamide

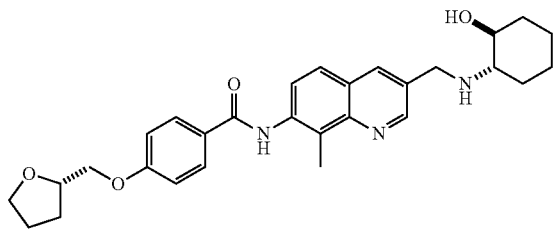

N-(3-Formyl-8-methylquinolin-7-yl)-4-[(2S)-tetrahydrofuran-2-ylmethoxy]benzamide (1.0 g) obtained in Reference Example 9 and (1S,2S)-2-aminocyclohexanol (1.15 g) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (443 mg, yield 35%) as a colorless solid.

$^1$H NMR (300 MHz, DMSO-d$_6$) δ: 0.98-1.19 (6H, m), 1.59-2.05 (8H, m), 2.23-2.30 (1H, m), 2.64 (3H, s), 3.18-3.20 (1H, m), 3.69 (1H, q, J=7.2 Hz), 3.80 (1H, q, J=7.2 Hz), 3.98-4.10 (2H, m), 4.15-4.21 (1H, m), 4.65 (1H, d, J=4.8 Hz), 7.08 (2H, d, J=9.0 Hz), 7.58 (1H, d, J=9.0 Hz), 7.77 (1H, d, J=9.0 Hz), 8.01 (2H, d, J=9.0 Hz), 8.22 (1H, s), 8.90 (1H, s), 10.04 (1H, s).

melting point: 157-158° C.

elemental analysis value (C$_{29}$H$_{35}$N$_3$O$_4$·0.4H$_2$O)

Calculated: C, 70.11; H, 7.26; N, 8.46.

Found: C, 70.35; H, 7.14; N, 8.40.

Example 48

N-(3-{[(trans-4-hydroxycyclohexyl)amino]methyl}-8-methylquinolin-7-yl)-4-[(2S)-tetrahydrofuran-2-ylmethoxy]benzamide

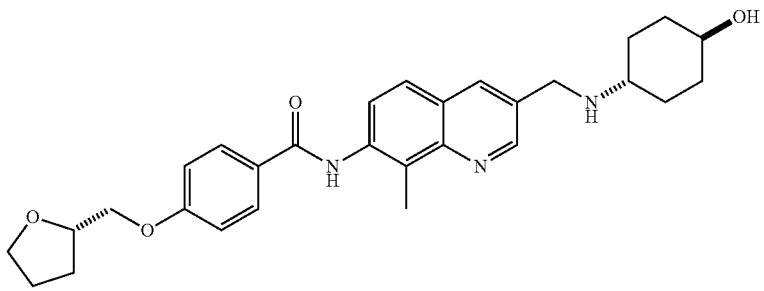

N-(3-Formyl-8-methylquinolin-7-yl)-4-[(2S)-tetrahydrofuran-2-ylmethoxy]benzamide (1.0 g) obtained in Reference Example 9 and trans-4-aminocyclohexanol (1.15 g) were suspended in 1-methyl-2-pyrrolidone (20 mL) and acetic acid (7.0 mL) and the mixture was stirred at room temperature for 3 hr. Sodium triacetoxyborohydride (2.33 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (573 mg, yield 46%) as a colorless solid.

$^1$H NMR (300 MHz, DMSO-d$_6$) δ: 1.07-1.12 (4H, m), 1.66-2.06 (8H, m), 2.20-2.37 (2H, m), 2.64 (3H, s), 3.34 (1H, br), 3.72 (1H, q, J=6.9 Hz), 3.82 (1H, q, J=6.9 Hz), 3.92 (2H, s), 3.98-4.10 (2H, m), 4.17-4.21 (1H, m), 4.44-4.48 (1H, m), 7.08 (2H, d, J=8.7 Hz), 7.57 (1H, d, J=8.7 Hz), 7.76 (1H, d, J=8.7 Hz), 8.01 (2H, d, J=8.7 Hz), 8.19 (1H, s), 8.89 (1H, s), 10.04 (1H, s).

melting point: 183-184° C.
elemental analysis value ($C_{29}H_{35}N_3O_4 \cdot 0.5H_2O$)
Calculated: C, 69.86; H, 7.28; N, 8.43.
Found: C, 70.15; H, 7.01; N, 8.47.

Example 49

N-[8-methyl-3-({[2-(1-methylethoxy)ethyl]amino}methyl)quinolin-7-yl]-4-[(2S)-tetrahydrofuran-2-ylmethoxy]benzamide

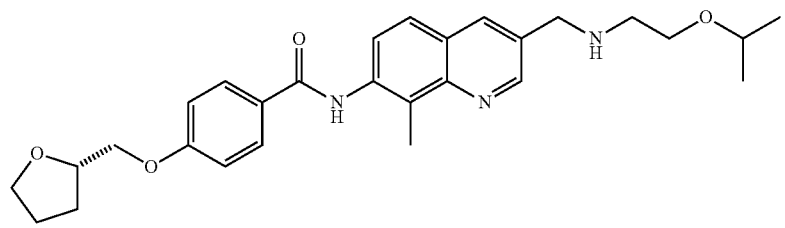

N-(3-Formyl-8-methylquinolin-7-yl)-4-[(2S)-tetrahydrofuran-2-ylmethoxy]benzamide (1.0 g) obtained in Reference Example 9 and 2-(1-methylethoxy)ethanamine (1.03 g) were suspended in 1-methyl-2-pyrrolidone (20 mL) and acetic acid (7.0 mL) and the mixture was stirred at room temperature for 3 hr. Sodium triacetoxyborohydride (2.33 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (280 mg, yield 23%) as a colorless solid.

$^1$H NMR (300 MHz, DMSO-$d_6$) δ: 1.08 (6H, d, J=6.0 Hz), 1.66-1.75 (1H, m), 1.82-1.94 (2H, m), 1.97-2.05 (1H, m), 2.26 (1H, br), 2.64 (3H, s), 2.65-2.69 (2H, m), 3.45 (2H, t, J=5.7 Hz), 3.49-3.57 (1H, m), 3.70 (1H, q, J=6.3 Hz), 3.80 (1H, q, J=6.3 Hz), 3.93 (2H, s), 3.98-4.10 (2H, m), 4.15-4.21 (1H, m), 7.08 (2H, d, J=8.7 Hz), 7.58 (1H, d, J=8.7 Hz), 7.77 (1H, d, J=8.7 Hz), 8.01 (2H, d, J=8.7 Hz), 8.20 (1H, s), 8.88 (1H, s), 10.04 (1H, s).

melting point: 111-113° C.
elemental analysis value ($C_{28}H_{35}N_3O_4 \cdot 2.0H_2O$)
Calculated: C, 65.48; H, 7.65; N, 8.18.
Found: C, 65.49; H, 7.48; N, 8.04.

Example 50

N-(3-{[(trans-4-hydroxy-4-methylcyclohexyl)amino]methyl}-8-methylquinolin-7-yl)-4-[(2S)-tetrahydrofuran-2-ylmethoxy]benzamide

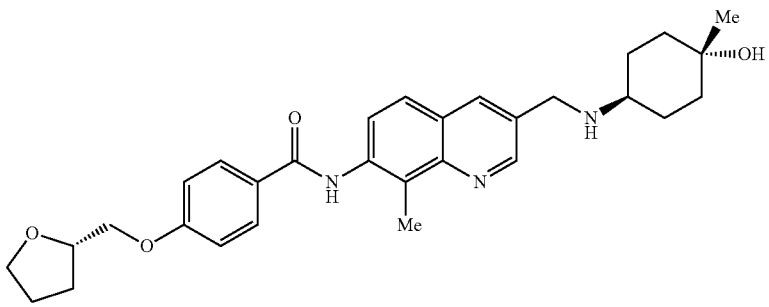 [SMILES: Cc1c(NC(=O)c2ccc(OC[C@@H]3CCCO3)cc2)ccc2cc(CN[C@H]3CC[C@](C)(O)CC3)cnc12]

N-(3-Formyl-8-methylquinolin-7-yl)-4-[(2S)-tetrahydrofuran-2-ylmethoxy]benzamide (1.00 g) obtained in Reference Example 9 and trans-4-amino-1-methylcyclohexanol (397 mg) obtained in Reference Example 15 were added to N,N-dimethylacetamide (10 mL), and the mixture was stirred at room temperature for 2 hr. The mixture was cooled to 5° C., acetic acid (0.440 mL) was added dropwise, sodium triacetoxyborohydride (1.19 g) was further added at the same temperature, and the mixture was stirred at room temperature for 5 hr. The reaction mixture was ice-cooled, 1N aqueous sodium hydroxide solution (25.6 mL) was added dropwise, and ethyl acetate (20 mL) was added. The precipitated crystals were collected by filtration, washed with ethyl acetate, and dried. The obtained crystals were recrystallized from ethyl acetate-water-n-heptane to give the title compound (1.18 g, yield 92%) as a colorless solid.

$^1$H NMR (300 MHz, DMSO-d$_6$) δ: 1.10 (3H, s), 1.18-1.37 (4H, m), 1.48-2.21 (9H, m), 2.43-2.49 (1H, m), 2.64 (3H, s), 3.65-3.85 (2H, m), 3.91 (2H, s), 3.97-4.14 (3H, m), 4.15-4.25 (1H, m), 7.09 (2H, d, J=8.7 Hz), 7.58 (1H, d, J=8.7 Hz), 7.77 (1H, d, J=8.7 Hz), 8.02 (2H, d, J=8.7 Hz), 8.20 (1H, d, J=1.9 Hz), 8.90 (1H, d, J=2.3 Hz), 10.06 (1H, s).

melting point: 169° C.

elemental analysis value (C$_{30}$H$_{37}$N$_3$O$_4$.1.4H$_2$O)

Calculated: C, 68.13; H, 7.59; N, 7.95.

Found: C, 68.07; H, 7.46; N, 7.81.

Example 50-1

N-(3-{[(trans-4-hydroxy-4-methylcyclohexyl)amino]methyl}-8-methylquinolin-7-yl)-4-[(2S)-tetrahydrofuran-2-ylmethoxy]benzamide N-(3-Formyl-8-methylquinolin-7-yl)-4-[(2S)-tetrahydrofuran-2-ylmethoxy]benzamide (6.3 kg) obtained in Reference Example 9 was suspended in N,N-dimethylacetamide (38 L), and trans-4-amino-1-methylcyclohexanol (2.5 kg) obtained in Reference Example 15 was added. Acetic acid (6.3 L) was added dropwise at 20-30° C., and the mixture was stirred at 20-30° C. for 1 hr. Under a nitrogen stream, sodium triacetoxyborohydride (5.13 kg) was added. The mixture was stirred at 20-30° C. for 3 hr 10 min and heated to 40° C., and 4N aqueous sodium hydroxide solution (38 L) was added dropwise at 40-55° C. for 20 min. After stirring at 45-55° C. for 30 min, the mixture was cooled to 30° C. over 35 min. After stirring at 20-30° C. for 1 hr, the reaction solution was filtered, and washed with clean water (63 L). After dried under reduced pressure, the crystals (7.77 kg) were obtained. 7.76 kg therefrom was suspended in ethanol (54 L), and dissolved by heating the suspension to 62° C. The solution was subjected to pressurization dust-removing filtration, and the filtered substance was washed with ethanol (16 L). The collected filtrate was heated again to 62° C. to dissolve the resulting precipitate. Purified water (31 L) was added dropwise at 60-65° C. and the mixture was cooled at 50° C. for 35 min. After stirring at 45-50° C. for 1 hr, the mixture was cooled at 30° C. for 35 min, and stirred at 20-30° C. for 1 hr. Furthermore, the mixture was cooled at 10° C. for 30 min and stirred at 0-10° C. for 2 hr. The precipitated crystals were collected by filtration, washed with purified water (16 L), and dried under reduced pressure to give the title compound (6.96 kg, yield 83%).

elemental analysis value (C$_{30}$H$_{37}$N$_3$O$_4$.1.3H$_2$O)

Calculated: C, 68.37; H, 7.57; N, 7.97.

Found: C, 68.28; H, 7.63; N, 7.95.

Example 50-2

N-(3-{[(trans-4-hydroxy-4-methylcyclohexyl)amino]methyl}-8-methylquinolin-7-yl)-4-[(2S)-tetrahydrofuran-2-ylmethoxy]benzamide N-(3-{[(trans-4-Hydroxy-4-methylcyclohexyl)amino]methyl}-8-methylquinolin-7-yl)-4-[(2S)-tetrahydrofuran-2-ylmethoxy]benzamide (16.0 g) obtained in Reference Example 50% was dissolved in ethanol (250 mL), and insoluble materials were filtered off. Ethyl acetate (1000 mL) was added to the filtrate and the mixture was purified by silica gel column chromatography [developing solvent; ethyl acetate:methanol=7:3 (volume ratio)]. From the obtained crude form (12.8 g), 12.0 g was dissolved in methanol (120 mL) at 55° C., and diluted with isopropyl ether (240 mL) at the same temperature. A seed crystal was added, and the mixture was allowed to cool to 5° C. The precipitated crystals were collected by filtration, washed with a mixture of methanol (20 mL) and isopropyl ether (40 mL) and dried to give the title compound (6.64 g) as colorless crystals.

$^1$H NMR (300 MHz, DMSO-d$_6$) δ: 1.10 (3H, s), 1.18-1.36 (4H, m), 1.47-2.09 (8H, m), 2.15 (1H, s), 2.43-2.50 (1H, m), 2.63 (3H, s), 3.65-3.85 (2H, m), 3.91 (2H, s), 3.98-4.11 (2H, m), 4.11 (1H, s), 4.15-4.24 (1H, m), 7.09 (2H, d, J=8.7 Hz), 7.57 (1H, d, J=8.7 Hz), 7.78 (1H, d, J=8.7 Hz), 8.02 (2H, d, J=9.1 Hz), 8.20 (1H, d, J=1.9 Hz), 8.90 (1H, d, J=2.3 Hz), 10.05 (1H, s).

melting point: 165° C.

elemental analysis value (C$_{30}$H$_{37}$N$_3$O$_4$)

Calculated: C, 71.54; H, 7.40; N, 8.34.

Found: C, 71.45; H, 7.35; N, 8.40.

Example 51

N-(3-{[(trans-4-hydroxy-4-methylcyclohexyl)amino]methyl}-8-methylquinolin-7-yl)-4-[(2R)-tetrahydrofuran-2-ylmethoxy]benzamide

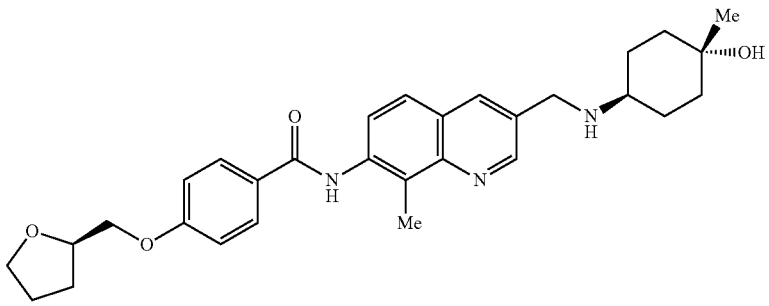 [SMILES: Cc1c(NC(=O)c2ccc(OC[C@H]3CCCO3)cc2)ccc2cc(CN[C@H]3CC[C@](C)(O)CC3)cnc12]

N-(3-Formyl-8-methylquinolin-7-yl)-4-[(2R)-tetrahydrofuran-2-ylmethoxy]benzamide (500 mg) obtained in Reference Example 6, trans-4-amino-1-methylcyclohexanol (331 mg) obtained in Reference Example 15 and acetic acid (2.57 mL) were added to N,N-dimethylacetamide (8 mL), and the mixture was stirred at room temperature for 1 hr. Sodium triacetoxyborohydride (543 mg) was added, and the mixture was stirred at room temperature for 15 hr. The reaction mixture was ice-cooled, 8N aqueous sodium hydroxide solution (6.40 mL) was added dropwise, and the mixture was partitioned and extracted with ethyl acetate. The aqueous layer was extracted with ethyl acetate, and the combined organic layer was washed with brine, and purified by silica gel column chromatography [developing solvent; ethyl acetate→ethyl acetate:methanol=3:2 (volume ratio)], and then NH-silica gel column chromatography [developing solvent; ethyl acetate→ethyl acetate:methanol=9:1 (volume ratio)]. The obtained solid was washed with a mixed solvent of ethyl acetate and isopropyl ether, and dried under reduced pressure to give the title compound (340 mg, yield 53%) as a pale-yellow solid.

$^1$H NMR (300 MHz, DMSO-$d_6$) δ: 1.10 (3H, s), 1.21-1.37 (4H, m), 1.48-2.10 (9H, m), 2.44-2.53 (1H, m), 2.64 (3H, s), 3.65-3.85 (2H, m), 3.91 (2H, s), 3.98-4.09 (2H, m), 4.10 (1H, s), 4.15-4.24 (1H, m), 7.09 (2H, d, J=9.0 Hz), 7.58 (1H, d, J=9.0 Hz), 7.77 (1H, d, J=8.7 Hz), 8.02 (2H, d, J=8.7 Hz), 8.20 (1H, d, J=1.9 Hz), 8.90 (1H, d, J=2.3 Hz), 10.04 (1H, s).

melting point: 167° C.

Example 52

N-(3-{[(cis-4-hydroxy-4-methylcyclohexyl)amino]methyl}-8-methylquinolin-7-yl)-4-[(2S)-tetrahydrofuran-2-ylmethoxy]benzamide

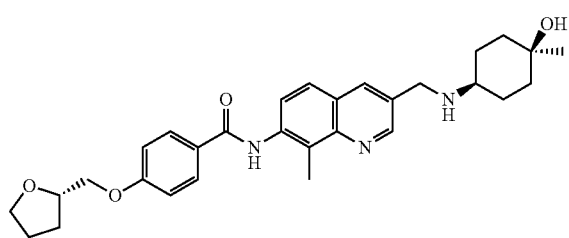 [SMILES: Cc1c(NC(=O)c2ccc(OC[C@@H]3CCCO3)cc2)ccc2cc(CN[C@H]3CC[C@@](C)(O)CC3)cnc12]

N-(3-Formyl-8-methylquinolin-7-yl)-4-[(2S)-tetrahydrofuran-2-ylmethoxy]benzamide (390 mg) obtained in Reference Example 9 and cis-4-amino-1-methylcyclohexanol (262 mg) obtained in Reference Example 14 were dissolved in 1-methyl-2-pyrrolidone (3.0 mL), acetic acid (1.0 mL) was added, and the mixture was stirred at room temperature for 8 hr. Sodium triacetoxyborohydride (424 mg) was added, and the mixture was stirred at room temperature for 15 hr. The mixture was diluted with ethyl acetate and 2N aqueous sodium hydroxide solution (20 mL) was added dropwise at room temperature. The mixture was poured into water, and the organic layer was washed with water and saturated brine, dried over sodium sulfate and concentrated under reduced pressure. The residue was purified by NH silica gel column chromatography [developing solvent; ethyl acetate:methanol=100:0 (volume ratio)→ethyl acetate:methanol=85:15 (volume ratio)], and the obtained solid was recrystallized from ethyl acetate to give the title compound (205 mg, yield 41%) as a pale-yellow solid.

$^1$H NMR (300 MHz, CDCl$_3$) δ: 1.23 (3H, s), 1.34-1.52 (4H, m), 1.69 (2H, d, J=11.7 Hz), 1.75-1.89 (3H, m), 1.92-2.05 (2H, m), 2.05-2.19 (1H, m), 2.46-2.58 (1H, m), 2.81 (3H, s), 3.81-3.91 (1H, m), 3.92-4.01 (1H, m), 4.04 (2H, s), 4.06 (2H, d, J=5.3 Hz), 4.26-4.39 (1H, m), 7.05 (2H, d, J=8.7 Hz), 7.70 (1H, d, J=9.0 Hz), 7.89 (1H, s), 7.92 (2H, d, J=8.7 Hz), 8.06 (1H, d, J=2.3 Hz), 8.25 (1H, d, J=9.0 Hz), 8.89 (1H, d, J=1.9 Hz).

melting point: 159-161° C.

elemental analysis value (C$_{30}$H$_{37}$N$_3$O$_4$.0.2H$_2$O)

Calculated: C, 71.04; H, 7.43; N, 8.28.

Found: C, 71.10; H, 7.45; N, 8.11.

Example 53

N-(3-{[(cis-4-hydroxy-4-methylcyclohexyl)amino]methyl}-8-methylquinolin-7-yl)-4-[(2R)-tetrahydrofuran-2-ylmethoxy]benzamide

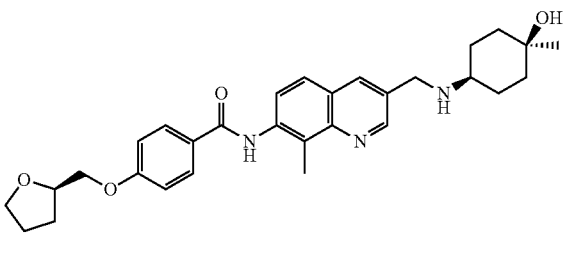 [SMILES: Cc1c(NC(=O)c2ccc(OC[C@H]3CCCO3)cc2)ccc2cc(CN[C@H]3CC[C@@](C)(O)CC3)cnc12]

N-(3-Formyl-8-methylquinolin-7-yl)-4-[(2R)-tetrahydrofuran-2-ylmethoxy]benzamide (390 mg) obtained in Reference Example 6 and cis-4-amino-1-methylcyclohexanol (262 mg) obtained in Reference Example 14 were dissolved in 1-methyl-2-pyrrolidone (3.0 mL), acetic acid (1.0 mL) was added, and the mixture was stirred at room temperature for 8 hr. Sodium triacetoxyborohydride (424 mg) was added, and the mixture was stirred at room temperature for 15 hr. The mixture was diluted with ethyl acetate and 2N aqueous sodium hydroxide solution (20 mL) was added dropwise at room temperature. The mixture was poured into water, and the organic layer was washed with water and saturated brine, dried over sodium sulfate and concentrated under reduced pressure. The residue was purified by NH silica gel column chromatography [developing solvent; ethyl acetate:methanol=100:0 (volume ratio)→ethyl acetate:methanol=85:15 (volume ratio)] and the obtained solid was recrystallized from ethyl acetate to give the title compound (238 mg, yield 47%) as a pale-yellow solid.

$^1$H NMR (300 MHz, CDCl$_3$) δ: 1.22 (3H, s), 1.34-1.51 (4H, m), 1.64-1.75 (2H, m), 1.75-1.88 (3H, m), 1.91-2.04 (2H, m), 2.05-2.19 (1H, m), 2.45-2.58 (1H, m), 2.81 (3H, s), 3.81-3.91 (1H, m), 3.92-4.01 (1H, m), 4.04 (2H, s), 4.06 (2H, d, J=5.3 Hz), 4.26-4.38 (1H, m), 7.05 (2H, d, J=9.0 Hz), 7.70 (1H, d, J=8.7 Hz), 7.89 (1H, br. s.), 7.92 (2H, d, J=8.7 Hz), 8.06 (1H, d, J=1.9 Hz), 8.25 (1H, d, J=8.7 Hz), 8.89 (1H, d, J=2.3 Hz).

melting point: 163-164° C.

elemental analysis value (C$_{30}$H$_{37}$N$_3$O$_4$)

Calculated: C, 71.54; H, 7.40; N, 8.34.

Found: C, 71.24; H, 7.24; N, 8.13.

Example 54

N-(3-{[(1-ethylpropyl)amino]methyl}-8-methylquinolin-7-yl)-4-[(2S)-tetrahydrofuran-2-ylmethoxy]benzamide

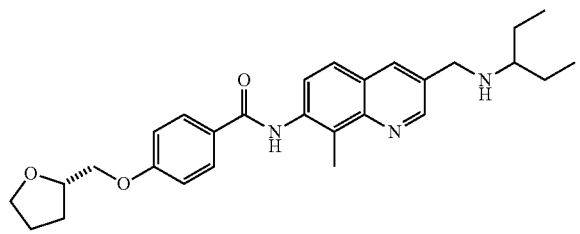

N-(3-Formyl-8-methylquinolin-7-yl)-4-[(2S)-tetrahydrofuran-2-ylmethoxy]benzamide (1.0 g) obtained in Reference Example 9 and pentan-3-amine (872 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (362 mg, yield 31%) as a colorless solid.

$^1$H NMR (300 MHz, DMSO-$d_6$) δ: 0.85 (6H, d, J=7.5 Hz), 1.37-1.46 (4H, m), 1.66-1.75 (1H, m), 1.84-1.94 (2H, m), 1.98-2.06 (1H, m), 2.34-2.38 (2H, m), 2.64 (3H, s), 3.69 (1H, q, J=6.9 Hz), 3.80 (1H, q, J=6.9 Hz), 3.90 (2H, s), 3.98-4.10 (2H, m), 4.17-4.21 (1H, m), 7.08 (2H, d, J=8.7 Hz), 7.56 (1H, d, J=8.7 Hz), 7.77 (1H, d, J=8.7 Hz), 8.01 (2H, d, J=8.7 Hz), 8.20 (1H, s), 8.91 (1H, s), 10.04 (1H, s).

melting point: 113-115° C.
elemental analysis value ($C_{28}H_{35}N_3O_3$·0.2$H_2O$)
Calculated: C, 72.29; H, 7.67; N, 9.03.
Found: C, 72.44; H, 7.55; N, 9.06.

Example 55

N-[8-methyl-3-({[(1R)-1-methylpropyl]amino}methyl)quinolin-7-yl]-4-[(2S)-tetrahydrofuran-2-ylmethoxy]benzamide

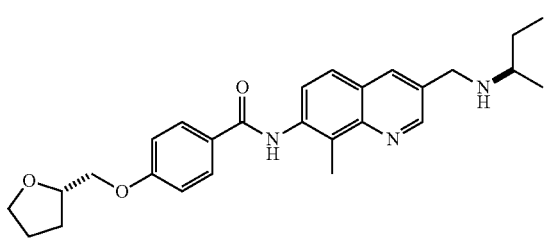

N-(3-Formyl-8-methylquinolin-7-yl)-4-[(2S)-tetrahydrofuran-2-ylmethoxy]benzamide (1.0 g) obtained in Reference Example 9 and (2R)-butan-2-amine (500 mg) were suspended in 1-methyl-2-pyrrolidone (20 mL) and acetic acid (7.0 mL) and the mixture was stirred at room temperature for 3 hr. Sodium triacetoxyborohydride (2.35 g) was added and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (362 mg, yield 34%) as a colorless solid.

$^1$H NMR (300 MHz, DMSO-$d_6$) δ: 0.86 (3H, t, J=7.5 Hz), 1.03 (3 d, J=6.0 Hz), 1.29-1.36 (1H, m), 1.46-1.53 (1H, m), 1.66-1.73 (1H, m), 1.75-1.92 (2H, m), 1.94-2.06 (1H, m), 2.49-2.58 (2H, m), 2.64 (3H, s), 3.69 (1H, q, J=6.9 Hz), 3.80 (1H, q, J=6.9 Hz), 3.92 (2H, d, J=7.8 Hz), 3.98-4.10 (2H, m), 4.17-4.21 (1H, m), 7.08 (2H, d, J=9.0 Hz), 7.57 (1H, d, J=9.0 Hz), 7.77 (1H, d, J=9.0 Hz), 8.01 (2H, d, J=9.0 Hz), 8.20 (1H, s), 8.90 (1H, s), 10.04 (1H, s).

melting point: 118-119° C.
elemental analysis value ($C_{27}H_{33}N_3O_3$·1.6$H_2O$)
Calculated: C, 68.07; H, 7.66; N, 8.82.
Found: C, 68.79; H, 7.33; N, 8.69.

Example 56

N-[8-methyl-3-({[(1S)-1-methylpropyl]amino}methyl)quinolin-7-yl]-4-[(2S)-tetrahydrofuran-2-ylmethoxy]benzamide

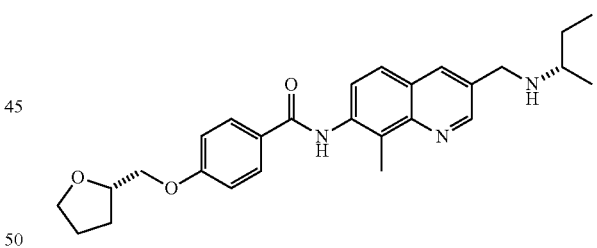

N-(3-Formyl-8-methylquinolin-7-yl)-4-[(2S)-tetrahydrofuran-2-ylmethoxy]benzamide (2.0 g) obtained in Reference Example 9 and (2S)-butan-2-amine (1.0 g) were suspended in 1-methyl-2-pyrrolidone (20 mL) and acetic acid (7.0 mL) and the mixture was stirred at room temperature for 3 hr. Sodium triacetoxyborohydride (4.67 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 ml), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (820 mg, yield 36%) as a colorless solid.

$^1$H NMR (300 MHz, DMSO-d$_6$) δ: 0.86 (3H, t, J=7.5 Hz), 1.03 (3H, d, J=6.3 Hz), 1.28-1.35 (1H, m), 1.44-1.53 (1H, m), 1.66-1.75 (1H, m), 1.82-1.92 (2H, m), 1.97-2.05 (2H, m), 2.53-2.56 (1H, m), 2.64 (3H, s), 3.69 (1H, q, J=6.3 Hz), 3.80 (1H, q, J=6.3 Hz), 3.90 (2H, d, J=7.5 Hz), 3.97-4.09 (2H, m), 4.17-4.21 (1H, m), 7.08 (2H, d, J=8.7 Hz), 7.56 (1H, d, J=8.7 Hz), 7.76 (1H, d, J=8.7 Hz), 8.01 (2H, d, J=8.7 Hz), 8.19 (1H, s), 8.89 (1H, s), 10.02 (1H, s).

melting point: 122-123° C.

elemental analysis value (C$_{27}$H$_{33}$N$_3$O$_3$·0.4H$_2$O)

Calculated: C, 71.31; H, 7.49; N, 9.24.

Found: C, 71.53; H, 7.46; N, 9.09.

Example 57

N-{3-[(cyclobutylamino)methyl]-8-methylquinolin-7-yl}-4-[(2S)-tetrahydrofuran-2-ylmethoxy]benzamide

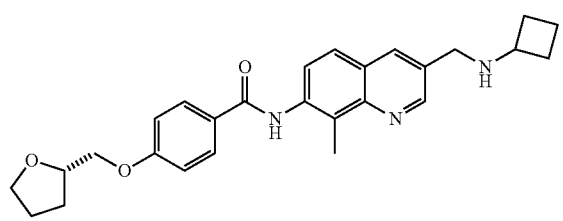

N-(3-Formyl-8-methylquinolin-7-yl)-4-[(2S)-tetrahydrofuran-2-ylmethoxy]benzamide (1.0 g) obtained in Reference Example 9 and cyclobutanamine (800 mg) were suspended in 1-methyl-2-pyrrolidone (20 mL) and acetic acid (7.0 mL) and the mixture was stirred at room temperature for 3 hr. Sodium triacetoxyborohydride (2.33 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (302 mg, yield 26%) as a colorless solid.

$^1$H NMR (300 MHz, DMSO-d$_6$) δ: 1.52-1.75 (5H, m), 1.82-1.94 (2H, m), 1.98-2.12 (3H, m), 2.49-2.50 (1H, m), 2.63 (3H, s), 3.17-3.22 (1H, m), 3.69 (1H, q, J=6.3 Hz), 3.77-3.81 (3H, m), 4.00-4.10 (2H, m), 4.17-4.21 (1H, m), 7.08 (2H, d, J=8.7 Hz), 7.57 (1H, d, J=8.7 Hz), 7.77 (1H, d, J=8.7 Hz), 8.01 (2H, d, J=8.7 Hz), 8.18 (1H, s), 8.86 (1H, s), 10.04 (1H, s).

melting point: 142-144° C.

elemental analysis value (C$_{27}$H$_{31}$N$_3$O$_3$·0.2H$_2$O)

Calculated: C, 72.20; H, 7.05; N, 9.36.

Found: C, 72.26; H, 7.07; N, 9.37.

Example 58

N-[8-methyl-3-({[(1R)-1,2,2-trimethylpropyl]amino}methyl)quinolin-7-yl]-4-[(2S)-tetrahydrofuran-2-ylmethoxy]benzamide

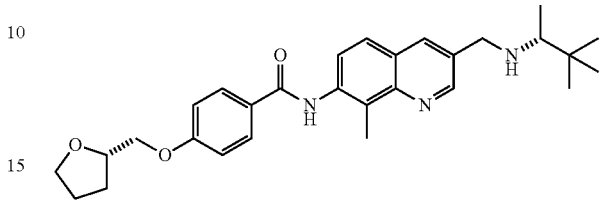

N-(3-Formyl-8-methylquinolin-7-yl)-4-[(2S)-tetrahydrofuran-2-ylmethoxy]benzamide (2.0 g) obtained in Reference Example 9 and (R)-(−)-3,3-dimethyl-2-butylamine (2.0 g) were suspended in 1-methyl-2-pyrrolidone (20 mL) and acetic acid (7.0 mL) and the mixture was stirred at room temperature for 3 hr. Sodium triacetoxyborohydride (4.7 g) was added, and the mixture was stirred at room temperature for 3 hr. 1N Aqueous sodium hydroxide solution was added to quench the reaction and basify the mixture. The mixture was partitioned and extracted with ethyl acetate, the organic layer was added to a solution of citric acid (4.0 g) in water (40 mL)-dimethyl sulfoxide (20 mL), and the mixture was washed with ethyl acetate. 1N Aqueous sodium hydroxide solution was added to the aqueous layer, and the mixture was partitioned and extracted with ethyl acetate. The organic layer was washed with saturated brine and dried over anhydrous magnesium sulfate, and the solvent was evaporated under reduced pressure. The obtained solid was recrystallized from ethyl acetate-diisopropyl ether to give the title compound (520 mg, yield 21%) as a colorless solid.

$^1$H NMR (300 MHz, DMSO-d$_6$) δ: 0.85 (9H, s), 0.98 (3H, d, J=6.6 Hz), 1.66-1.91 (4H, m), 1.98-2.06 (1H, m), 2.17-2.19 (1H, m), 2.49-2.50 (1H, m), 2.64 (3H, s), 3.69 (1H, q, J=6.3 Hz), 3.77-3.83 (3H, m), 3.99-4.08 (2H, m), 4.15-4.19 (1H, m), 7.08 (2H, d, J=8.7 Hz), 7.57 (1H, d, J=8.7 Hz), 7.77 (1H, d, J=8.7 Hz), 8.01 (2H, d, J=8.7 Hz), 8.19 (1H, s), 8.92 (1H, s), 10.03 (1H, s).

melting point: 140-141° C.

elemental analysis value (C$_{29}$H$_{37}$N$_3$O$_3$)

Calculated: C, 73.23; H, 7.84; N, 8.83.

Found: C, 73.09; H, 7.68; N, 8.66.

Example 59

N-(8-methyl-3-{[(2-methylpropyl)amino]methyl}quinolin-7-yl)-4-(tetrahydrofuran-3-ylmethoxy)benzamide

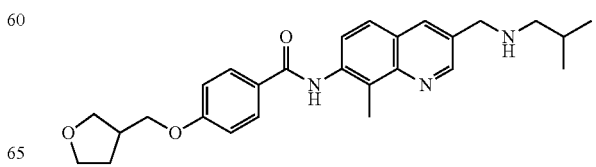

N-(3-Formyl-8-methylquinolin-7-yl)-4-(tetrahydrofuran-3-ylmethoxy)benzamide (1.776 g) obtained in Reference Example 4 and 2-methylpropan-1-amine (435 mg) were added to a mixed solvent of 1-methyl-2-pyrrolidone (10 mL) and acetic acid (3.0 mL), and the mixture was stirred at room temperature for 3 hr. Sodium triacetoxyborohydride (1.682 g) was added, and the mixture was stirred at room temperature for 89 hr. The mixture was diluted with ethyl acetate, and 4N aqueous sodium hydroxide solution (40 mL) was added dropwise. The organic layer was washed twice with water and then with saturated brine, dried over sodium sulfate and concentrated under reduced pressure. The residue was suspended in ice-cooled ethyl acetate, and the precipitate was collected by filtration, washed with ice-cooled ethyl acetate and dried under reduced pressure to give the title compound (890 mg, yield 50%) as a pale-brown solid.

$^1$H NMR (300 MHz, CDCl$_3$) δ: 0.94 (6H, d, J=6.6 Hz), 1.70-1.88 (2H, m), 2.08-2.24 (1H, m), 2.49 (2H, d, J=6.8 Hz), 2.72-2.88 (4H, m), 3.70-3.86 (2H, m), 3.86-4.07 (6H, m), 7.01 (2H, d, J=8.9 Hz), 7.71 (1H, d, J=8.7 Hz), 7.85-7.98 (3H, m), 8.06 (1H, d, J=2.1 Hz), 8.25 (1H, d, J=8.9 Hz), 8.90 (1H, d, J=2.3 Hz).

melting point: 132° C.
elemental analysis value (C$_{27}$H$_{33}$N$_3$O$_3$.0.7H$_2$O)
Calculated: C, 70.47; H, 7.53; N, 9.13.
Found: C, 70.51; H, 7.35; N, 9.07.

Example 60 and Example 61

N-(8-methyl-3-{[(2-methylpropyl)amino]methyl}quinolin-7-yl)-4-(tetrahydrofuran-3-ylmethoxy)benzamide

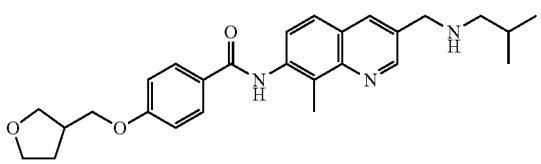 [SMILES: Cc1c(NC(=O)c2ccc(OCC3CCOC3)cc2)ccc2cc(CNCC(C)C)cnc12]

N-(8-Methyl-3-{[(2-methylpropyl)amino]methyl}quinolin-7-yl)-4-(tetrahydrofuran-3-ylmethoxy)benzamide (695 mg) obtained in Example 59 was optically resolved by HPLC [column: CHIRALCEL OJ 4.6 mmID× 250 mL, mobile phase: hexane:ethanol:diethylamine=700:300:1 (volume ratio)], and recrystallized from ethyl acetate/diisopropyl ether to give a component with short retention time (Example 60, 253 mg (99.4% ee)) as a colorless solid and a component with long retention time (Example 61, 210 mg (98.3% ee)) as a colorless solid.

Component with Short Retention Time:
$^1$H NMR (300 MHz, CDCl$_3$) δ: 0.94 (6H, d), 1.69-1.87 (2H, m), 2.08-2.23 (1H, m), 2.49 (2H, d, J=6.4 Hz), 2.71-2.87 (4H, m), 3.70-3.86 (2H, m), 3.88-4.06 (6H, m), 7.01 (2H, d, J=9.1 Hz), 7.71 (1H, d, J=8.7 Hz), 7.89 (1H, s), 7.92 (2H, d, J=8.7 Hz), 8.05 (1H, d, J=2.3 Hz), 8.25 (1H, d, J=8.7 Hz), 8.90 (1H, d, J=2.3 Hz).

melting point: 133-134° C.
Component with Long Retention:
$^1$H NMR (300 MHz, CDCl$_3$) δ: 0.94 (6H, d), 1.70-1.89 (2H, m), 2.06-2.23 (1H, m), 2.49 (2H, d, J=6.8 Hz), 2.70-2.88 (4H, m), 3.70-3.86 (2H, m), 3.88-4.07 (6H, m), 7.01 (2H, d, J=8.7 Hz), 7.71 (1H, d, J=9.1 Hz), 7.89 (1H, s), 7.92 (2H, d, J=8.7 Hz), 8.05 (1H, d, J=1.9 Hz), 8.25 (1H, d, J=8.7 Hz), 8.90 (1H, d, J=2.3 Hz).

melting point: 130-131° C.
elemental analysis value (C$_{27}$H$_{33}$N$_3$O$_3$.0.2H$_2$O)
Calculated: C, 71.88; H, 7.46; N, 9.31.
Found: C, 72.08; H, 7.48; N, 9.25.

Example 62

N-(3-{[(2,2-dimethylpropyl)amino]methyl}-8-methylquinolin-7-yl)-4-(tetrahydrofuran-3-ylmethoxy)benzamide

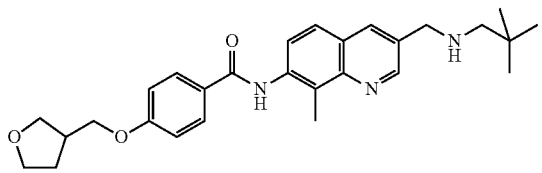 [SMILES: Cc1c(NC(=O)c2ccc(OCC3CCOC3)cc2)ccc2cc(CNCC(C)(C)C)cnc12]

N-(3-Formyl-8-methylquinolin-7-yl)-4-(tetrahydrofuran-3-ylmethoxy)benzamide (1.776 g) obtained in Reference Example 4 and 2,2-dimethylpropan-1-amine (519 mg) were added to a mixed solvent of 1-methyl-2-pyrrolidone (10 mL) and acetic acid (3.0 mL), and the mixture was stirred at room temperature for 3 hr. Sodium triacetoxyborohydride (1.682 g) was added, and the mixture was stirred at room temperature for 89 hr. The mixture was diluted with ethyl acetate, and 4N aqueous sodium hydroxide solution (40 mL) was added dropwise. The organic layer was washed twice with water and then with saturated brine, dried over sodium sulfate and concentrated under reduced pressure. The residue was purified by silica gel column chromatography [developing solvent; ethyl acetate:methanol=97:3 (volume ratio)→ethyl acetate:methanol=90:10 (volume ratio)] and the obtained solid was suspended in an ice-cooled mixed solvent of ethyl acetate-diisopropyl ether. The precipitate was collected by filtration, washed with diisopropyl ether, and dried under reduced pressure to give the title compound (526 mg, yield 29%) as a pale-brown solid.

$^1$H NMR (300 MHz, CDCl$_3$) δ: 0.93 (9H, s), 1.70-1.85 (1H, m), 2.08-2.23 (1H, m), 2.40 (2H, s), 2.71-2.87 (4H, m), 3.71-3.86 (2H, m), 3.88-4.07 (6H, m), 7.01 (2H, d, J=8.9 Hz), 7.71 (1H, d, J=8.9 Hz), 7.86-7.97 (3H, m), 8.05 (1H, d, J=2.3 Hz), 8.24 (1H, d, J=8.9 Hz), 8.92 (1H, d, J=2.3 Hz).

melting point: 129° C.
elemental analysis value (C$_{28}$H$_{35}$N$_3$O$_3$.0.1H$_2$O)
Calculated: C, 72.57; H, 7.66; N, 9.07.
Found: C, 72.41; H, 7.56; N, 9.01.

Example 63

N-(8-methyl-3-{[(tetrahydro-2H-pyran-4-ylmethyl)amino]methyl}quinolin-7-yl)-4-(tetrahydrofuran-3-ylmethoxy)benzamide

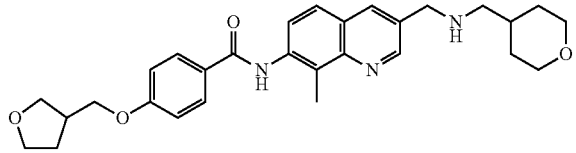 [SMILES: Cc1c(NC(=O)c2ccc(OCC3CCOC3)cc2)ccc2cc(CNCC3CCOCC3)cnc12]

N-(3-Formyl-8-methylquinolin-7-yl)-4-(tetrahydrofuran-3-ylmethoxy)benzamide (1.776 g) obtained in Reference Example 4 and 1-(tetrahydro-2H-pyran-4-yl)methanamine (686 mg) were added to a mixed solvent of 1-methyl-2-pyrrolidone (10 mL) and acetic acid (3.0 mL), and the mixture was stirred at room temperature for 3 hr. Sodium triacetoxyborohydride (1.682 g) was added, and the mixture was stirred at room temperature for 89 hr. The mixture was diluted with ethyl acetate, and 4N aqueous sodium hydroxide solution (40 mL) was added dropwise. The organic layer was washed twice with water and then with saturated brine, dried over sodium sulfate and concentrated under reduced pressure. The residue was purified by silica gel column chromatography [developing solvent; ethyl acetate:methanol=90:10 (volume ratio)→ethyl acetate:methanol=20:80 (volume ratio)] and the obtained solid was suspended in ice-cooled ethyl acetate. The precipitate was collected by filtration, washed with ice-cooled ethyl acetate and dried under reduced pressure to give the title compound (1.415 g, yield 73%) as a pale-brown solid.

$^1$H NMR (300 MHz, CDCl$_3$) δ: 1.32 (2H, qd, J=12.0, 3.9 Hz), 1.63-1.85 (4H, m), 2.08-2.23 (1H, m), 2.57 (2H, s), 2.72-2.86 (4H, m), 3.39 (2H, td, J=11.8, 2.1 Hz), 3.70-3.86 (2H, m), 3.88-4.06 (8H, m), 7.01 (2H, d, J=8.9 Hz), 7.71 (1H, d, J=8.9 Hz), 7.86-7.96 (3H, m), 8.06 (1H, d, J=2.1 Hz), 8.26 (1H, d, J=8.9 Hz), 8.90 (1H, d, J=2.3 Hz).

melting point: 122-123° C.
elemental analysis value (C$_{29}$H$_{35}$N$_3$O$_4$.H$_2$O)
Calculated: C, 68.62; H, 7.35; N, 8.28.
Found: C, 68.76; H, 7.07; N, 8.27.

Example 64

N-(3-{[(trans-4-hydroxy-4-methylcyclohexyl)amino]methyl}-8-methylquinolin-7-yl)-4-(tetrahydrofuran-3-ylmethoxy)benzamide

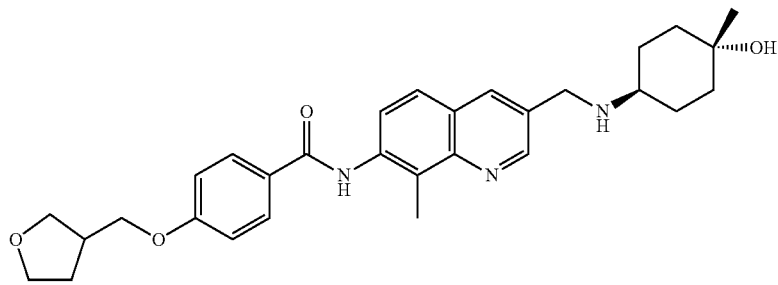 [SMILES: Cc1c(NC(=O)c2ccc(OCC3CCOC3)cc2)ccc2cc(CN[C@H]3CC[C@](C)(O)CC3)cnc12]

N-(3-Formyl-8-methylquinolin-7-yl)-4-(tetrahydrofuran-3-ylmethoxy)benzamide (390 mg) obtained in Reference Example 4 and trans-4-amino-1-methylcyclohexanol (129 mg) obtained in Reference Example 15 were dissolved in 1-methyl-2-pyrrolidone (3.0 mL), acetic acid (1.0 mL) was added, and the mixture was stirred at room temperature for 3 hr. Sodium triacetoxyborohydride (424 mg) was added, and the mixture was stirred at room temperature for 14 hr. The mixture was diluted with ethyl acetate, and 2N aqueous sodium hydroxide solution (16 mL) was added dropwise. The mixture was poured into water, and the organic layer was washed with water and saturated brine, dried over sodium sulfate and concentrated under reduced pressure. The residue was purified by silica gel column chromatography [developing solvent; ethyl acetate:methanol=90:10 (volume ratio)→ethyl acetate:methanol=40:60 (volume ratio)], and the obtained solid was recrystallized from ethyl acetate and dried under reduced pressure to give the title compound (226 mg, yield 45%) as a colorless solid.

$^1$H NMR (300 MHz, CDCl$_3$) δ: 1.28 (3H, s), 1.33-1.52 (5H, m), 1.69-1.83 (3H, m), 1.86-1.99 (2H, m), 2.08-2.23 (1H, m), 2.64-2.87 (5H, m), 3.70-4.08 (9H, m), 7.01 (2H, d, J=8.7 Hz), 7.71 (1H, d, J=9.1 Hz), 7.85-7.96 (3H, m), 8.05 (1H, d, J=2.3 Hz), 8.26 (1H, d, J=8.7 Hz), 8.90 (1H, d, J=2.3 Hz).

melting point: 98-101° C.
elemental analysis value (C$_{30}$H$_{37}$N$_3$O$_4$.1.6H$_2$O)
Calculated: C, 67.67; H, 7.61; N, 7.89.
Found: C, 67.68; H, 7.43; N, 7.69.

Example 65

N-(3-{[(2-methoxy-2-methylpropyl)amino]methyl}-8-methylquinolin-7-yl)-4-(tetrahydrofuran-3-ylmethoxy)benzamide

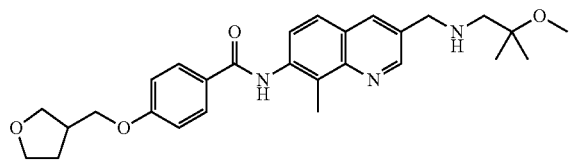 [SMILES: COC(C)(C)CNCc1cnc2c(C)c(NC(=O)c3ccc(OCC4CCOC4)cc3)ccc2c1]

N-(3-Formyl-8-methylquinolin-7-yl)-4-(tetrahydrofuran-3-ylmethoxy)benzamide (1.420 g) obtained in Reference Example 4 and 2-methoxy-2-methylpropan-1-amine oxalate 0.5 hydrate (921 mg) were dissolved in 1-methyl-2-pyrrolidone (10 mL), triethylamine (0.61 mL) was added, and the mixture was stirred at room temperature for 1.5 hr. Acetic acid (3.0 mL) was added, and the mixture was stirred at room temperature for 4.5 hr. Sodium triacetoxyborohydride (1.541 g) was added, and the mixture was stirred at room temperature for 63 hr. The mixture was diluted with ethyl acetate, and 4N aqueous sodium hydroxide solution (30 mL) was added dropwise at 0° C. The mixture was poured into water, and the organic layer was washed with water and saturated brine, dried over sodium sulfate and concentrated under reduced pressure. The residue was purified by silica gel column chromatography [developing solvent; ethyl acetate:methanol=90:10 (volume ratio)→ethyl acetate:methanol=75:25 (volume ratio)] and purified by NH silica gel column chromatography [developing solvent; ethyl acetate:methanol=100:0 (volume ratio)→ethyl acetate:methanol=96:4 (volume ratio)]. The obtained solid was recrystallized from ethyl acetate to give the title compound (1.119 g, yield 64%) as a pale-yellow solid.

¹H NMR (300 MHz, CDCl₃) δ: 1.20 (6H, s), 1.70-1.84 (1H, m), 2.07-2.23 (1H, m), 2.61 (2H, s), 2.72-2.87 (4H, m), 3.18 (3H, s), 3.70-3.87 (2H, m), 3.87-4.08 (6H, m), 7.01 (2H, d, J=8.7 Hz), 7.71 (1H, d, J=9.1 Hz), 7.85-7.97 (3H, m), 8.06 (1H, d, J=2.3 Hz), 8.25 (1H, d, J=9.1 Hz), 8.92 (1H, d, J=2.3 Hz).

melting point: 137° C.

elemental analysis value ($C_{28}H_{35}N_3O_4$)

Calculated: C, 70.42; H, 7.39; N, 8.80.

Found: C, 69.15; H, 7.36; N, 8.70.

Example 66

N-{3-[(4-hydroxy-4-methylpiperidin-1-yl)methyl]-8-methylquinolin-7-yl}-4-(tetrahydrofuran-3-ylmethoxy)benzamide

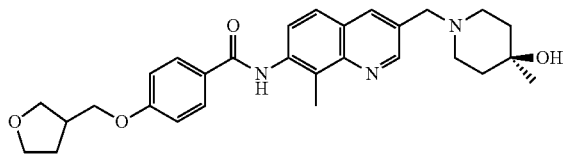

N-(3-Formyl-8-methylquinolin-7-yl)-4-(tetrahydrofuran-3-ylmethoxy)benzamide (1.420 g) obtained in Reference Example 4 and 4-methylpiperidin-4-ol monohydrochloride (661 mg) obtained in Reference Example 17 were dissolved in 1-methyl-2-pyrrolidone (10 mL), triethylamine (0.61 mL) was added, and the mixture was stirred at room temperature for 1.5 hr. Acetic acid (3.0 mL) was added, and the mixture was stirred at room temperature for 4.5 hr. Sodium triacetoxyborohydride (1.541 g) was added, and the mixture was stirred at room temperature for 63 hr. The mixture was diluted with ethyl acetate, and 4N aqueous sodium hydroxide solution (30 mL) was added dropwise at 0° C. The mixture was poured into water, and the organic layer was washed with water and saturated brine, dried over sodium sulfate and concentrated under reduced pressure. The residue was purified by silica gel column chromatography [developing solvent; ethyl acetate:methanol=90:10 (volume ratio)→ethyl acetate:methanol=40:60 (volume ratio)] and the obtained solid was recrystallized from ethyl acetate to give the title compound (421 mg, yield 24%) as a pale-yellow solid.

¹H NMR (300 MHz, CDCl₃) δ: 1.17 (1H, s), 1.25 (3H, s), 1.58-1.85 (5H, m), 2.08-2.23 (1H, m), 2.45 (2H, td, J=10.8, 3.0 Hz), 2.55-2.66 (2H, m), 2.73-2.86 (4H, m), 3.68-3.86 (4H, m), 3.88-4.07 (4H, m), 7.01 (2H, d, J=8.7 Hz), 7.70 (1H, d, J=9.1 Hz), 7.86-7.97 (3H, m), 8.03 (1H, d, J=1.9 Hz), 8.26 (1H, d, J=9.1 Hz), 8.90 (1H, d, J=2.3 Hz).

melting point: 160-162° C.

elemental analysis value ($C_{29}H_{35}N_3O_4 \cdot 0.3H_2O$)

Calculated: C, 70.36; H, 7.25; N, 8.49.

Found: C, 70.42; H, 7.07; N, 8.43.

Example 67

2-fluoro-N-(3-{[(2-hydroxy-2-methylpropyl)amino]methyl}-8-methylquinolin-7-yl)-4-[(2S)-tetrahydrofuran-2-ylmethoxy]benzamide

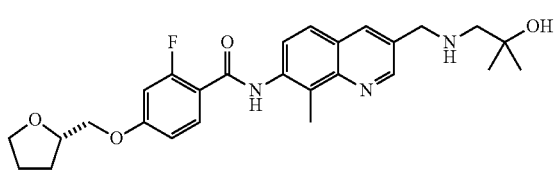 [SMILES: Cc1c(NC(=O)c2ccc(OC[C@@H]3CCCO3)cc2F)ccc2cc(CNCC(C)(C)O)cnc12]

2-Fluoro-N-(3-formyl-8-methylquinolin-7-yl)-4-[(2S)-tetrahydrofuran-2-ylmethoxy]benzamide (1.5 g) obtained in Reference Example 12 and 1-amino-2-methylpropan-2-ol (982 mg) were suspended in 1-methyl-2-pyrrolidone (20 mL) and acetic acid (7.0 mL) and the mixture was stirred at room temperature for 3 hr. Sodium triacetoxyborohydride (3.0 g) was added, and the mixture was stirred at room temperature for 3 hr. 1N Aqueous sodium hydroxide solution was added to quench the reaction and basify the mixture, and the mixture was partitioned and extracted with ethyl acetate. The organic layer was washed with saturated brine and dried over anhydrous sodium sulfate, and the solvent was evaporated under reduced pressure. The residue was purified by silica gel column chromatography [developing solvent; methanol:ethyl acetate=0:100 (volume ratio)→methanol:ethyl acetate=20:80 (volume ratio)] to give the title compound (900 mg, yield 51%) as a colorless solid.

¹H NMR (300 MHz, DMSO-d₆) δ: 1.11 (6H, s), 1.64-1.73 (1H, m), 1.83-1.93 (2H, m), 1.97-2.05 (1H, m), 2.16 (1H, br), 2.41 (2H, s), 2.67 (3H, s), 3.69 (1H, q, J=6.9 Hz), 3.79 (1H, q, J=6.9 Hz), 3.94 (2H, s), 3.99-4.11 (2H, m), 4.14-4.20 (2H, m), 6.91-7.02 (2H, m), 7.70-7.79 (3H, m), 8.18 (1H, d, J=1.8 Hz), 8.90 (1H, d, J=2.4 Hz), 9.89 (1H, d, J=2.4 Hz).

melting point: 167-168° C.

elemental analysis value ($C_{27}H_{32}N_3O_4F$)

Calculated: C, 67.34; H, 6.70; N, 8.73.

Found: C, 67.17; H, 6.71; N, 8.70.

Example 68

N-(3-{[(2,2-dimethylpropyl)amino]methyl}-8-methylquinolin-7-yl)-2-fluoro-4-[(2S)-tetrahydrofuran-2-ylmethoxy]benzamide

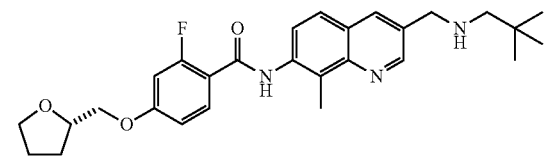 [SMILES: Cc1c(NC(=O)c2ccc(OC[C@@H]3CCCO3)cc2F)ccc2cc(CNCC(C)(C)C)cnc12]

2-Fluoro-N-(3-formyl-8-methylquinolin-7-yl)-4-[(2S)-tetrahydrofuran-2-ylmethoxy]benzamide (1.0 g) obtained in Reference Example 12 and neopentylamine (1.0 g) were suspended in 1-methyl-2-pyrrolidone (20 mL) and acetic acid (7.0 mL) and the mixture was stirred at room temperature for 3 hr. Sodium triacetoxyborohydride (3.0 g) was added, and the mixture was stirred at room temperature for 3 hr. 1N Aqueous sodium hydroxide solution was added to quench the reaction and basify the mixture, and the mixture was partitioned and extracted with ethyl acetate. The organic layer was washed with saturated brine and dried over anhydrous sodium sulfate, and the solvent was evaporated under reduced pressure. The residue was purified by silica gel column chromatography [developing solvent; methanol:ethyl acetate=0:100 (volume ratio)→methanol:ethyl acetate=20:80 (volume ratio)] to give the title compound (490 mg, yield 42%) as a colorless solid.

$^1$H NMR (300 MHz, DMSO-d$_6$) δ: 0.88 (9H, s), 1.64-1.73 (1H, m), 1.83-1.93 (2H, m), 1.97-2.05 (1H, m), 2.15 (1H, br), 2.26 (2H, s), 2.67 (3H, s), 3.69 (1H, q, J=6.3 Hz), 3.79 (1H, q, J=6.3 Hz), 3.92 (2H, s), 3.99-4.11 (2H, m), 4.14-4.20 (1H, m), 6.91-7.02 (2H, m), 7.70-7.78 (3H, m), 8.17 (1H, d, J=1.5 Hz), 8.90 (1H, d, J=2.4 Hz), 9.89 (1H, d, J=2.4 Hz).

melting point: 134-135° C.
elemental analysis value (C$_{28}$H$_{34}$N$_3$O$_3$F)
Calculated: C, 70.12; H, 7.15; N, 8.76.
Found: C, 69.96; H, 7.13; N, 8.70.

Example 69

2-fluoro-N-(3-{[(trans-4-hydroxy-4-methylcyclohexyl)amino]methyl}-8-methylquinolin-7-yl)-4-[(2S)-tetrahydrofuran-2-ylmethoxy]benzamide

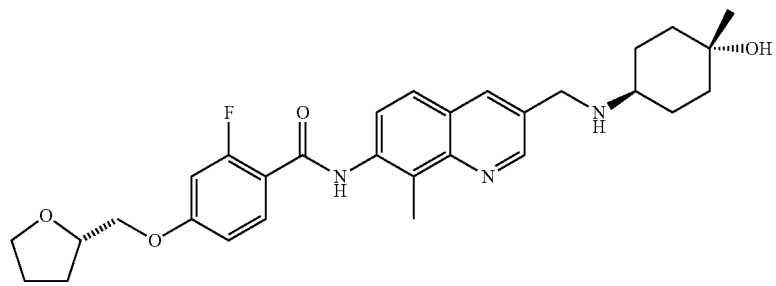 [SMILES: Cc1c(NC(=O)c2ccc(OC[C@@H]3CCCO3)cc2F)ccc2cc(CN[C@H]3CC[C@](C)(O)CC3)cnc12]

2-Fluoro-N-(3-formyl-8-methylquinolin-7-yl)-4-[(2S)-tetrahydrofuran-2-ylmethoxy]benzamide (1.5 g) obtained in Reference Example 12 and trans-4-amino-1-methylcyclohexanol (600 mg) obtained in Reference Example 15 were suspended in 1-methyl-2-pyrrolidone (20 mL) and acetic acid (7.0 mL) and the mixture was stirred at room temperature for 3 hr. Sodium triacetoxyborohydride (3.0 g) was added, and the mixture was stirred at room temperature for 3 hr. 1N Aqueous sodium hydroxide solution was added to quench the reaction and basify the mixture, and the mixture was partitioned and extracted with ethyl acetate. The organic layer was washed with saturated brine and dried over anhydrous sodium sulfate, and the solvent was evaporated under reduced pressure. The residue was purified by silica gel column chromatography [developing solvent; methanol:ethyl acetate=0:100 (volume ratio)→methanol:ethyl acetate=20:80 (volume ratio)] to give the title compound (701 mg, yield 37%) as a colorless solid.

$^1$H NMR (300 MHz, DMSO-d$_6$) δ: 1.10 (3H, s), 1.23-1.35 (4H, m), 1.56-1.59 (2H, m), 1.64-1.73 (1H, m), 1.82-1.90 (4H, m), 1.97-2.07 (1H, m), 2.20 (1H, br), 2.67 (3H, s), 3.33 (1H, br), 3.69 (1H, q, J=7.5 Hz), 3.79 (1H, q, J=7.5 Hz), 3.90 (2H, s), 3.99-4.10 (3H, m), 4.16-4.19 (1H, m), 6.92-7.02 (2H, m), 7.69-7.79 (3H, m), 8.19 (1H, s), 8.88 (1H, s), 9.89 (1H, s).

melting point: 171-172° C.
elemental analysis value (C$_{30}$H$_{36}$N$_3$O$_4$F)
Calculated: C, 69.08; H, 6.96; N, 8.06.
Found: C, 68.86; H, 6.98; N, 7.99.

Example 70

2-fluoro-N-(8-methyl-3-{[(2-methylpropyl)amino]methyl}quinolin-7-yl)-4-[(2S)-tetrahydrofuran-2-ylmethoxy]benzamide

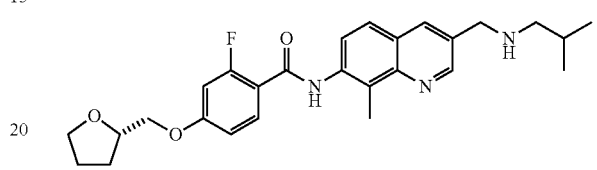

2-Fluoro-N-(3-formyl-8-methylquinolin-7-yl)-4-[(2S)-tetrahydrofuran-2-ylmethoxy]benzamide (1.0 g) obtained in Reference Example 12 and isobutylamine (1.0 g) were suspended in 1-methyl-2-pyrrolidone (20 mL) and acetic acid (7.0 mL) and the mixture was stirred at room temperature for 3 hr. Sodium triacetoxyborohydride (3.0 g) was added, and the mixture was stirred at room temperature for 3 hr. 1N Aqueous sodium hydroxide solution was added to quench the reaction and basify the mixture, and the mixture was partitioned and extracted with ethyl acetate. The organic layer was washed with saturated brine and dried over anhydrous sodium sulfate, and the solvent was evaporated under reduced pressure. The residue was purified by silica gel column chromatography [developing solvent; methanol:ethyl acetate=0:100 (volume ratio)→methanol:ethyl acetate=20:80 (volume ratio)] to give the title compound (700 mg, yield 61%) as a colorless solid.

$^1$H NMR (300 MHz, DMSO-d$_6$) δ: 0.88 (6H, d, J=6.6 Hz), 1.64-1.74 (2H, m), 1.82-1.93 (2H, m), 1.97-2.05 (1H, m), 2.34 (2H, d, J=6.6 Hz), 2.67 (3H, s), 3.69 (1H, q, J=6.6 Hz), 3.79 (1H, q, J=6.6 Hz), 3.89 (2H, s), 3.99-4.11 (3H, m), 4.14-4.20 (1H, m), 6.91-7.02 (2H, m), 7.69-7.79 (3H, m), 8.18 (1H, d, J=1.8 Hz), 8.89 (1H, d, J=2.1 Hz), 9.89 (1H, d, J=2.7 Hz).

melting point: 133-134° C.
elemental analysis value (C$_{27}$H$_{32}$N$_3$O$_3$F)
Calculated: C, 69.66; H, 6.93; N, 9.03.
Found: C, 69.53; H, 6.89; N, 8.97.

Example 71

2-fluoro-N-{8-methyl-3-[(propylamino)methyl]quinolin-7-yl}-4-[(2S)-tetrahydrofuran-2-ylmethoxy]benzamide

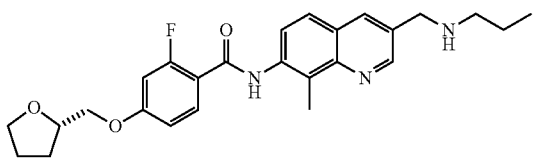 [SMILES: CCCNCc1cnc2c(C)c(NC(=O)c3ccc(OC[C@@H]4CCCO4)cc3F)ccc2c1]

2-Fluoro-N-(3-formyl-8-methylquinolin-7-yl)-4-[(2S)-tetrahydrofuran-2-ylmethoxy]benzamide (1.0 g) obtained in Reference Example 12 and n-propylamine (1.0 g) were suspended in 1-methyl-2-pyrrolidone (20 mL) and acetic acid (7.0 mL) and the mixture was stirred at room temperature for 3 hr. Sodium triacetoxyborohydride (3.0 g) was added, and the mixture was stirred at room temperature for 3 hr. 1N Aqueous sodium hydroxide solution was added to quench the reaction and basify the mixture, and the mixture was partitioned and extracted with ethyl acetate. The organic layer was washed with saturated brine and dried over anhydrous sodium sulfate, and the solvent was evaporated under reduced pressure. The residue was purified by silica gel column chromatography [developing solvent; methanol:ethyl acetate=0:100 (volume ratio)→methanol:ethyl acetate=20:80 (volume ratio)] to give the title compound (680 mg, yield 61%) as a colorless solid.

$^1$H NMR (300 MHz, DMSO-$d_6$) δ: 0.88 (3H, t, J=7.5 Hz), 1.40-1.52 (2H, m), 1.64-1.73 (1H, m), 1.79-1.90 (2H, m), 1.93-2.07 (1H, m), 2.39 (1H, br), 2.47-2.52 (2H, m), 2.67 (3H, s), 3.69 (1H, q, J=6.6 Hz), 3.79 (1H, q, J=6.6 Hz), 3.89 (2H, s), 3.99-4.11 (2H, m), 4.14-4.20 (1H, m), 6.91-7.02 (2H, m), 7.69-7.79 (3H, m), 8.18 (1H, s), 8.88 (1H, d, J=1.8 Hz), 9.89 (1H, d, J=2.4 Hz).

melting point: 120-121° C.
elemental analysis value ($C_{26}H_{30}N_3O_3F$)
Calculated: C, 69.16; H, 6.70; N, 9.31.
Found: C, 68.94; H, 6.71; N, 9.20.

Example 72

N-{3-[(4-hydroxy-4-methylpiperidin-1-yl)methyl]-8-methylquinolin-7-yl}-4-[(2S)-tetrahydrofuran-2-ylmethoxy]benzamide

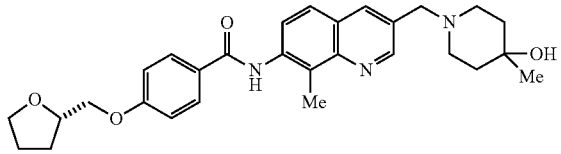 [SMILES: Cc1c(NC(=O)c2ccc(OC[C@@H]3CCCO3)cc2)ccc2cc(CN3CCC(C)(O)CC3)cnc12]

N-(3-Formyl-8-methylquinolin-7-yl)-4-[(2S)-tetrahydrofuran-2-ylmethoxy]benzamide (515 mg) obtained in Reference Example 9,4-methylpiperidin-4-ol monohydrochloride (300 mg) obtained in Reference Example 17, acetic acid (2.64 mL) and sodium triacetoxyborohydride (559 mg) were added to N,N-dimethylacetamide (7.92 mL), and the mixture was stirred at room temperature for 15 hr. The reaction solution was ice-cooled, 8N aqueous sodium hydroxide solution (6.59 mL) was added dropwise, and the mixture was partitioned and extracted with ethyl acetate. The aqueous layer was extracted with ethyl acetate, and the combined organic layer was washed with brine, and purified by silica gel column chromatography [developing solvent; ethyl acetate→ethyl acetate:methanol=1:1(volume ratio)]. The obtained solid was washed with a mixed solvent of ethyl acetate and isopropyl ether and dried under reduced pressure to give the title compound (139 mg, yield 21%) as a pale-yellow solid.

$^1$H NMR (300 MHz, DMSO-$d_6$) δ: 1.10 (3H, s), 1.48 (4H, t, J=5.4 Hz), 1.63-2.09 (4H, m), 2.44 (4H, d, J=5.5 Hz), 2.64 (3H, s), 3.65-3.85 (4H, m), 3.98-4.10 (1H, m), 4.10 (2H, s), 4.15-4.24 (1H, m), 7.09 (2H, d, J=9.0 Hz), 7.59 (1H, d, J=8.7 Hz), 7.80 (1H, d, J=8.7 Hz), 8.02 (2H, d, J=8.9 Hz), 8.17 (1H, d, J=2.1 Hz), 8.85 (1H, d, J=2.1 Hz), 10.06 (1H, s).

melting point: 169-174° C.
elemental analysis value ($C_{29}H_{35}N_3O_4 \cdot 0.6H_2O$)
Calculated: C, 69.60; H, 7.29; N, 8.40.
Found: C, 69.35; H, 7.20; N, 8.37.

Formulation Example 1

| | |
|---|---|
| (1) the compound obtained in Example 1 | 50 mg |
| (2) Lactose | 34 mg |
| (3) Cornstarch | 10.6 mg |
| (4) Cornstarch (paste) | 5 mg |
| (5) Magnesium stearate | 0.4 mg |
| (6) Calcium carboxymethylcellulose | 20 mg |
| total | 120 mg |

The above-mentioned (1) to (6) are mixed according to a conventional method and the mixture is tableted by a tableting machine to give a tablet.

Experimental Example 1

The results are shown in Table 1-1 and Table 1-2.

TABLE 1-1

| | inhibitory activity ($IC_{50}$ value: nM) | |
|---|---|---|
| compound No. | human SLC-1 | rat SLC-1 |
| Example 16 | 2.8 | 3.2 |
| Example 25 | 3.4 | 3.5 |
| Example 27 | 6.3 | 7.8 |
| Example 29 | 3.2 | 4.6 |
| Example 30 | 8.4 | 11 |
| Example 31 | 3.1 | 4.3 |
| Example 32 | 6.0 | 6.4 |
| Example 34 | 5.5 | 6.5 |
| Example 35 | 7.1 | 17 |
| Example 36 | 1.7 | 3.0 |
| Example 37 | 3.0 | 4.1 |
| Example 38 | 1.5 | 1.7 |
| Example 39 | 1.8 | 2.0 |
| Example 40 | 7.7 | 13 |
| Example 41 | 1.5 | 1.6 |
| Example 45 | 3.1 | 5.8 |
| Example 46 | 4.5 | 6.5 |
| Example 47 | 6.8 | 7.9 |
| Example 48 | 9.1 | 8.3 |
| Example 49 | 4.8 | 7.2 |
| Example 50 | 2.9 | 3.9 |
| Example 51 | 4.1 | 5.3 |
| Example 52 | 6.5 | 9.5 |
| Example 54 | 5.5 | 6.1 |

TABLE 1-1-continued

| compound No. | inhibitory activity (IC$_{50}$ value: nM) | |
| --- | --- | --- |
| | human SLC-1 | rat SLC-1 |
| Example 55 | 6.8 | 8.8 |
| Example 56 | 6.4 | 9.1 |
| Example 57 | 9.8 | 17 |
| Example 58 | 6.8 | 11 |
| Example 61 | 2.2 | 2.1 |
| Example 62 | 2.2 | 2.7 |

TABLE 1-2

| compound No. | inhibitory activity (IC$_{50}$ value: nM) | |
| --- | --- | --- |
| | human SLC-1 | rat SLC-1 |
| Example 63 | 3.7 | 4.5 |
| Example 67 | 7.8 | 11 |
| Example 68 | 3.1 | 2.8 |
| Example 69 | 6.1 | 7.1 |
| Example 70 | 2.7 | 3.2 |
| Example 71 | 5.0 | 8.0 |
| Example 72 | 4.5 | 4.3 |

As is clear from Table 1-1 and Table 1-2, the compound of the present invention has a superior MCH receptor antagonistic activity.

Experimental Example 2

Evaluation of Anorectic Effect Using Male F344/Jcl Rats Fed on High-Fat Diet

Male F344/Jcl rats (42-week-old) loaded with a high-fat diet (Research Diets: D12451) from 5 weeks of age were used. From 2 weeks before the start of experiment, the rats were independently raised, a powder high-fat diet (Research Diets: D12451M) was given, tap water (0.5 mL) was administered for acclimation, and thereby the rats were habituated. The food intake from 14:00 the day before the start of experiment to 9:00 the next day was measured, and the rats were grouped based on the food intake and the body weight of the previous day as indices. On the day of the start of experiment and the next day at 16:00, 0.5% methylcellulose solution was administered by gavage to the control group, and 0.5% methylcellulose suspension (10 mg/kg) of the compound was administered by gavage to the compound administration group at 2 mL/kg (6 per group for both control group and compound administration group). The food intake from the initial administration to 48 hr later was measured. The food intake inhibition rate of each compound administration group to the control group was calculated. The results are shown in Table 2.

TABLE 2

| compound No. | food intake inhibition rate (%) |
| --- | --- |
| Example 31 | 24.8*** |
| Example 50 | 30.3*** |

***p ≦ 0.001 (Dunnett's type multiple comparison relative to control group)

As is clear from Table 2, the compound of the present invention shows a superior anorectic effect in obese rat model.

In Experimental Example 3 and Experimental Example 4 below, 4-(cyclopropylmethoxy)-N-[3-[[(trans-4-hydroxycyclohexyl)amino]methyl]-8-methylquinolin-7-yl]benzamide (hereinafter to be referred to as "Comparative Example 1") described in Example 5 of JP-A-2008-088120, and 4-(cyclopropylmethoxy)-N-[3-[[(trans-4-hydroxy-4-methylcyclohexyl)amino]methyl]-8-methylquinolin-7-yl]benzamide (hereinafter to be referred to as "Comparative Example 2") described in Example 9 thereof were used as comparison targets of the compound of the present invention.

Comparative Example 1 and Comparative Example 2 were produced according to the description of JP-A-2008-088120.

Experimental Example 3

Evaluation of HERG Inhibitory Activity

MEM medium, MEM nonessential amino acid solution, sodium pyruvate solution and G418 sulfate solution (Geneticin) were purchased from Invitrogen Corporation (Carlsbad, Calif.). Bovine serum albumin (BSA, Fatty Acid Free) was a product of Wako Pure Chemical Industries, Ltd. (Osaka, Japan). Fetal bovine serum (FCS) was a product of Trau Scientific Ltd. (Melbourne, Australia).

As HERG expression cell HERG.T.HEK, the cell obtained from Wisconsin ALUMNI Research Foundation was used. HERG.T.HEK was maintained and passaged at 37° C. in the presence of 5% $CO_2$ using an MEM medium containing 10% FCS, 1 mM MEM nonessential amino acid, 1 mM sodium pyruvate and 500 μg/ml Geneticin.

80-90% confluent cells were collected by a trypsin treatment and plated on an IVF dish (Falcon, Franklin Lakes, N.J.). After 2-3 hr, cells were adhered to a glass electrode (resistance value 2-3 MΩ) filled with an electrode internal fluid (7 mM NaCl, 130 mM KCl, 1 mM $MgCl_2$, 5 mM HEPES, 5 mM EGTA, 5 mM ATP-Na: pH 7.2) while perfusing with an extracellular fluid (137 mM NaCl, 4 mM KCl, 1 mM $MgCl_2$, 1.8 mM $CaCl_2$, 10 mM HEPES, 11 mM dextrose: pH 7.4), using a patch clamp amplifier AXOPATCH 200B (Axon instruments, Foster City, Calif.), whereby formation of whole-cell configuration and stimulation by voltage clamp protocol were performed (holding potential −75 mV, primary voltage 10 mV: 0.5 sec, secondary voltage −40 mV: 0.5 sec, stimulation frequency 5 sec (Example 31 and Example 50) or 10 sec (Comparative Example 1 and Comparative Example 2). A preliminary stimulation was applied and the HERG electric current value (peak tail current) was measured when the electric current waveform was stabilized.

For measurement of the HERG electric current with addition of the test compound, the cells were first perfused with the extracellular fluid and, when the waveform was stabilized, the cells were perfused with an extracellular fluid containing 10 μm of a test compound. When the electric current waveform was stabilized under respective perfuse conditions, the HERG electric current was measured.

The HERG electric current inhibitory rate (%) of the test compound was calculated with the HERG electric current value without addition of the test compound as 100%. The results are shown in Table 3.

TABLE 3

| compound No. | HERG electric current inhibitory rate (%) of 10 μM compound |
| --- | --- |
| Example 31 | 9.8 |
| Example 50 | 2.1 |

TABLE 3-continued

| compound No. | HERG electric current inhibitory rate (%) of 10 μM compound |
|---|---|
| Com. Ex. 1 | 58 |
| Com. Ex. 2 | 44.9 |

As is clear from Table 3, the compound of the present invention shows low HERG inhibitory activity, and was confirmed to be low toxic.

Experimental Example 4

Evaluation of PLsis

DMEM medium, L-glutamine, penicillin-streptomycin, pyruvic acid, and N-(7-nitrobenz-2-oxa-1,3-diazol-4-yl)-1,2-hexadecanoyl-sn-glycero-3-phosphoethanolamine triethylammonium salt (NBD-PE) were purchased from Invitrogen Corporation. As bovine serum albumin (BSA), a product of Thermo Trace Ltd. (Melbourne, Australia) was used, and as Amiodarone, a product of ICN (Costa Mesa, Calif.) was used. A test compound was used in the form of a 10 mM DMSO solution.

FBS was added at a final concentration of 5 vol % to DMEM medium supplemented with L-glutamine, pyruvic acid and penicillin-streptomycin and subjected to the experiment. Culture was performed using 5% carbon dioxide gas-95% air as a gas phase in a $CO_2$ incubator at 37° C. HepG2 cells were suspended in a culture medium at $50 \times 10^4$ cells/mL, plated in a 96 well plate at 50 μL/well and precultured for 24 hr. After preculture, the culture medium was removed, a culture medium containing 60 μm NBD-PE was added at 50 μL/well, and a culture medium containing 0, 6 μM or 20 μM test compounds were each added at 50 μL/well to HepG2 cells, and the cells were cultured for 24 hr. As a positive control, Amiodarone was used at a final concentration of 10 μM.

After exposure to the test compound for 24 hr, the fluorescence intensity (Ex. 485 nm, Em. 538 nm) of NBD-PE uptaken by the cells was measured by a fluorometer. The measurement value with addition of 0 μM test compound solution was subtracted as a blank, a relative value to the measurement value with addition of 10 μm Amiodarone was calculated, and the maximum value per unit concentration of the test compound was obtained as a phospholipidosis (PLsis) induction potential. The results are shown in Table 4.

TABLE 4

| compound No. | PLsis induction potential |
|---|---|
| Example 31 | 1.7 |
| Example 50 | 1.4 |
| Com. Ex. 1 | 23.5 |
| Com. Ex. 2 | 27.8 |

As is clear from Table 4, the compound of the present invention shows low PLsis induction potential, and was confirmed to be low toxic.

INDUSTRIAL APPLICABILITY

Compound (I) has a melanin-concentrating hormone (MCH) receptor antagonistic action, and is low toxic. Therefore, the compound is highly useful as an agent for the prophylaxis or treatment of obesity and the like.

This application is a National Stage Application of PCT/JP2010/051277, filed Jan. 29, 2010, which claims priority from application No. 2009-020575 filed in Japan on Jan. 30, 2009, the contents of which are incorporated in full herein by this reference.

The invention claimed is:

1. A compound represented by the formula (I):

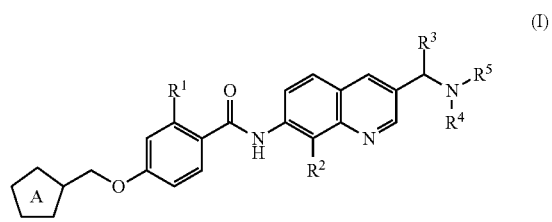

wherein
ring A is a tetrahydrofuran ring optionally further substituted;
$R^1$ is a hydrogen atom or a halogen atom;
$R^2$ is a hydrogen atom, a halogen atom or a $C_{1-6}$ alkyl group;
$R^3$ is a hydrogen atom or a $C_{1-6}$ alkyl group; and
$R^4$ and $R^5$
(1) are each independently a hydrogen atom, an optionally substituted $C_{1-6}$ alkyl group, an optionally substituted $C_{3-10}$ cycloalkyl group, or an optionally substituted 5- or 6-membered heterocyclic group, or
(2) may form, together with the adjacent nitrogen atom, substituted 4- to 6-membered nitrogen-containing heterocycle,
provided that
when one of $R^4$ and $R^5$ is a hydrogen atom, then the other is not a group represented by the formula: $—X^1—R^{41}$
wherein
$X^1$ is a bond or a $C_{1-6}$ alkylene group; and
$R^{41}$ is a group represented by the formula: $—Y—S(O)_{m1}—R^{B1}$
wherein Y is a bond or NH; m1 is an integer of 1 or 2; and $R^{B1}$ is a $C_{1-6}$ alkyl group optionally substituted by 1 to 3 halogen atoms, or a cyclic group represented by the formula:

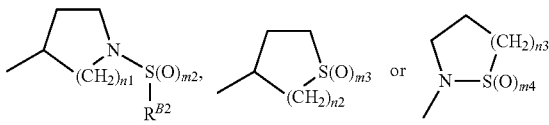

wherein m2, m3, m4, n1, n2 and n3 are each independently an integer of 1 or 2; and $R^{B2}$ is a $C_{1-6}$ alkyl group optionally substituted by 1 to 3 halogen atoms,
(the ring moiety of the cyclic group is optionally further substituted),
or a salt thereof.

2. The compound according to claim 1, wherein $R^1$ is a hydrogen atom or a fluorine atom.

3. The compound according to claim 1, wherein $R^2$ is a fluorine atom or a methyl group.

4. The compound according to claim 1, wherein $R^3$ is a hydrogen atom or a methyl group.

5. The compound according to claim 1, wherein $R^4$ is
  (a) a $C_{1-6}$ alkyl group optionally substituted by 1 to 3 substituents selected from a hydroxy group, a $C_{1-6}$ alkoxy group, and a 5- or 6-membered oxygen-containing heterocyclic group, or
  (b) a $C_{3-10}$ cycloalkyl group optionally substituted by 1 to 3 substituents selected from a hydroxy group and a $C_{1-6}$ alkyl group; and
  $R^5$ is a hydrogen atom.

6. The compound according to claim 1, wherein $R^4$ and $R^5$ form, together with the adjacent nitrogen atom, 4- to 6-membered nitrogen-containing heterocycle substituted by hydroxyl group(s), and the nitrogen-containing heterocycle is optionally substituted by $C_{1-6}$ alkyl group(s).

7. The compound according to claim 1, wherein ring A is a tetrahydrofuran ring;
  $R^1$ is a hydrogen atom or a fluorine atom;
  $R^2$ is a fluorine atom or a methyl group;
  $R^3$ is a hydrogen atom or a methyl group;
  $R^4$ is
  (a) a $C_{1-6}$ alkyl group optionally substituted by 1 to 3 substituents selected from a hydroxy group, a $C_{1-6}$ alkoxy group, and a 5- or 6-membered oxygen-containing heterocyclic group, or
  (b) a $C_{3-10}$ cycloalkyl group optionally substituted by 1 to 3 substituents selected from a hydroxy group and a $C_{1-6}$ alkyl group; and
  $R^5$ is a hydrogen atom.

8. The compound according to claim 1, wherein ring A is a tetrahydrofuran ring;
  $R^1$ is a hydrogen atom or a fluorine atom;
  $R^2$ is a fluorine atom or a methyl group;
  $R^3$ is a hydrogen atom or a methyl group; and
  $R^4$ and $R^5$ form, together with the adjacent nitrogen atom, 5- or 6-membered nitrogen-containing heterocycle substituted by hydroxyl group(s), and the nitrogen-containing heterocycle is optionally substituted by $C_{1-6}$ alkyl group(s).

9. N-[8-Methyl-3-({[(2S)-tetrahydrofuran-2-ylmethyl]amino}methyl)quinolin-7-yl]-4-[(2S)-tetrahydrofuran-2-ylmethoxy]benzamide or a salt thereof.

10. N-{8-Methyl-3-[(tetrahydro-2H-pyran-4-ylamino)methyl]quinolin-7-yl}-4-[(2S)-tetrahydrofuran-2-ylmethoxy]benzamide or a salt thereof.

11. N-(8-Methyl-3-{[(2-methylpropyl)amino]methyl}quinolin-7-yl)-4-[(2S)-tetrahydrofuran-2-ylmethoxy]benzamide or a salt thereof.

12. N-(3-{[(trans-4-Hydroxy-4-methylcyclohexyl)amino]methyl}-8-methylquinolin-7-yl)-4-[(2S)-tetrahydrofuran-2-ylmethoxy]benzamide or a salt thereof.

13. N-{3-[(4-Hydroxy-4-methylpiperidin-1-yl)methyl]-8-methylquinolin-7-yl}-4-[(2S)-tetrahydrofuran-2-ylmethoxy]benzamide or a salt thereof.

14. A medicament comprising the compound according to claim 1.

15. The medicament according to claim 14, which is a melanin-concentrating hormone receptor antagonist.

16. The medicament according to claim 14, which is an anorexigenic agent.

17. The medicament according to claim 14, which is a therapeutic agent for obesity.

18. A method of treating obesity in a mammal, which comprises administering an effective amount of the compound according to claim 1 to said mammal.

* * * * *